(12) United States Patent
Ikuta et al.

(10) Patent No.: US 10,053,732 B2
(45) Date of Patent: Aug. 21, 2018

(54) PROBE OR PROBE SET FOR EVALUATING INFLUENCE OF ULTRAVIOLET RAY ON SKIN AND NUCLEIC ACID MICROARRAY

(71) Applicant: MITSUBISHI RAYON CO., LTD., Chiyoda-ku (JP)

(72) Inventors: Kenjiro Ikuta, Yokohama (JP); Ai Hara, Yokohama (JP); Tatsunobu Fukushima, Yokohama (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 694 days.

(21) Appl. No.: 14/397,755

(22) PCT Filed: May 2, 2013

(86) PCT No.: PCT/JP2013/062779
§ 371 (c)(1),
(2) Date: Oct. 29, 2014

(87) PCT Pub. No.: WO2013/165018
PCT Pub. Date: Nov. 7, 2013

(65) Prior Publication Data
US 2015/0133328 A1 May 14, 2015

(30) Foreign Application Priority Data
May 2, 2012 (JP) ................................. 2012-105085

(51) Int. Cl.
*C12Q 1/68* (2018.01)
*C12Q 1/6876* (2018.01)
*C07H 21/02* (2006.01)

(52) U.S. Cl.
CPC ..... *C12Q 1/6876* (2013.01); *C12Q 2600/136* (2013.01); *C12Q 2600/158* (2013.01)

(58) Field of Classification Search
CPC ............ C12Q 1/6876; C12Q 2600/136; C12Q 2600/158
See application file for complete search history.

(56) References Cited

U.S. PATENT DOCUMENTS

| | | |
|---|---|---|
| 2002/0090624 A1 | 7/2002 | Blumenberg |
| 2002/0197633 A1 | 12/2002 | Jones et al. |
| 2003/0073888 A1 | 4/2003 | Blumenberg |
| 2004/0185485 A1 | 9/2004 | Blumenberg |
| 2011/0217391 A1 | 9/2011 | Muraguchi et al. |
| 2011/0262570 A1 | 10/2011 | Finlay et al. |
| 2014/0342935 A1 | 11/2014 | Ooshima |
| 2015/0133328 A1 | 5/2015 | Ikuta et al. |

FOREIGN PATENT DOCUMENTS

| | | |
|---|---|---|
| JP | 2004-526410 A | 9/2004 |
| JP | 2004-527218 A | 9/2004 |
| JP | 2005-520483 A | 7/2005 |
| JP | 2010-115131 A | 5/2010 |
| JP | 2010-172240 A | 8/2010 |
| JP | 2011-178747 A | 9/2011 |
| JP | WO 2013/080941 A1 | 6/2013 |
| JP | WO 2013/165018 A1 | 11/2013 |
| WO | WO 02/20849 A2 | 3/2002 |
| WO | WO 02/090934 A2 | 11/2002 |
| WO | WO 2011/097572 A1 | 8/2011 |

OTHER PUBLICATIONS

Quan, T. et al., J. Invest. Dermatol., vol. 14, pp. 20-24 (2009).*
Page, E.H., Structure and Function of the Skin, Merck Manual online, downloaded from http://www.merckmanuals.com/home/skin-disorders/biology-of-the-skin/structure-and-function-of-the-skin Jun. 20, 2017.*
Pasparakis, M., Nature Reviews Immunol., vol. 9, pp. 778-788 (2009).*
Tyrrell, R.M, BioEssays, vol. 18, pp. 139-148 (1996).*
Kyng, K.J. et al., Oncogene, vol. 24, pp. 5026-5042 (2005).*
Marionnet, C. et al., J. Invest. Dermatol., vol. 121, pp. 1447-1438 (2003).*
McGrath, J.A. et al., British J. Dermatol., vol. 166, suppl. 2, pp. 9-15 (Jun. 2012).*
Partial Supplementary European Search Report dated Jul. 13, 2015 in Patent Application No. 13784797.6.
Laure Rittié, et al., "UV-light-induced signal cascades and skin aging" Ageing Research Reviews, vol. 1, XP001154285, 2002, pp. 705-720.
Alberto Izzotti, et al., "Alterations of gene expression in skin and lung of mice exposed to light and cigarette smoke" The FASEB Journal Express Article, XP002741117, Aug. 2, 2004, 26 Pages.
Kirstin M. Südel, et al., "Novel Aspects of Intrinsic and Extrinsic Aging of Human Skin: Beneficial Effects of Soy Extract" Photochemistry and Photobiology, vol. 81, XP002741116, 2005, pp. 581-587.
International Search Report dated May 28, 2013 in PCT/JP2013/062779.
Angela Sesto, et al., "Analysis of the ultraviolet B response in primary human keratinocytes using oligonucleotide microarrays" PNAS, vol. 99, No. 5, Mar. 5, 2002, pp. 2965-2970.
Takashi Murakami, et al., "Expression profiling of cancer-related genes in human keratinocytes following non-lethal ultraviolet B irradiation" Journal of Dermatological Science, vol. 27, 2001, pp. 121-129.

(Continued)

*Primary Examiner* — Teresa E Strzelecka
(74) *Attorney, Agent, or Firm* — Oblon, McClelland, Maier & Neustadt, L.L.P.

(57) ABSTRACT

A probe or a probe set for evaluating influence of ultraviolet ray on the skin, which includes nucleic acids of (a), (b) or (c): (a) Nucleic acids including a base sequence constituting at least one kind of gene selected from the group consisting of GBA, GLB1, CAT, OLFM1, ASAH1, MMP14, MMP17 and COL18A1, (b) Nucleic acids including a base sequence complementary to the nucleic acids of aforesaid (a); (c) Nucleic acids which hybridize with nucleic acids including a base sequence complementary to the nucleic acids of aforesaid (a) or (b) under stringent conditions, and can detect a skin constitution-related gene.

9 Claims, 9 Drawing Sheets

(56) References Cited

OTHER PUBLICATIONS

"*Homo sapiens* glucosidase, beta, acid (GBA), transcript variant 1, mRNA," GenBank, NCBI Reference sequence:NM_000157.3, http://www.ncbi.nlm.nih.gov/nuccore/284307148, Mar. 15, 2015, 5 pages.

"*Homo sapiens* galactosidase beta 1 (GLB1), transcript variant 1, mRNA," GenBank, NCBI Reference Sequence:NM_000404.2, http://www.ncbi.nlm.nih.gov/nuccore/119372307, Nov. 7, 2015, 5 pages.

"*Homo sapiens* catalase (CAT), mRNA," GenBank, NCBI Reference Sequence: NM_001752.3, http://www.ncbi.nlm.nih.gov/nuccore/260436908, Sep. 16, 2016, 6 pages.

"*Homo sapiens* olfactomedin 1 (OLFM1), transcript variant 1, mRNA," GenBank, NCBI Reference Sequence: NM_014279.4, http://www.ncbi.nlm.nih.gov/nuccore/150456422, Sep. 9, 2016, 4 pages.

"Cellulomonas fimi ATCC 484, complete genome," GenBank, CP002666.1, http://www.ncbi.nlm.nih.gov/nuccore/CP002666, Oct. 11, 2011, 163 pages.

"*Homo sapiens* matrix metallopeptidase 14 (membrane-inserted) (MMP14), mRNA," GenBank, NCBI Reference Sequence: NM_004995.2, http://www.ncbi.nlm.nih.gov/nuccore/13027797, Jul. 24, 2013, 6 pages.

"*Homo sapiens* matrix metallopeptidase 17 (MMP17), mRNA," GenBank, NCBI Reference Sequence: NM_016155.4, http://www.ncbi.nlm.nih.gov/nuccore/112382269, Dec. 6, 2015, 5 pages.

"*Homo sapiens* collagen type XVIII alpha 1 chain (COL18A1), transcript variant 1, mRNA," GenBank, NCBI Reference Sequence: NM_030582.3, http://www.ncbi.nlm.nih.gov/nuccore/110811234, Aug. 1, 2016, 7 pages.

Yoshikazu Uchida, et al., "Hydrolytic Pathway Protects against Ceramide-Induced Apoptosis in Keratinocytes Exposed to UVB," Journal of Investigative Dermatology, vol. 130, Jun. 3, 2010, pp. 2472-2480.

Makoto Niwa, et al., "Evaluation of the Skin Irritation Using a DNA Microarray on a Reconstructed Human Epidermal Model," Pharmaceutical Society of Japan, vol. 32, No. 2, Feb. 2009, pp. 203-208.

Noriyuki Omagari, et al., "Three Dimensional Arrangement of Fibrocytes in the Dermal Papilla of the Human Sole Skin," Ministry of Education, Science, and Culture, vol. 67, No. 59570020, Aug. 1990, pp. 195-202.

\* cited by examiner

SEQUENCE LISTING

```
<160> NUMBER OF SEQ ID NOS: 273

<210> SEQ ID NO 1
<211> LENGTH: 65
<212> TYPE: DNA
<213> ORGANISM: Homo sapiens

<400> SEQUENCE: 1
cgccgtctgg cgagccctta gccttgctgt agagacttcc gtcacccttg gtagagttta      60
ttttt                                                                  65

<210> SEQ ID NO 2
<211> LENGTH: 65
<212> TYPE: DNA
<213> ORGANISM: Homo sapiens

<400> SEQUENCE: 2
tgggggctct ctccaccctt ctcagagttc cagtttcaac cagagttcca accaatgggc      60
tccat                                                                  65

<210> SEQ ID NO 3
<211> LENGTH: 65
```

-continued

```
<212> TYPE: DNA
<213> ORGANISM: Homo sapiens

<400> SEQUENCE: 3
aggagattcc acacagggt ggagtttctg acgaaggtcc taagggagtg tttgtgtctg    60
actca                                                               65

<210> SEQ ID NO 4
<211> LENGTH: 65
<212> TYPE: DNA
<213> ORGANISM: Homo sapiens

<400> SEQUENCE: 4
ttctgccact tggacatcat ctgggtgaac actcctgaac agacagctcc ttacggcctg    60
ggaaa                                                                65

<210> SEQ ID NO 5
<211> LENGTH: 65
<212> TYPE: DNA
<213> ORGANISM: Homo sapiens

<400> SEQUENCE: 5
cccgtgcagc agaagcatgc gactttcata tccttgccta aataggctg catggtgtat    60 gtcag                                                                65

<210> SEQ ID NO 6
<211> LENGTH: 65
<212> TYPE: DNA
<213> ORGANISM: Homo sapiens

<400> SEQUENCE: 6
caccatctga taccgtaagg agtgcacttg tttggaagtt ctgacttctc tgatctgtct    60
tggtc                                                                65

<210> SEQ ID NO 7
<211> LENGTH: 65
<212> TYPE: DNA
<213> ORGANISM: Homo sapiens

<400> SEQUENCE: 7
ctgcttctga ttccacaagg ggcttttcc tcaaccctgt ggccgccttt gaagtgactc     60
atttt                                                                65

<210> SEQ ID NO 8
<211> LENGTH: 65
<212> TYPE: DNA
<213> ORGANISM: Homo sapiens

<400> SEQUENCE: 8
ctagccttga ggagtgtgag aatcaaaact ctcctacact tccattaact tagcatgtgt    60
tgaaa                                                                65

<210> SEQ ID NO 9
<211> LENGTH: 65
<212> TYPE: DNA
<213> ORGANISM: Homo sapiens

<400> SEQUENCE: 9
cacctctctt tttcagttgg ctgacttcca cacctagcat ctcatgagtg ccaagcaaaa    60
``` ggaga                                                            65

<210> SEQ ID NO 10
<211> LENGTH: 65
<212> TYPE: DNA
<213> ORGANISM: Homo sapiens

<400> SEQUENCE: 10
tctacgatag gtctgataat gggtgggacg ctcctggctt tgctaagaaa gcgtttcaga    60
caaaa                                                            65

<210> SEQ ID NO 11
<211> LENGTH: 65
<212> TYPE: DNA
<213> ORGANISM: Homo sapiens

<400> SEQUENCE: 11
actttgagaa caggaagaaa gaggaggagg agctcgtttc tctcaaagac aggatcgaga    60
gacgt                                                            65

<210> SEQ ID NO 12
<211> LENGTH: 65
<212> TYPE: DNA
<213> ORGANISM: Homo sapiens

<400> SEQUENCE: 12
acatcgtttt gttaagaagt taactgtatc gtagctcact actgccagag cggcaatgga    60
tgtac                                                            65

<210> SEQ ID NO 13
<211> LENGTH: 65
<212> TYPE: DNA
<213> ORGANISM: Homo sapiens

<400> SEQUENCE: 13
cgggcttgtc agagctactt ccactgtgta tcctgcatca gcggtcctct aggcctatat    60
aggaa                                                            65

<210> SEQ ID NO 14
<211> LENGTH: 65
<212> TYPE: DNA
<213> ORGANISM: Homo sapiens

<400> SEQUENCE: 14
gacgtttgca gtcacacaca acaccttagt tcctctaggg gctgtacagt attgtggcat    60
cagat                                                            65

<210> SEQ ID NO 15
<211> LENGTH: 65
<212> TYPE: DNA
<213> ORGANISM: Homo sapiens

<400> SEQUENCE: 15
gggtcttcag ctttatcccc gtttcttgca agggaagagc ctttatacaa ttggacgcat    60
tttgg                                                            65

<210> SEQ ID NO 16
<211> LENGTH: 65
<212> TYPE: DNA
<213> ORGANISM: Homo sapiens

```
<400> SEQUENCE: 16
cccaaacact tctgctttca cttaagtgtc tggcccgcaa tactgtagga acaagcatga    60
tcttg                                                              65

<210> SEQ ID NO 17
<211> LENGTH: 65
<212> TYPE: DNA
<213> ORGANISM: Homo sapiens

<400> SEQUENCE: 17
aagctaacaa aagcaaacac cgtatcactc tgattgttga cgggaacgca gttggcgctg    60
aaagt                                                              65

<210> SEQ ID NO 18
<211> LENGTH: 65
<212> TYPE: DNA
<213> ORGANISM: Homo sapiens

<400> SEQUENCE: 18
atgcaactct gacgttgatc ccagagagca gcttcagtga caaacatatc ctttcaagac    60
agaaa                                                              65

<210> SEQ ID NO 19
<211> LENGTH: 65
<212> TYPE: DNA
<213> ORGANISM: Homo sapiens

<400> SEQUENCE: 19
tcactctact tagcatgtcc ctaccgagtc tcttctccac tggatggagg aaaaccaagc    60
cgtgg                                                              65

<210> SEQ ID NO 20
<211> LENGTH: 65
<212> TYPE: DNA
<213> ORGANISM: Homo sapiens

<400> SEQUENCE: 20
ttcccaagag aaggggaagc actcgtgtgc aacagacaag tgactgtatc tgtgtagact    60
atttg                                                              65

<210> SEQ ID NO 21
<211> LENGTH: 65
<212> TYPE: DNA
<213> ORGANISM: Homo sapiens

<400> SEQUENCE: 21
cttggccatt ctttgggtat gggacattcc tctgatccta atgcagtgat gtatccaacc    60
tatgg                                                              65

<210> SEQ ID NO 22
<211> LENGTH: 65
<212> TYPE: DNA
<213> ORGANISM: Homo sapiens

<400> SEQUENCE: 22
acgtcttcca gtaccgagag aaagcctatt tctgccagga ccgcttctac tggcgcgtga    60
gttcc                                                              65
```

<210> SEQ ID NO 23
<211> LENGTH: 65
<212> TYPE: DNA
<213> ORGANISM: Homo sapiens

<400> SEQUENCE: 23
cacacatatt aaagagtaac agctggttac attgctaggc gagatagggg gaagacagat    60
atggg                                                                65

<210> SEQ ID NO 24
<211> LENGTH: 65
<212> TYPE: DNA
<213> ORGANISM: Homo sapiens

<400> SEQUENCE: 24
tgtctcagac tgggcaggga ggctttggca tgacttaaga ggaagggcag tcttgggccc    60
gctat                                                                65

<210> SEQ ID NO 25
<211> LENGTH: 65
<212> TYPE: DNA
<213> ORGANISM: Homo sapiens

<400> SEQUENCE: 25
aggaggcaca aacttgttcc tcactgctgt tcacgagatt ggccattcct taggtcttgg    60
ccatt                                                                65

<210> SEQ ID NO 26
<211> LENGTH: 65
<212> TYPE: DNA
<213> ORGANISM: Homo sapiens

<400> SEQUENCE: 26
ggggagggtg cttggcactt attgaatata tgatcggcca tcaagggaag aactattgtg    60
ctcag                                                                65

<210> SEQ ID NO 27
<211> LENGTH: 65
<212> TYPE: DNA
<213> ORGANISM: Homo sapiens

<400> SEQUENCE: 27
gcacggggta ggggaaatgg ggtgaacggt gctggcagtt cggctagatt tctgtcttgt    60
ttgtt                                                                65

<210> SEQ ID NO 28
<211> LENGTH: 65
<212> TYPE: DNA
<213> ORGANISM: Homo sapiens

<400> SEQUENCE: 28
ggtggggctg cggggggttcc gtgtccaccc ccatacattt atttctgtaa ataatgtgca    60
ctgaa                                                                65

<210> SEQ ID NO 29
<211> LENGTH: 65
<212> TYPE: DNA
<213> ORGANISM: Homo sapiens

<400> SEQUENCE: 29

```
gggccaagaa agcaagaaat gagaaccaga gtcagccctg tagctttact tcagtgcttc    60
cattc                                                                65

<210> SEQ ID NO 30
<211> LENGTH: 65
<212> TYPE: DNA
<213> ORGANISM: Homo sapiens

<400> SEQUENCE: 30
atttctttaa ggaccagctg tactggcgct acgatgacca cacgaggcac atggaccccg    60
gctac                                                                65

<210> SEQ ID NO 31
<211> LENGTH: 65
<212> TYPE: DNA
<213> ORGANISM: Homo sapiens

<400> SEQUENCE: 31
ttattagctc acacctgtcc actcacatga aactcgtgtt aggccctggg aggccgacgg    60
taact                                                                65

<210> SEQ ID NO 32
<211> LENGTH: 65
<212> TYPE: DNA
<213> ORGANISM: Homo sapiens

<400> SEQUENCE: 32
atggcctgaa ccccatgggt agagtcactt aggggccact tcctaagttg ctgtccagcc    60
tcagt                                                                65

<210> SEQ ID NO 33
<211> LENGTH: 65
<212> TYPE: DNA
<213> ORGANISM: Homo sapiens

<400> SEQUENCE: 33
ttccctgttt atccatcccc tgcaaactgc agagtggcac tcattgcttg tggacggacc    60
agctc                                                                65

<210> SEQ ID NO 34
<211> LENGTH: 65
<212> TYPE: DNA
<213> ORGANISM: Homo sapiens

<400> SEQUENCE: 34
tgacaagcag actgcgcatg tctctgatgc tttgtatcat tcttgagcaa tcgctcggtc    60
cgtgg                                                                65

<210> SEQ ID NO 35
<211> LENGTH: 65
<212> TYPE: DNA
<213> ORGANISM: Homo sapiens

<400> SEQUENCE: 35
ttgggggtag aggcttctta gattctccca gcatccgcct ttccctttag ccagtctgct    60
gtcct                                                                65

<210> SEQ ID NO 36
```

<210> SEQ ID NO 36
<211> LENGTH: 65
<212> TYPE: DNA
<213> ORGANISM: Homo sapiens

<400> SEQUENCE: 36
gcccctgcct cccaaacccc attagtctag ccttgtagct gttactgcaa gtgtttcttc    60
tggct                                                                65

<210> SEQ ID NO 37
<211> LENGTH: 65
<212> TYPE: DNA
<213> ORGANISM: Homo sapiens

<400> SEQUENCE: 37
cccatgaatc tgtctcccag ttatgaatca gtgggcagga taaactgaaa actcccattt    60
acgtg                                                                65

<210> SEQ ID NO 38
<211> LENGTH: 65
<212> TYPE: DNA
<213> ORGANISM: Homo sapiens

<400> SEQUENCE: 38
cctgcatggt gtttatgcac acagagattt gagaaccatt gttctgaatg ctgcttccat    60
ttgac                                                                65

<210> SEQ ID NO 39
<211> LENGTH: 65
<212> TYPE: DNA
<213> ORGANISM: Homo sapiens

<400> SEQUENCE: 39
aaccttctca ggaggtgtct cctaccctct tattgttcct cttacgctct gctcaatgaa    60
acctt                                                                65

<210> SEQ ID NO 40
<211> LENGTH: 65
<212> TYPE: DNA
<213> ORGANISM: Homo sapiens

<400> SEQUENCE: 40
accttcaacg agacgcagat tgagtggttc cgcgctggca gtgccctcaa cagaatgaag    60
gaact                                                                65

<210> SEQ ID NO 41
<211> LENGTH: 65
<212> TYPE: DNA
<213> ORGANISM: Homo sapiens

<400> SEQUENCE: 41
aaaactgacc gggacctgtg caagccgaat tctctggtgg ttgagatccc gccatttcgg    60
aatca                                                                65

<210> SEQ ID NO 42
<211> LENGTH: 65
<212> TYPE: DNA
<213> ORGANISM: Homo sapiens

<400> SEQUENCE: 42
aggcgtagcg gaagttactg cagccgcggt gttgtgctgt ggggaaggga gaaggatttg    60
taaac                                                              65

<210> SEQ ID NO 43
<211> LENGTH: 65
<212> TYPE: DNA
<213> ORGANISM: Homo sapiens

<400> SEQUENCE: 43
tcttctgccg ctcctggtgc tgcttgtgtg ctcgtttggt gcggacctgg tacctctttt    60
gtgaa                                                              65

<210> SEQ ID NO 44
<211> LENGTH: 65
<212> TYPE: DNA
<213> ORGANISM: Homo sapiens

<400> SEQUENCE: 44
cccatggaat gatgacttca tgttcttctc gtgggtttgt gccgtgctgc tttccaaata    60
ggtat                                                              65

<210> SEQ ID NO 45
<211> LENGTH: 65
<212> TYPE: DNA
<213> ORGANISM: Homo sapiens

<400> SEQUENCE: 45
cccacaaact gatttctcac ggcgtgtcac cccaccaggg cgcaagcctc actattactt    60
gaact                                                              65

<210> SEQ ID NO 46
<211> LENGTH: 65
<212> TYPE: DNA
<213> ORGANISM: Homo sapiens

<400> SEQUENCE: 46
cctagacccg tgacctgaga tgtgtgattt ttagtcatta aatggaagtg tctgccagct    60
gggcc                                                              65

<210> SEQ ID NO 47
<211> LENGTH: 65
<212> TYPE: DNA
<213> ORGANISM: Homo sapiens

<400> SEQUENCE: 47
gggagagatg agtgggttag ctacctgcta tgcgctagtt aggaagttac ctggatgcca    60
ttgta                                                              65

<210> SEQ ID NO 48
<211> LENGTH: 65
<212> TYPE: DNA
<213> ORGANISM: Homo sapiens

<400> SEQUENCE: 48
aacctaagaa taagcaagtc ttctttccag gtcaccactt gcaagctaca tggaggttcc    60
ccctg                                                              65

<210> SEQ ID NO 49
<211> LENGTH: 65
<212> TYPE: DNA

<213> ORGANISM: Homo sapiens

<400> SEQUENCE: 49
ctcacctgta gcagccagtc ccgtttcatt tagtcatgtg accactctgt cttgtgtttc    60
cacag                                                                65

<210> SEQ ID NO 50
<211> LENGTH: 65
<212> TYPE: DNA
<213> ORGANISM: Homo sapiens

<400> SEQUENCE: 50
gcatgctgga agccaggaag gcctatgtga acatgtcgct gtttgagaac ttcacttacg    60
cgggc                                                                65

<210> SEQ ID NO 51
<211> LENGTH: 65
<212> TYPE: DNA
<213> ORGANISM: Homo sapiens

<400> SEQUENCE: 51
gacggatgcc agcttgggca ctgctgtcta ctgaccccaa cccttgatga tatgtattta    60
ttcat                                                                65

<210> SEQ ID NO 52
<211> LENGTH: 65
<212> TYPE: DNA
<213> ORGANISM: Homo sapiens

<400> SEQUENCE: 52
gggagcactg ggttgacttt caggtactaa atacctcaac ctatggtata atggttgact    60
gggtt                                                                65

<210> SEQ ID NO 53
<211> LENGTH: 65
<212> TYPE: DNA
<213> ORGANISM: Homo sapiens

<400> SEQUENCE: 53
ggcatggggt ctgttctgaa atgtaaaggg ttcagacggg gtttctggtt ttagaaggtt    60
gcgtg                                                                65

<210> SEQ ID NO 54
<211> LENGTH: 65
<212> TYPE: DNA
<213> ORGANISM: Homo sapiens

<400> SEQUENCE: 54
ctgttccttg tgtaactgtg ttgctgaaag actacctcgt tcttgtcttg atgtgtcacc    60
ggggc                                                                65

<210> SEQ ID NO 55
<211> LENGTH: 65
<212> TYPE: DNA
<213> ORGANISM: Homo sapiens

<400> SEQUENCE: 55
aggagctcca aggacaagaa acacgtctgg ctaggagaaa ctatcaatgc tggcagccag    60
tttga                                                                65

<210> SEQ ID NO 56
<211> LENGTH: 65
<212> TYPE: DNA
<213> ORGANISM: Homo sapiens

<400> SEQUENCE: 56
tcagcagggc atcgcatgga ccgcaggagg gcagattcgg accactaggc ctgaaatgac    60
atttc                                                                65

<210> SEQ ID NO 57
<211> LENGTH: 65
<212> TYPE: DNA
<213> ORGANISM: Homo sapiens

<400> SEQUENCE: 57
atcagaccaa caaaccttcc ccctgaaaag tgagcagcaa cgtaaaaacg tatgtgaagc    60
ctctc                                                                65

<210> SEQ ID NO 58
<211> LENGTH: 65
<212> TYPE: DNA
<213> ORGANISM: Homo sapiens

<400> SEQUENCE: 58
tgtgcacaaa acccagacct gttagcagac aggccccgtg aggcaatggg agctgaggcc    60
acact                                                                65

<210> SEQ ID NO 59
<211> LENGTH: 65
<212> TYPE: DNA
<213> ORGANISM: Homo sapiens

<400> SEQUENCE: 59
gggggtcgtg gcagataatc agcctcttaa agctgcctgt agttaggaaa taaaaccttt    60
caaat                                                                65

<210> SEQ ID NO 60
<211> LENGTH: 65
<212> TYPE: DNA
<213> ORGANISM: Homo sapiens

<400> SEQUENCE: 60
gcccaataaa cattcccttg gatgtagtct gaggcccctt aactcatctg ttatcctgct    60
agctg                                                                65

<210> SEQ ID NO 61
<211> LENGTH: 65
<212> TYPE: DNA
<213> ORGANISM: Homo sapiens

<400> SEQUENCE: 61
ggcagctcat gcttgagacc caatctccat gatgacctac aagctagagt atttaaaggc    60
agtgg                                                                65

<210> SEQ ID NO 62
<211> LENGTH: 65
<212> TYPE: DNA
<213> ORGANISM: Homo sapiens

<400> SEQUENCE: 62
actcagtagg tctgaaggcc tccatttgta ccgaaacacc ccgctcacgc tgacagcctc    60
ctagg                                                                65

<210> SEQ ID NO 63
<211> LENGTH: 65
<212> TYPE: DNA
<213> ORGANISM: Homo sapiens

<400> SEQUENCE: 63
gccttctgcc ctggagcaca gcatccaata ttctggagaa gtgcggagat tcaacactgc    60
caatg                                                                65

<210> SEQ ID NO 64
<211> LENGTH: 65
<212> TYPE: DNA
<213> ORGANISM: Homo sapiens

<400> SEQUENCE: 64
acgagggagg aacacctgat cttacagaaa ataccacctc gagatgggtg ctggtcctgt    60
tgatc                                                                65

<210> SEQ ID NO 65
<211> LENGTH: 65
<212> TYPE: DNA
<213> ORGANISM: Homo sapiens

<400> SEQUENCE: 65
gtgaagtgca tcaaacttgg gaaagatttg aggaggctgg gaacctcctg gaaaaccact    60
ccttg                                                                65

<210> SEQ ID NO 66
<211> LENGTH: 65
<212> TYPE: DNA
<213> ORGANISM: Homo sapiens

<400> SEQUENCE: 66
gcctggccgt gatagaaact ttcagctgag gagtctatat gccatactac tctatgtggc    60
atctt                                                                65

<210> SEQ ID NO 67
<211> LENGTH: 65
<212> TYPE: DNA
<213> ORGANISM: Homo sapiens

<400> SEQUENCE: 67
aatagccacc ttgcccttgt agaatccatc cgcccatccg tccattcatc catcggtccg    60
tccat                                                                65

<210> SEQ ID NO 68
<211> LENGTH: 65
<212> TYPE: DNA
<213> ORGANISM: Homo sapiens

<400> SEQUENCE: 68
tgatctggct gacctggggg caaccaagga ccgtatcatt tctgagatta acaggctgca    60
gcagg                                                                65

<210> SEQ ID NO 69
<211> LENGTH: 65
<212> TYPE: DNA
<213> ORGANISM: Homo sapiens

<400> SEQUENCE: 69
cggtttgtat gtaatggaag cacggggcta gagtttccac ataggcccca acataaaggc    60
cttcc                                                                65

<210> SEQ ID NO 70
<211> LENGTH: 65
<212> TYPE: DNA
<213> ORGANISM: Homo sapiens

<400> SEQUENCE: 70
atgaagcctg ggcccacaac tcatccaact acacgctccc ggcctttat atggggaact     60 tctcc                                                                65

<210> SEQ ID NO 71
<211> LENGTH: 65
<212> TYPE: DNA
<213> ORGANISM: Homo sapiens

<400> SEQUENCE: 71
ccttgcctta catagggtaa agaccaagaa atgccaaacg tgaactaaaa tatgtagggc    60
cttca                                                                65

<210> SEQ ID NO 72
<211> LENGTH: 65
<212> TYPE: DNA
<213> ORGANISM: Homo sapiens

<400> SEQUENCE: 72
tcgccgtgca gcgcatcttc gaaaacggct acgaccccgt aaacttgctc aacgacatcg    60
tgatt                                                                65

<210> SEQ ID NO 73
<211> LENGTH: 65
<212> TYPE: DNA
<213> ORGANISM: Homo sapiens

<400> SEQUENCE: 73
caagtgcacg gtcgaattat tgtgcaagtg gcttttggat atcctgattg gggcctaaga    60
agggc                                                                65

<210> SEQ ID NO 74
<211> LENGTH: 65
<212> TYPE: DNA
<213> ORGANISM: Homo sapiens

<400> SEQUENCE: 74
gccaaatgga tttagaaatt cccttgtgag tgcctggtag ctaatacact ggtcagagat    60
ctggt                                                                65

<210> SEQ ID NO 75
<211> LENGTH: 65
<212> TYPE: DNA
<213> ORGANISM: Homo sapiens

<400> SEQUENCE: 75

```
ggcgtaggtc tggagtctca cttgtctcac ttgtgcagtg ttgacagttc atatgtacca    60
tgtac                                                                65

<210> SEQ ID NO 76
<211> LENGTH: 65
<212> TYPE: DNA
<213> ORGANISM: Homo sapiens

<400> SEQUENCE: 76
aatccccagc cctttgttg agccaggcct ctctcacctc tcctactcac ttaaagcccg     60
cctga                                                                65

<210> SEQ ID NO 77
<211> LENGTH: 65
<212> TYPE: DNA
<213> ORGANISM: Homo sapiens

<400> SEQUENCE: 77
ggcccggcgt ctcctgaacc tgagtagaga cactgctgct gagatgaatg aaacagtaga    60
agtca                                                                65

<210> SEQ ID NO 78
<211> LENGTH: 65
<212> TYPE: DNA
<213> ORGANISM: Homo sapiens

<400> SEQUENCE: 78
gatctgctga caaaacctgg gaatttgggt tgtgtatgcg aatgtttcag tgcctcagac    60
aaatg                                                                65

<210> SEQ ID NO 79
<211> LENGTH: 65
<212> TYPE: DNA
<213> ORGANISM: Homo sapiens

<400> SEQUENCE: 79
cctagaaatt gacacaagtg gaccttaggc cttcctctct ccagatgttt ccagacttcc    60
ttgag                                                                65

<210> SEQ ID NO 80
<211> LENGTH: 65
<212> TYPE: DNA
<213> ORGANISM: Homo sapiens

<400> SEQUENCE: 80
acagccactc acctcttcag aacgaattga caaacaaatt cggtacatcc tcgacggcat    60
ctcag                                                                65

<210> SEQ ID NO 81
<211> LENGTH: 65
<212> TYPE: DNA
<213> ORGANISM: Homo sapiens

<400> SEQUENCE: 81
gtttctcctt tatttctaag tggaaaaagt attagccacc atcttacctc acagtgatgt    60
tgtga                                                                65

<210> SEQ ID NO 82
<211> LENGTH: 65
```

<212> TYPE: DNA
<213> ORGANISM: Homo sapiens

<400> SEQUENCE: 82
actatccaac cacccaacaa cttgcctgtg tcttgagaag atagccccgg tcaggacttg      60
cacct                                                                 65

<210> SEQ ID NO 83
<211> LENGTH: 65
<212> TYPE: DNA
<213> ORGANISM: Homo sapiens

<400> SEQUENCE: 83
ccaggaactc ttactctagt tagaatttgt accagatcca aggtgaaaac cccaataagc      60
aactg                                                                 65

<210> SEQ ID NO 84
<211> LENGTH: 65
<212> TYPE: DNA
<213> ORGANISM: Homo sapiens

<400> SEQUENCE: 84
gctgtctgac cttccaaaga ctaagactcg cggcaggttc tctttgagtc aatagcttgt      60
cttcg                                                                 65

<210> SEQ ID NO 85
<211> LENGTH: 65
<212> TYPE: DNA
<213> ORGANISM: Homo sapiens

<400> SEQUENCE: 85
gacatcacca aggacacgtt ttacaaacag cccatgttct accaccttgg ccacttcagc      60
aagtt                                                                 65

<210> SEQ ID NO 86
<211> LENGTH: 65
<212> TYPE: DNA
<213> ORGANISM: Homo sapiens

<400> SEQUENCE: 86
cctccctaat cctattatct ttcaatggtt accttgactt aacctattga gttacctggt      60
cagca                                                                 65

<210> SEQ ID NO 87
<211> LENGTH: 65
<212> TYPE: DNA
<213> ORGANISM: Homo sapiens

<400> SEQUENCE: 87
caacatggac ggccacatct tcgccagcat cgacatgcct gccatcaaca agggcaacaa      60
gaaag                                                                 65

<210> SEQ ID NO 88
<211> LENGTH: 65
<212> TYPE: DNA
<213> ORGANISM: Homo sapiens

<400> SEQUENCE: 88
ccatacccct aggagtggtt tgagtagtac agacctcgaa gccttgctgc taacactgag      60

```
gtagc                                                              65

<210> SEQ ID NO 89
<211> LENGTH: 65
<212> TYPE: DNA
<213> ORGANISM: Homo sapiens

<400> SEQUENCE: 89
ggtgggtttg cctagggacg tgtaactaca ggcttttact aagccaagga aaagagaat   60 ttttc                                                              65

<210> SEQ ID NO 90
<211> LENGTH: 65
<212> TYPE: DNA
<213> ORGANISM: Homo sapiens

<400> SEQUENCE: 90
cacccttatg aacctctact ggttcctgta catcgtggcg tttgcagcca aggtgttgac   60
aggcc                                                              65

<210> SEQ ID NO 91
<211> LENGTH: 65
<212> TYPE: DNA
<213> ORGANISM: Homo sapiens

<400> SEQUENCE: 91
cgggacctaa gaaagtctct gcagccagat agtacatggt gtctccacaa aactaggcat   60
tctgg                                                              65

<210> SEQ ID NO 92
<211> LENGTH: 65
<212> TYPE: DNA
<213> ORGANISM: Homo sapiens

<400> SEQUENCE: 92
ccagtgatgc tcagaagctc ccctggcaca atttcagagt aagagctcgg tgataccaag   60
aagtg                                                              65

<210> SEQ ID NO 93
<211> LENGTH: 65
<212> TYPE: DNA
<213> ORGANISM: Homo sapiens

<400> SEQUENCE: 93
ggcagctatg gtagtgcaga ttatgattat ggtgaatccg ggtttagaca ctctcagcac   60
ggaag                                                              65

<210> SEQ ID NO 94
<211> LENGTH: 65
<212> TYPE: DNA
<213> ORGANISM: Homo sapiens

<400> SEQUENCE: 94
gtgggggaga caaaggcaag agtcagagtc aagtctgtca ggaggtatca gaatatacgg   60
tgagg                                                              65

<210> SEQ ID NO 95
<211> LENGTH: 65
<212> TYPE: DNA
<213> ORGANISM: Homo sapiens
```

<400> SEQUENCE: 95
agctctagtt ctcccccagc atcactaaca aatatgcttg gcaagaccga ggtcgatttg    60
tccca                                                                65

<210> SEQ ID NO 96
<211> LENGTH: 65
<212> TYPE: DNA
<213> ORGANISM: Homo sapiens

<400> SEQUENCE: 96
tttcatcaaa tgtggcatcc aaggctgcct ttggaggttc tggaggtaga gggtccagtt    60
ccgga                                                                65

<210> SEQ ID NO 97
<211> LENGTH: 65
<212> TYPE: DNA
<213> ORGANISM: Homo sapiens

<400> SEQUENCE: 97 tcttttgag aatcacatca actacctgcg gagctacctg gacaacatcc tcggggagag     60
agggc                                                                65

<210> SEQ ID NO 98
<211> LENGTH: 65
<212> TYPE: DNA
<213> ORGANISM: Homo sapiens

<400> SEQUENCE: 98
tctcccacta gatcctgtat tatccatcta catcagaacc aaactacttc tccaacaccc    60
ggcag                                                                65

<210> SEQ ID NO 99
<211> LENGTH: 65
<212> TYPE: DNA
<213> ORGANISM: Homo sapiens

<400> SEQUENCE: 99
cacgcagctg ggtagatata cagctgtcac aagagtctag atcagttagc acatgctttc    60
tactc                                                                65

<210> SEQ ID NO 100
<211> LENGTH: 65
<212> TYPE: DNA
<213> ORGANISM: Homo sapiens

<400> SEQUENCE: 100
ggcactcgcg aggcgacttc tcaagctttt gaatgggtga gtggtcgggt atctagtttt    60
tgcac                                                                65

<210> SEQ ID NO 101
<211> LENGTH: 65
<212> TYPE: DNA
<213> ORGANISM: Homo sapiens

<400> SEQUENCE: 101
gccccattgg gcatgataag ccgaggaggc attcttctaa agcagacttt tgtgtaaaaa    60
gcaaa                                                                65

<210> SEQ ID NO 102
<211> LENGTH: 65
<212> TYPE: DNA
<213> ORGANISM: Homo sapiens

<400> SEQUENCE: 102
gttccctgtg gctgctgata acccaacatt ccatctctac cctcatactt caaaattaaa    60
tcaag                                                                65

<210> SEQ ID NO 103
<211> LENGTH: 65
<212> TYPE: DNA
<213> ORGANISM: Homo sapiens

<400> SEQUENCE: 103
gcttcccaga gaccctgggt ctagaaagcg gctcctgaag gtcccttatt gtggctgata    60
ttaac                                                                65

<210> SEQ ID NO 104
<211> LENGTH: 65
<212> TYPE: DNA
<213> ORGANISM: Homo sapiens

<400> SEQUENCE: 104
cctgcagccc cagaagaaat taggggttaa agcagacagt cacactggtt tggtcagtta    60
caaag                                                                65

<210> SEQ ID NO 105
<211> LENGTH: 65
<212> TYPE: DNA
<213> ORGANISM: Homo sapiens

<400> SEQUENCE: 105
ggatgtaggg gttaacttgg tcagagccac tctatgagtt ggacttcagt cttgcctagg    60
cgatt                                                                65

<210> SEQ ID NO 106
<211> LENGTH: 65
<212> TYPE: DNA
<213> ORGANISM: Homo sapiens

<400> SEQUENCE: 106
gccaagtcat agccataaat gatgagtcgg tcctctttcc agtggatcat aagacaatgg    60
accct                                                                65

<210> SEQ ID NO 107
<211> LENGTH: 65
<212> TYPE: DNA
<213> ORGANISM: Homo sapiens

<400> SEQUENCE: 107
ggcggcttga tggtaatcag tatctgtttt tgccaccaaa tcgttacatt ttccatggcg    60
ctgag                                                                65

<210> SEQ ID NO 108
<211> LENGTH: 65
<212> TYPE: DNA
<213> ORGANISM: Homo sapiens

<400> SEQUENCE: 108
ggctaagtaa accataccta acctacccca gtgtgggtgt gggcctctga atataaccca    60
caccc                                                                65

<210> SEQ ID NO 109
<211> LENGTH: 65
<212> TYPE: DNA
<213> ORGANISM: Homo sapiens

<400> SEQUENCE: 109
ctttctgtgc ctagttgaac ggcaagctcg gcatctgttg gttacaagat ccagacttgg    60
gccga                                                                65

<210> SEQ ID NO 110
<211> LENGTH: 65
<212> TYPE: DNA
<213> ORGANISM: Homo sapiens

<400> SEQUENCE: 110
tactgaacat tgggcccaca cggtcggatg acttggcgtg tctgaaactg aattctcgtt    60
gtgga                                                                65

<210> SEQ ID NO 111
<211> LENGTH: 65
<212> TYPE: DNA
<213> ORGANISM: Homo sapiens

<400> SEQUENCE: 111
aattgaagta aattctcatg tgtctgaaaa caagaatgga agctctaaca ctggagccaa    60
gcagg                                                                65

<210> SEQ ID NO 112
<211> LENGTH: 65
<212> TYPE: DNA
<213> ORGANISM: Homo sapiens

<400> SEQUENCE: 112
ggcccacgtc ctcaccacaa agggactcct gtgaaactgc tgccaaaaag ataccaataa    60
cacta                                                                65

<210> SEQ ID NO 113
<211> LENGTH: 65
<212> TYPE: DNA
<213> ORGANISM: Homo sapiens

<400> SEQUENCE: 113
agacggtgtg caccaacatc tacaagatcc tcctgctgca ggcgtacagg tttcacgcat    60
gtgtg                                                                65

<210> SEQ ID NO 114
<211> LENGTH: 65
<212> TYPE: DNA
<213> ORGANISM: Homo sapiens

<400> SEQUENCE: 114
tttttgtcta accctaactg agaagggcgt aggcgccgtg cttttgctcc ccgcgcgctg    60
ttttt                                                                65

<210> SEQ ID NO 115

```
<211> LENGTH: 65
<212> TYPE: DNA
<213> ORGANISM: Homo sapiens

<400> SEQUENCE: 115
ctccagttgg ccaccattag ctataatggc actttgtttg tgttgttgga aaaagtcaca    60
ttgcc                                                                65

<210> SEQ ID NO 116
<211> LENGTH: 65
<212> TYPE: DNA
<213> ORGANISM: Homo sapiens

<400> SEQUENCE: 116
atggcctgct attgcagaat accagcgtgc attgcaggag aacgtcgcta tggaacctgc    60
atcta                                                                65

<210> SEQ ID NO 117
<211> LENGTH: 65
<212> TYPE: DNA
<213> ORGANISM: Homo sapiens

<400> SEQUENCE: 117
acctgttaca gagggaaggc caagtgctgc aagtgagctg ggagtgacca gaagaaatga    60
cgcag                                                                65

<210> SEQ ID NO 118
<211> LENGTH: 65
<212> TYPE: DNA
<213> ORGANISM: Homo sapiens

<400> SEQUENCE: 118
tgacccaaag aaagagttgt ctcaactcct tggtacaggg ttcattcaaa cccccaagct    60
gtgag                                                                65

<210> SEQ ID NO 119
<211> LENGTH: 65
<212> TYPE: DNA
<213> ORGANISM: Homo sapiens

<400> SEQUENCE: 119
ggaacttgaa agctttggtt agccttgcct taggtaatca gcctagttta cactgtttcc    60
aggga                                                                65

<210> SEQ ID NO 120
<211> LENGTH: 65
<212> TYPE: DNA
<213> ORGANISM: Homo sapiens

<400> SEQUENCE: 120
atcaaggagt atatggacac tacactgggg cccttcatcc tgaacgtgac cagtggggcc    60
cttct                                                                65

<210> SEQ ID NO 121
<211> LENGTH: 65
<212> TYPE: DNA
<213> ORGANISM: Homo sapiens

<400> SEQUENCE: 121
caactttgtg agcttccgtg ttcaggaggc ccttcgtgtg gctcgcaccc accatgccaa    60
```

```
ccatg                                                              65

<210> SEQ ID NO 122
<211> LENGTH: 65
<212> TYPE: DNA
<213> ORGANISM: Homo sapiens

<400> SEQUENCE: 122
aaaatgcaga ctgtcatatc cagcgagtcc ctgacccttt ctgcgaatgt aacgagcaag    60
cagtc                                                              65

<210> SEQ ID NO 123
<211> LENGTH: 65
<212> TYPE: DNA
<213> ORGANISM: Homo sapiens

<400> SEQUENCE: 123
ctcacttagt cctggctcca gttctagagt tcctctttat tgcttttggt gaaagtttgg    60
ggttg                                                              65

<210> SEQ ID NO 124
<211> LENGTH: 65
<212> TYPE: DNA
<213> ORGANISM: Homo sapiens

<400> SEQUENCE: 124
acatcgtttt gttaagaagt taactgtatc gtagctcact actgccagag cggcaatgga    60
tgtac                                                              65

<210> SEQ ID NO 125
<211> LENGTH: 65
<212> TYPE: DNA
<213> ORGANISM: Homo sapiens

<400> SEQUENCE: 125
tccatcttga gccacagtca ctggattgac tttgctgtca aaactactga cagggagcag    60
ccccc                                                              65

<210> SEQ ID NO 126
<211> LENGTH: 65
<212> TYPE: DNA
<213> ORGANISM: Homo sapiens

<400> SEQUENCE: 126
gcaaaagagt gcaatgcaga ccttgaaagg catagtccgg ttcttgtcca agactgataa    60
gaggc                                                              65

<210> SEQ ID NO 127
<211> LENGTH: 65
<212> TYPE: DNA
<213> ORGANISM: Homo sapiens

<400> SEQUENCE: 127
acccagggac ctgagtgcct ctctgggaat agtcggggga acctatttgt gggcattgaa    60
aaagt                                                              65

<210> SEQ ID NO 128
<211> LENGTH: 65
<212> TYPE: DNA
```

<213> ORGANISM: Homo sapiens

<400> SEQUENCE: 128
ccctgtttaa tgattgacgt acttagcagc tatctctcag tgaactgtga gggtaaaggc    60
tatac    65

<210> SEQ ID NO 129
<211> LENGTH: 65
<212> TYPE: DNA
<213> ORGANISM: Homo sapiens

<400> SEQUENCE: 129
cctctcgttt gactggtaca tcaagacctc gcataaccac ctcctgatcg tgagcacagc    60
tgaga    65

<210> SEQ ID NO 130
<211> LENGTH: 65
<212> TYPE: DNA
<213> ORGANISM: Homo sapiens

<400> SEQUENCE: 130
attaaccaga aatccagtta ttttccgccc tcaaaatgac agccatggcc ggccgggtgc    60
ttctg    65

<210> SEQ ID NO 131
<211> LENGTH: 65
<212> TYPE: DNA
<213> ORGANISM: Mus musculus

<400> SEQUENCE: 131
aagtccaaga actatgagtt catgtggaat cctcacctgg gctacatcct cacatgccca    60
tccaa    65

<210> SEQ ID NO 132
<211> LENGTH: 65
<212> TYPE: DNA
<213> ORGANISM: Mus musculus

<400> SEQUENCE: 132
atgcccgtgg catctggcac aacgacaaca aaagcttcct tgtgtgggtg aacgaggagg    60
accac    65

<210> SEQ ID NO 133
<211> LENGTH: 65
<212> TYPE: DNA
<213> ORGANISM: Mus musculus

<400> SEQUENCE: 133
cttgaccttg ggaaacacaa tggtttagag ttgtttgtgt acatgttgaa aacctggtct    60
gtgct    65

<210> SEQ ID NO 134
<211> LENGTH: 65
<212> TYPE: DNA
<213> ORGANISM: Mus musculus

<400> SEQUENCE: 134
tggttgctag ctactgtacc tgcttggagg agctatgtga ggacaaatga acatgctgac    60
tgtat    65

<210> SEQ ID NO 135
<211> LENGTH: 65
<212> TYPE: DNA
<213> ORGANISM: Mus musculus

<400> SEQUENCE: 135
caaagcatct gagaattatc tccagaagtg atcacagtag caaggccaca caggacataa    60
aagca                                                                65

<210> SEQ ID NO 136
<211> LENGTH: 65
<212> TYPE: DNA
<213> ORGANISM: Mus musculus

<400> SEQUENCE: 136
ttgtctggca gccaacaaac aggtcatgcc ttgagtccta tgttagagcc ttgagtccta    60
tgtta                                                                65

<210> SEQ ID NO 137
<211> LENGTH: 65
<212> TYPE: DNA
<213> ORGANISM: Mus musculus

<400> SEQUENCE: 137
tggatctcct gaaggtgctg tcccagatga ttctgtttct gcttttcctt tatctgtcac    60
cgctg                                                                65

<210> SEQ ID NO 138
<211> LENGTH: 65
<212> TYPE: DNA
<213> ORGANISM: Mus musculus

<400> SEQUENCE: 138
gtcctggcac tgaagccagc atgagatcca tcattcttat gtcagctcaa gggtcaaaag    60
gactt                                                                65

<210> SEQ ID NO 139
<211> LENGTH: 65
<212> TYPE: DNA
<213> ORGANISM: Mus musculus

<400> SEQUENCE: 139
attggaaaat aacgtcaagt cctcccgtga agattttaca cgcaggcatc tcccacatta    60
gagat                                                                65

<210> SEQ ID NO 140
<211> LENGTH: 65
<212> TYPE: DNA
<213> ORGANISM: Mus musculus

<400> SEQUENCE: 140
tatgacccaa ccccttaaga aacccggtct gccaatgtct cattcgattt ctcaggattc    60
cacat                                                                65

<210> SEQ ID NO 141
<211> LENGTH: 65
<212> TYPE: DNA
<213> ORGANISM: Mus musculus

<400> SEQUENCE: 141
aaaactcgtg ggaaggccaa agtcaccggg cgttggaaat agatgaaact gttctcgtca    60
aagct    65

<210> SEQ ID NO 142
<211> LENGTH: 65
<212> TYPE: DNA
<213> ORGANISM: Mus musculus

<400> SEQUENCE: 142 ccttttgag aagtatgtca ttgctcaaga ctgccagcac agtgtacagc aaaagctatg    60
aataa    65

<210> SEQ ID NO 143
<211> LENGTH: 65
<212> TYPE: DNA
<213> ORGANISM: Mus musculus

<400> SEQUENCE: 143
atgcaccact ctacatgtgc ggcctcctgc ctgccaaatt cctagcgttg gttaccatga    60
atcaa    65

<210> SEQ ID NO 144
<211> LENGTH: 65
<212> TYPE: DNA
<213> ORGANISM: Mus musculus

<400> SEQUENCE: 144
cccttactgt gcatctgcct gacagtgttt gttctaaata cctcacttgc catgctttgt    60
gtggg    65

<210> SEQ ID NO 145
<211> LENGTH: 65
<212> TYPE: DNA
<213> ORGANISM: Mus musculus

<400> SEQUENCE: 145
tgagtttctg tcaccccgta gccccacctg ttgtccactg taggtgccat tccggtgctg    60
ttttt    65

<210> SEQ ID NO 146
<211> LENGTH: 65
<212> TYPE: DNA
<213> ORGANISM: Mus musculus

<400> SEQUENCE: 146
gaacaaacac taacgtaaat tgccccattg agtgcttcat gccgctagat gtgcaagctg    60
acaga    65

<210> SEQ ID NO 147
<211> LENGTH: 65
<212> TYPE: DNA
<213> ORGANISM: Mus musculus

<400> SEQUENCE: 147
ttgtagatgg caaggtctta tttcacgtca acaacggtgc cggaaggata acagccacct    60
accag    65

<210> SEQ ID NO 148
<211> LENGTH: 65
<212> TYPE: DNA
<213> ORGANISM: Mus musculus

<400> SEQUENCE: 148
cctcctctgt agttaaccag ccttctcctt cacctggtga cttcagattt aagagggtgg    60
cttct                                                                65

<210> SEQ ID NO 149
<211> LENGTH: 65
<212> TYPE: DNA
<213> ORGANISM: Mus musculus

<400> SEQUENCE: 149
gtgctttgtt cagcatgtgc tatggcagaa ccaaacagga gctatggatg acaccagtca    60
acgtc                                                                65

<210> SEQ ID NO 150
<211> LENGTH: 65
<212> TYPE: DNA
<213> ORGANISM: Mus musculus

<400> SEQUENCE: 150
cacctacaga attgtatcct atacttcaga cttacctcgg atcgtagtgg atcaaatcgt    60
gaaaa                                                                65

<210> SEQ ID NO 151
<211> LENGTH: 65
<212> TYPE: DNA
<213> ORGANISM: Mus musculus

<400> SEQUENCE: 151
gggcgcggct ccaaccgctg cataaatatt aaggtattca gttgcccta ctggaaggta     60 ttatg                                                                65

<210> SEQ ID NO 152
<211> LENGTH: 65
<212> TYPE: DNA
<213> ORGANISM: Mus musculus

<400> SEQUENCE: 152
ctctcggttt tcctcccacc gtgaagaaga ttgatgcagc tgtttttgaa aaggagaaga    60
agaaa                                                                65

<210> SEQ ID NO 153
<211> LENGTH: 65
<212> TYPE: DNA
<213> ORGANISM: Mus musculus

<400> SEQUENCE: 153
tttcctggta agtcagctct ggagagatag tgaactgatc atattctggc aggtgattca    60
gacaa                                                                65

<210> SEQ ID NO 154
<211> LENGTH: 65
<212> TYPE: DNA
<213> ORGANISM: Mus musculus

<400> SEQUENCE: 154

```
atcaacttca tgagatccag agtcatgtaa gagacatgtg agcactactt caaagaaggt    60
aaatg                                                                65

<210> SEQ ID NO 155
<211> LENGTH: 65
<212> TYPE: DNA
<213> ORGANISM: Mus musculus

<400> SEQUENCE: 155
ccatgtttgt taatccctct ctgctttcct tagcgagtaa cacttggtgc ttactgatgt    60
gtgaa                                                                65

<210> SEQ ID NO 156
<211> LENGTH: 65
<212> TYPE: DNA
<213> ORGANISM: Mus musculus

<400> SEQUENCE: 156
cctagttggc tgcctcccgc cactctgact aaaaggaatc ttaagagtgt acatttggag    60
gtgga                                                                65

<210> SEQ ID NO 157
<211> LENGTH: 65
<212> TYPE: DNA
<213> ORGANISM: Mus musculus

<400> SEQUENCE: 157
acttaacatt tggtagtgat aagaggagag gacagcccag cttcccaaat gactccacat    60
ctggc                                                                65

<210> SEQ ID NO 158
<211> LENGTH: 65
<212> TYPE: DNA
<213> ORGANISM: Mus musculus

<400> SEQUENCE: 158
gaaagccata gctattgtca ttccctgcat cttggcctta tgcctccttg tattggttta    60
cactg                                                                65

<210> SEQ ID NO 159
<211> LENGTH: 65
<212> TYPE: DNA
<213> ORGANISM: Mus musculus

<400> SEQUENCE: 159
taagtgtcag ggtcctcggg gagtcatgac aatgttaccg cctaacttgg agatgtagga    60
gctgt                                                                65

<210> SEQ ID NO 160
<211> LENGTH: 65
<212> TYPE: DNA
<213> ORGANISM: Mus musculus

<400> SEQUENCE: 160
gtggacagaa gatcctacac aagaaaggga aagtatactg gtacaaggac caggaacccc    60
tggag                                                                65

<210> SEQ ID NO 161
<211> LENGTH: 65
```

```
<212> TYPE: DNA
<213> ORGANISM: Mus musculus

<400> SEQUENCE: 161
tcaacagctg caggagctga ccctggttct gggggcggat gcaagtttgt gaccattctc    60
tactc                                                               65

<210> SEQ ID NO 162
<211> LENGTH: 65
<212> TYPE: DNA
<213> ORGANISM: Mus musculus

<400> SEQUENCE: 162
ctagggtcat caccctgaac tcaggattgc cccattcatt tggaagggat cttatgattc    60
ctgtc                                                               65

<210> SEQ ID NO 163
<211> LENGTH: 65
<212> TYPE: DNA
<213> ORGANISM: Mus musculus

<400> SEQUENCE: 163
gtgaagagtt tctcatcacg ggccgcctaa ggaacgggaa atttcacatc aatgcctgca    60
gcttc                                                               65

<210> SEQ ID NO 164
<211> LENGTH: 65
<212> TYPE: DNA
<213> ORGANISM: Mus musculus

<400> SEQUENCE: 164
cctccctccc ttactcccgt catgccagca actcgcaata tttcagatga cgtttacatg    60
gtagc                                                               65

<210> SEQ ID NO 165
<211> LENGTH: 65
<212> TYPE: DNA
<213> ORGANISM: Mus musculus

<400> SEQUENCE: 165
tagatctaag tcagctgttt gggttgagga ggagagaacc cgaggaaatg accatgctct    60
gggga                                                               65

<210> SEQ ID NO 166
<211> LENGTH: 65
<212> TYPE: DNA
<213> ORGANISM: Mus musculus

<400> SEQUENCE: 166
aaccacatcc ttggaagcat tctgaagacc aagccagttc tctgtggtcc tttgaccatc    60
accac                                                               65

<210> SEQ ID NO 167
<211> LENGTH: 65
<212> TYPE: DNA
<213> ORGANISM: Mus musculus

<400> SEQUENCE: 167
ctacagctca tggactctaa ttggatttcc tgaggcactc atatgccttc cttgtccttc    60
```

```
tgctt                                                             65

<210> SEQ ID NO 168
<211> LENGTH: 65
<212> TYPE: DNA
<213> ORGANISM: Mus musculus

<400> SEQUENCE: 168
aacaaggggc cattgcagga gtacatggct ccaggcttac tttatatact gcctgtattt    60
gtggc                                                             65

<210> SEQ ID NO 169
<211> LENGTH: 65
<212> TYPE: DNA
<213> ORGANISM: Mus musculus

<400> SEQUENCE: 169
cttaccattt tcaacgattg ttgacagggg tcctttgttt gaaataact ggggagagat    60 acggg                                                             65

<210> SEQ ID NO 170
<211> LENGTH: 65
<212> TYPE: DNA
<213> ORGANISM: Mus musculus

<400> SEQUENCE: 170
agcctcagcc cagtgaacca ccattgaggg cgtttaagat aatgttccag ccccgccttc    60
ctgtt                                                             65

<210> SEQ ID NO 171
<211> LENGTH: 65
<212> TYPE: DNA
<213> ORGANISM: Mus musculus

<400> SEQUENCE: 171
ccaccaccat tgtggtctcg gggaccaacc gtatttccac accattagac tgtgagctcc    60
ttcag                                                             65

<210> SEQ ID NO 172
<211> LENGTH: 65
<212> TYPE: DNA
<213> ORGANISM: Mus musculus

<400> SEQUENCE: 172
ctgaactgtg gaaaatgacc tttcctcagc ttgaagctac ttttaaaatc tgcgggtctg    60
gacca                                                             65

<210> SEQ ID NO 173
<211> LENGTH: 65
<212> TYPE: DNA
<213> ORGANISM: Mus musculus

<400> SEQUENCE: 173
ctggggaaaa atactgggtt tgtgaaaata ccccttctc cactagtggc atgctcattc    60
agctc                                                             65

<210> SEQ ID NO 174
<211> LENGTH: 65
<212> TYPE: DNA
<213> ORGANISM: Mus musculus
```

```
<400> SEQUENCE: 174
ctccaggcat ttaattgact taagtttctt atcggcctga cacccaagta catcattgta      60
gaacc                                                                  65

<210> SEQ ID NO 175
<211> LENGTH: 65
<212> TYPE: DNA
<213> ORGANISM: Mus musculus

<400> SEQUENCE: 175
acatttcaga aattggccca ccagatctac cagctaacag acaaagacaa ggacggcatg      60
gctcc                                                                  65

<210> SEQ ID NO 176
<211> LENGTH: 65
<212> TYPE: DNA
<213> ORGANISM: Mus musculus

<400> SEQUENCE: 176
gggcagggag gtgagttacg ctaatgctgg ccaggatgta taaagaaatt caagtgtgca      60
cacct                                                                  65

<210> SEQ ID NO 177
<211> LENGTH: 65
<212> TYPE: DNA
<213> ORGANISM: Mus musculus

<400> SEQUENCE: 177
aggacacaga ggttcctgag tttgacctca gcagatatgg cttcggtctg atgcagccag      60
aggaa                                                                  65

<210> SEQ ID NO 178
<211> LENGTH: 65
<212> TYPE: DNA
<213> ORGANISM: Mus musculus

<400> SEQUENCE: 178
ctttttatct ccctcatag cccagaacac tggttccatc gttcattgtc aggggccaga       60
aaaac                                                                  65

<210> SEQ ID NO 179
<211> LENGTH: 65
<212> TYPE: DNA
<213> ORGANISM: Mus musculus

<400> SEQUENCE: 179
atgtgggtta ctacacaaga ggccgaacat tccaagtagc agaagagagg gtctctcaac      60
tctgc                                                                  65

<210> SEQ ID NO 180
<211> LENGTH: 65
<212> TYPE: DNA
<213> ORGANISM: Mus musculus

<400> SEQUENCE: 180
cacctaaagc agcatgcatg ttactaacac cctgtttagc ccccgactct ctgcttatac      60
tcaga                                                                  65
```

```
<210> SEQ ID NO 181
<211> LENGTH: 65
<212> TYPE: DNA
<213> ORGANISM: Mus musculus

<400> SEQUENCE: 181 ctactttttgt tcccaatgtc agccaccatg ccttagcagc tgaacaatcg agcctcatgc      60
tcatg                                                                  65

<210> SEQ ID NO 182
<211> LENGTH: 65
<212> TYPE: DNA
<213> ORGANISM: Mus musculus

<400> SEQUENCE: 182
tgatcccttg ctgaatgcaa ggagctaacc agaaaagttc tgcttgacaa gtccccatcg      60
ttgaa                                                                  65

<210> SEQ ID NO 183
<211> LENGTH: 65
<212> TYPE: DNA
<213> ORGANISM: Mus musculus

<400> SEQUENCE: 183
tggtctcact accagttaaa gcaaaagact ttcaaacagt ggctctgtcc tccaagaagt      60
ggcaa                                                                  65

<210> SEQ ID NO 184
<211> LENGTH: 65
<212> TYPE: DNA
<213> ORGANISM: Mus musculus

<400> SEQUENCE: 184
aggaattcgg actagacatt ggccctgcct gcttcgtgta aactccctcc accccaatct      60
ggttc                                                                  65

<210> SEQ ID NO 185
<211> LENGTH: 65
<212> TYPE: DNA
<213> ORGANISM: Mus musculus

<400> SEQUENCE: 185
ggtggcagcc agtttgaata caacgtagaa ggggtgtcct ccaaggaaat ggcaactcag      60
ctcgc                                                                  65

<210> SEQ ID NO 186
<211> LENGTH: 65
<212> TYPE: DNA
<213> ORGANISM: Mus musculus

<400> SEQUENCE: 186
tcagggtttg caacactaac cacagactga atgactgact tcccgtacga cagccaaggc      60
ctttg                                                                  65

<210> SEQ ID NO 187
<211> LENGTH: 65
<212> TYPE: DNA
<213> ORGANISM: Mus musculus

<400> SEQUENCE: 187
```

```
atcctattct ccgcttagaa aggctttcca cccaattcca tcgcgccctc cctggagatg    60
cattt                                                                65

<210> SEQ ID NO 188
<211> LENGTH: 65
<212> TYPE: DNA
<213> ORGANISM: Mus musculus

<400> SEQUENCE: 188
gacatcagct tgaagtccag aaatctcaca gcagccacat gaagcacttg tcctatgaag    60
ggact                                                                65

<210> SEQ ID NO 189
<211> LENGTH: 65
<212> TYPE: DNA
<213> ORGANISM: Mus musculus

<400> SEQUENCE: 189
ttcctggcaa cggagatgaa cagcccctga ctgaaaaccc ccggaagtac gtcatgggtc    60
acttc                                                                65

<210> SEQ ID NO 190
<211> LENGTH: 65
<212> TYPE: DNA
<213> ORGANISM: Mus musculus

<400> SEQUENCE: 190
actctaagaa acatggtggc ccggcggatg aagagaggca tgttggagac ctgggcaatg    60
tgact                                                                65

<210> SEQ ID NO 191
<211> LENGTH: 65
<212> TYPE: DNA
<213> ORGANISM: Mus musculus

<400> SEQUENCE: 191
taataagatc tctttagatc agcgaagccc ctgtttatct gagaggcgcc gcctgccatg    60
agtac                                                                65

<210> SEQ ID NO 192
<211> LENGTH: 65
<212> TYPE: DNA
<213> ORGANISM: Mus musculus

<400> SEQUENCE: 192
aagttccatg ttcccgatca cctcctgcgg aggccccagg ttctgttttc atctgtttcc    60
catat                                                                65

<210> SEQ ID NO 193
<211> LENGTH: 65
<212> TYPE: DNA
<213> ORGANISM: Mus musculus

<400> SEQUENCE: 193
tcttctggac aagtacaacg ctgagaagcc taagaacgca attcacacct acacgcaggc    60
cggct                                                                65

<210> SEQ ID NO 194
```

```
<211> LENGTH: 65
<212> TYPE: DNA
<213> ORGANISM: Mus musculus

<400> SEQUENCE: 194
gcccaaagga aacacaagtt ctaggtccaa tggttctgct caaacctgaa catcattctt      60
ggggc                                                                 65

<210> SEQ ID NO 195
<211> LENGTH: 65
<212> TYPE: DNA
<213> ORGANISM: Mus musculus

<400> SEQUENCE: 195
tgaggctggt taggtaaagg agaaatgaca gtacatgcaa gacggaaggc tgaggcactc      60
gggag                                                                 65

<210> SEQ ID NO 196
<211> LENGTH: 65
<212> TYPE: DNA
<213> ORGANISM: Mus musculus

<400> SEQUENCE: 196
ccttcagtgt ctttgctaga tcaagtgcag acgctgcaca caatctctag ttcctctagt      60
tctgg                                                                 65

<210> SEQ ID NO 197
<211> LENGTH: 65
<212> TYPE: DNA
<213> ORGANISM: Mus musculus

<400> SEQUENCE: 197
ttggtaccca ataccggaa gccttgacga tggatttggt gacatgatcc ctctctcttt       60
ggttc                                                                 65

<210> SEQ ID NO 198
<211> LENGTH: 65
<212> TYPE: DNA
<213> ORGANISM: Mus musculus

<400> SEQUENCE: 198
aatcggtcac tccgtacgtt gtgactgcgt ggtctatggg accgaggcat ctcctcttga      60
ccttt                                                                 65

<210> SEQ ID NO 199
<211> LENGTH: 65
<212> TYPE: DNA
<213> ORGANISM: Mus musculus

<400> SEQUENCE: 199
ggcagactgg ctcacacaga ctttgatgaa atgtactcca ccttcagtgg tgttttcttg      60
taccc                                                                 65

<210> SEQ ID NO 200
<211> LENGTH: 65
<212> TYPE: DNA
<213> ORGANISM: Mus musculus

<400> SEQUENCE: 200
gacggtcgac ctccaattct tcggacctca tactccccac cttttacgtg ggcaacttct      60
``` ccatc 65

<210> SEQ ID NO 201
<211> LENGTH: 65
<212> TYPE: DNA
<213> ORGANISM: Mus musculus

<400> SEQUENCE: 201
acgccctgct tcactctgta aaggccaaca tatcaaatag ggacaatgtt gtgcatggcc    60
ttcac    65

<210> SEQ ID NO 202
<211> LENGTH: 65
<212> TYPE: DNA
<213> ORGANISM: Mus musculus

<400> SEQUENCE: 202
acttcgtcat gtcagcagcc cactgtgtga acggcctaaa tttccggtca gtgcaggtag    60
tgctg    65

<210> SEQ ID NO 203
<211> LENGTH: 65
<212> TYPE: DNA
<213> ORGANISM: Mus musculus

<400> SEQUENCE: 203
ccggcttcct accctactct aattttcact ggtgctggta acgtttgtct cattttgcgg    60
tactg    65

<210> SEQ ID NO 204
<211> LENGTH: 65
<212> TYPE: DNA
<213> ORGANISM: Mus musculus

<400> SEQUENCE: 204
aatctgttgt ctctcagatc ccgctgccct gctgctgtca cttagaacac gaaacaaagg    60
aatgt    65

<210> SEQ ID NO 205
<211> LENGTH: 65
<212> TYPE: DNA
<213> ORGANISM: Mus musculus

<400> SEQUENCE: 205
ggaacatcct taaatcctct gagcttgaca ggcatcctca cagcaggatt ttctaggtgg    60
tcagt    65

<210> SEQ ID NO 206
<211> LENGTH: 65
<212> TYPE: DNA
<213> ORGANISM: Mus musculus

<400> SEQUENCE: 206
cattaggcag cactctctag aacagaacct agctgtcaac gtgtggggga tgaattggtc    60
atagc    65

<210> SEQ ID NO 207
<211> LENGTH: 65
<212> TYPE: DNA

<213> ORGANISM: Mus musculus

<400> SEQUENCE: 207
ccccaactcc ggaaacggac tgtgaaacac aagttaccac ctatgcggat ttcatagaca    60
gcctt    65

<210> SEQ ID NO 208
<211> LENGTH: 65
<212> TYPE: DNA
<213> ORGANISM: Mus musculus

<400> SEQUENCE: 208
ggctgttgga atttacgcat aaagcagact gcatagatcc aatattgact gacccaagca    60
tgtta    65

<210> SEQ ID NO 209
<211> LENGTH: 65
<212> TYPE: DNA
<213> ORGANISM: Mus musculus

<400> SEQUENCE: 209
ctgaacctct gctccccacg ggagccgtga ctgtaatcgc cctacgggtc attgagagaa    60
ataaa    65

<210> SEQ ID NO 210
<211> LENGTH: 65
<212> TYPE: DNA
<213> ORGANISM: Mus musculus

<400> SEQUENCE: 210
atctactcgg caaacctagt gcgttatgcc taagcatatc agtttgtgga cattcctcac    60
tgtgg    65

<210> SEQ ID NO 211
<211> LENGTH: 65
<212> TYPE: DNA
<213> ORGANISM: Mus musculus

<400> SEQUENCE: 211
tgaacagatg ggtgtgtggc tgatacagca cctgcctgaa gcataatgct tgctctctgt    60
cagct    65

<210> SEQ ID NO 212
<211> LENGTH: 65
<212> TYPE: DNA
<213> ORGANISM: Mus musculus

<400> SEQUENCE: 212
atggtctctg gggacaccca gctagggcct tccccaactc cttatccagc tgaacttgga    60
ttctt    65

<210> SEQ ID NO 213
<211> LENGTH: 65
<212> TYPE: DNA
<213> ORGANISM: Mus musculus

<400> SEQUENCE: 213
ctccttccat aggctaaggc tcaaggcctc ttgtctttag tcaggactgt cctcatcatg    60
ttaca    65

<210> SEQ ID NO 214
<211> LENGTH: 65
<212> TYPE: DNA
<213> ORGANISM: Mus musculus

<400> SEQUENCE: 214
tctgcagttg tggtcgtgtt aaaccgatct tcggaggatg tccctcttac catcagtgat    60
cctga    65

<210> SEQ ID NO 215
<211> LENGTH: 65
<212> TYPE: DNA
<213> ORGANISM: Mus musculus

<400> SEQUENCE: 215
gtgcttcttg ggagagaaat tgtctatgt ttctagtgcc tttcttgtct tgattgtatg    60
gtcgg    65

<210> SEQ ID NO 216
<211> LENGTH: 65
<212> TYPE: DNA
<213> ORGANISM: Mus musculus

<400> SEQUENCE: 216
agcgccaaga cctattctta cctgttttcc caccctccac ggatgcctat ctaccccaaa    60
tggat    65

<210> SEQ ID NO 217
<211> LENGTH: 65
<212> TYPE: DNA
<213> ORGANISM: Mus musculus

<400> SEQUENCE: 217
cccatataag ctggtgccgt aggcgaatct aactgcttcc ctgttcattt cttgtgcctt    60
ttgca    65

<210> SEQ ID NO 218
<211> LENGTH: 65
<212> TYPE: DNA
<213> ORGANISM: Mus musculus

<400> SEQUENCE: 218
ctctataaat tccagatgcc tccgaaaaat agggatgctc taaacgtgat ttccgagctc    60
tacac    65

<210> SEQ ID NO 219
<211> LENGTH: 65
<212> TYPE: DNA
<213> ORGANISM: Mus musculus

<400> SEQUENCE: 219
ttcctgtaca ttgtggcttt cgcagccaag gtgctgactg gtcagatgcg tgaactggaa    60
gactt    65

<210> SEQ ID NO 220
<211> LENGTH: 65
<212> TYPE: DNA
<213> ORGANISM: Mus musculus

<400> SEQUENCE: 220
ctgtccgcgg aatcgtatcc acatatggca ggccatagct ctcagaaagt ctgacttgta    60
aatcc                                                                65

<210> SEQ ID NO 221
<211> LENGTH: 65
<212> TYPE: DNA
<213> ORGANISM: Mus musculus

<400> SEQUENCE: 221
ctctctggtt tactaagcta gccttagtgg aatttctttg gtctgtctct ggtaccccac    60
gtgat                                                                65

<210> SEQ ID NO 222
<211> LENGTH: 65
<212> TYPE: DNA
<213> ORGANISM: Mus musculus

<400> SEQUENCE: 222
gtggtcaggg aggatatgag tccatatttta cagcaaagca ccttgatttt aatcaatctc    60
acagc                                                                65

<210> SEQ ID NO 223
<211> LENGTH: 65
<212> TYPE: DNA
<213> ORGANISM: Mus musculus

<400> SEQUENCE: 223
gtggtcaggg aggatatgag tccatatttta cagcaaagca ccttgatttt aatcaatctc    60
acagc                                                                65

<210> SEQ ID NO 224
<211> LENGTH: 65
<212> TYPE: DNA
<213> ORGANISM: Mus musculus

<400> SEQUENCE: 224
atccagctca ggtggcggtg gcgttaagtc ctctggcagt tctaccgtga agtttgtttc    60
cacca                                                                65

<210> SEQ ID NO 225
<211> LENGTH: 65
<212> TYPE: DNA
<213> ORGANISM: Mus musculus

<400> SEQUENCE: 225
tcatctgtgg catctaagac tggcttcggc tctgggggtc aaagttctgg aggaagaggg    60
tctta                                                                65

<210> SEQ ID NO 226
<211> LENGTH: 65
<212> TYPE: DNA
<213> ORGANISM: Mus musculus

<400> SEQUENCE: 226
tcttctgggg gcttcggcag cagaagtctt tacaacctcg ggggtcacaa gagtatctcc    60
atgag                                                                65

```
<210> SEQ ID NO 227
<211> LENGTH: 65
<212> TYPE: DNA
<213> ORGANISM: Mus musculus

<400> SEQUENCE: 227
acctatgcat cagctaaatg gacacacagc ggaggggaaa tgttcgttgc cttaaatcaa      60
aaggg                                                                 65

<210> SEQ ID NO 228
<211> LENGTH: 65
<212> TYPE: DNA
<213> ORGANISM: Mus musculus

<400> SEQUENCE: 228
acaactggta gttttgcaat tgtcttctca aggtaagagg atggacacaa aggggccgta      60
cctcc                                                                 65

<210> SEQ ID NO 229
<211> LENGTH: 65
<212> TYPE: DNA
<213> ORGANISM: Mus musculus

<400> SEQUENCE: 229
agactgaaga atcgtggtgt agactgtggc caaacagagc aatggccact gtcagaaagt      60
ccatc                                                                 65

<210> SEQ ID NO 230
<211> LENGTH: 65
<212> TYPE: DNA
<213> ORGANISM: Mus musculus

<400> SEQUENCE: 230 cccccttta gtccaggagg gatttgcact agtgagtacc aggattctaa taaaaggctc       60
ttttc                                                                 65

<210> SEQ ID NO 231
<211> LENGTH: 65
<212> TYPE: DNA
<213> ORGANISM: Mus musculus

<400> SEQUENCE: 231
gcacaaggac tggggatgaa ataagagtgg atccaaggac cgtatcccaa aagatgggcc      60
attat                                                                 65

<210> SEQ ID NO 232
<211> LENGTH: 65
<212> TYPE: DNA
<213> ORGANISM: Mus musculus

<400> SEQUENCE: 232
aaccaggctg atgatggtag agtgctacag acttggtact ccagtttcca cggctaatca     60
ctgct                                                                 65

<210> SEQ ID NO 233
<211> LENGTH: 65
<212> TYPE: DNA
<213> ORGANISM: Mus musculus

<400> SEQUENCE: 233
```

```
tgagttggac tgcagtcttg cctaggtgat ttttgtctac cgttcgtgtt ccgaaagccc    60
aaggt                                                                65

<210> SEQ ID NO 234
<211> LENGTH: 65
<212> TYPE: DNA
<213> ORGANISM: Mus musculus

<400> SEQUENCE: 234
cttcagggaa tatgaaggag aaacagaaga agaaggagg cttcgacaag aaaacgggac    60
tgtgc                                                                65

<210> SEQ ID NO 235
<211> LENGTH: 65
<212> TYPE: DNA
<213> ORGANISM: Mus musculus

<400> SEQUENCE: 235
ccagttagga ccattactgc cagaggagaa aagtattaag tagctcattt ccctacctaa    60
aagat                                                                65

<210> SEQ ID NO 236
<211> LENGTH: 65
<212> TYPE: DNA
<213> ORGANISM: Mus musculus

<400> SEQUENCE: 236
catagcctct aaccaccata gcctctaacc acccaggcaa gaagcagcct tccctaactt    60
ctaat                                                                65

<210> SEQ ID NO 237
<211> LENGTH: 65
<212> TYPE: DNA
<213> ORGANISM: Mus musculus

<400> SEQUENCE: 237
catatggctg acttcgcttt ggcagatctg ctactcattc ttgggacctc cctggaggtg    60
gagcc                                                                65

<210> SEQ ID NO 238
<211> LENGTH: 65
<212> TYPE: DNA
<213> ORGANISM: Mus musculus

<400> SEQUENCE: 238
tactctggtt acaggttcat cctcaccgcc cgcgagcaaa agctcccaat agccattctg    60
aatat                                                                65

<210> SEQ ID NO 239
<211> LENGTH: 65
<212> TYPE: DNA
<213> ORGANISM: Mus musculus

<400> SEQUENCE: 239
acgccgacac gtggaaatga agatgagcac cttcatcgag gaatttaaag ctacatttaa    60
gaata                                                                65

<210> SEQ ID NO 240
<211> LENGTH: 65
```

```
<212> TYPE: DNA
<213> ORGANISM: Mus musculus

<400> SEQUENCE: 240
gaagaagcag tcccccatgt aaccatgaga gagccagaga gcttttttgca ccatgcattt    60 ttacg                                                                65

<210> SEQ ID NO 241
<211> LENGTH: 65
<212> TYPE: DNA
<213> ORGANISM: Mus musculus

<400> SEQUENCE: 241
gtgattcagc ttccctttga ccagcgtgtt aggaagaacc tcacattctt tctgggcatc    60
atctc                                                                65

<210> SEQ ID NO 242
<211> LENGTH: 65
<212> TYPE: DNA
<213> ORGANISM: Mus musculus

<400> SEQUENCE: 242
attattcaat ccgctataga catctgtgca ctgtgcatct ctccaggcat gaagaaaacc    60
aggta                                                                65

<210> SEQ ID NO 243
<211> LENGTH: 65
<212> TYPE: DNA
<213> ORGANISM: Mus musculus

<400> SEQUENCE: 243
gaacaagacg agcatgagta ctgaggccac tgatgctggt gcctgatgac cacttctcaa    60
taaat                                                                65

<210> SEQ ID NO 244
<211> LENGTH: 65
<212> TYPE: DNA
<213> ORGANISM: Mus musculus

<400> SEQUENCE: 244
ctcttccaca gtcttagcag tcagttctat gacaccccat ctgcaacctt agcaatagaa    60
actcc                                                                65

<210> SEQ ID NO 245
<211> LENGTH: 65
<212> TYPE: DNA
<213> ORGANISM: Mus musculus

<400> SEQUENCE: 245
tgaatgtacg gtatcatcgt gtgtgaacta ctgctgtaaa atgtgctgat cctcctgccc    60
caaac                                                                65

<210> SEQ ID NO 246
<211> LENGTH: 65
<212> TYPE: DNA
<213> ORGANISM: Mus musculus

<400> SEQUENCE: 246
cccctcatga taatgaaacc cacggagaaa gcagaagtac cgacaggggt tatcataggc    60
``` agcat                                                              65

<210> SEQ ID NO 247
<211> LENGTH: 65
<212> TYPE: DNA
<213> ORGANISM: Mus musculus

<400> SEQUENCE: 247
caagcactag aagtgggcta actcattcag tctttgcaat ggacatgcag ggaagctgag    60
cctttt                                                             65

<210> SEQ ID NO 248
<211> LENGTH: 65
<212> TYPE: DNA
<213> ORGANISM: Mus musculus

<400> SEQUENCE: 248
acctgccaat acctcaagaa ttacctaact cagctgctgg ttccctacat agtcaacgtg    60
tcctg                                                              65

<210> SEQ ID NO 249
<211> LENGTH: 65
<212> TYPE: DNA
<213> ORGANISM: Mus musculus

<400> SEQUENCE: 249
tgaggccttt tctctctggg aaccaacaag aaatacatta tctttgcccc cgttctgaca    60
agtgt                                                              65

<210> SEQ ID NO 250
<211> LENGTH: 65
<212> TYPE: DNA
<213> ORGANISM: Mus musculus

<400> SEQUENCE: 250
atttcaggac acgtggagaa ccgctcatgt agagcagtcc cacccctaat tttcatacca    60
ttcac                                                              65

<210> SEQ ID NO 251
<211> LENGTH: 65
<212> TYPE: DNA
<213> ORGANISM: Mus musculus

<400> SEQUENCE: 251 ccttttttgag aagtatgtca ttgctcaaga ctgccagcac agtgtacagc aaaagctatg   60
aataa                                                              65

<210> SEQ ID NO 252
<211> LENGTH: 65
<212> TYPE: DNA
<213> ORGANISM: Mus musculus

<400> SEQUENCE: 252
atatatcatg gagggtgccg tatccaagtc tctgtctgtg ccaaaaccaa gccaaagcgc    60
ctcta                                                              65

<210> SEQ ID NO 253
<211> LENGTH: 65
<212> TYPE: DNA
<213> ORGANISM: Mus musculus

<400> SEQUENCE: 253
ttaaggtgga atcaagttta cagacaatca cctgaatgct gactcattcc ttgttcacaa    60
ccact    65

<210> SEQ ID NO 254
<211> LENGTH: 65
<212> TYPE: DNA
<213> ORGANISM: Mus musculus

<400> SEQUENCE: 254
ctccccagag ctcactgtga cagtaacagt ttggaatgag ggtgaggaca gctatggaac    60
cttaa    65

<210> SEQ ID NO 255
<211> LENGTH: 65
<212> TYPE: DNA
<213> ORGANISM: Mus musculus

<400> SEQUENCE: 255
tctgctagcc tgccttgtcc ctctgagaga atctttgaaa taaactcgga gaaactgcca    60
tctca    65

<210> SEQ ID NO 256
<211> LENGTH: 65
<212> TYPE: DNA
<213> ORGANISM: Mus musculus

<400> SEQUENCE: 256
cttcctagct gttgggggtc tctccttagg gatattaaag ggtatatgtt tagaatctat    60
tccac    65

<210> SEQ ID NO 257
<211> LENGTH: 65
<212> TYPE: DNA
<213> ORGANISM: Mus musculus

<400> SEQUENCE: 257
ctgccaagga tccaaaagcc tgctcggttt ctttccgcca ttatatcaag tctgccaggg    60
tttcc    65

<210> SEQ ID NO 258
<211> LENGTH: 65
<212> TYPE: DNA
<213> ORGANISM: Homo sapiens

<400> SEQUENCE: 258
agtcctctcc caagtccaca caggggaggt gatagcattg ctttcgtgta aattatgtaa    60
tgcaa    65

<210> SEQ ID NO 259
<211> LENGTH: 65
<212> TYPE: DNA
<213> ORGANISM: Homo sapiens

<400> SEQUENCE: 259
gagacaattg ccaagtgcat tgcggaccta aagctgctgg caaagaaggc tcaagcacag    60
ccagt    65

```
<210> SEQ ID NO 260
<211> LENGTH: 65
<212> TYPE: DNA
<213> ORGANISM: Homo sapiens

<400> SEQUENCE: 260
agttgccatg tagacccctt gaagagggga ggggcctagg gagccgcacc ttgtcatgta    60
ccatc                                                               65

<210> SEQ ID NO 261
<211> LENGTH: 65
<212> TYPE: DNA
<213> ORGANISM: Homo sapiens

<400> SEQUENCE: 261
gagcctttca tgaggaaaaa caaaagacat ggtacgcatt ccagggctga atactattgc    60
ttggc                                                               65

<210> SEQ ID NO 262
<211> LENGTH: 65
<212> TYPE: DNA
<213> ORGANISM: Homo sapiens

<400> SEQUENCE: 262
caacacagag tactgactct gcctggttcc tgagagaggc tcctaagtca cagacctcag    60
tcttt                                                               65

<210> SEQ ID NO 263
<211> LENGTH: 65
<212> TYPE: DNA
<213> ORGANISM: Homo sapiens

<400> SEQUENCE: 263
aacaacggca agaagctcat gactgtgcgc atcgtcaagc atgccttcga gatcatacac    60
ctgct                                                               65

<210> SEQ ID NO 264
<211> LENGTH: 65
<212> TYPE: DNA
<213> ORGANISM: Homo sapiens

<400> SEQUENCE: 264
tgcagcatgt catgctccca gaatttcagc ttcagcttaa ctgacagacg ttaaagcttt    60
ctggt                                                               65

<210> SEQ ID NO 265
<211> LENGTH: 65
<212> TYPE: DNA
<213> ORGANISM: Homo sapiens

<400> SEQUENCE: 265
tggaaaacag cccgtttact tgagcaagac tgataccacc tgcgtgtccc ttcctccccg    60
agtca                                                               65

<210> SEQ ID NO 266
<211> LENGTH: 60
<212> TYPE: DNA
<213> ORGANISM: Homo sapiens

<400> SEQUENCE: 266
```

```
gtcggacgag gatatgggat ttggtctctt tgactaatca ccaaaaagca accaacttag    60
```

<210> SEQ ID NO 267
<211> LENGTH: 65
<212> TYPE: DNA
<213> ORGANISM: Mus musculus

<400> SEQUENCE: 267

```
ccatcgtgca ccgcaagtgc ttctaggcgg actgttactg agctgcgttt tacacccttt    60
cttg                                                                 65
```

<210> SEQ ID NO 268
<211> LENGTH: 65
<212> TYPE: DNA
<213> ORGANISM: Mus musculus

<400> SEQUENCE: 268

```
gggctgccat ttgcagtggc aaagtggaga ttgttgccat caacgacccc ttcattgacc    60
tcaac                                                                65
```

<210> SEQ ID NO 269
<211> LENGTH: 65
<212> TYPE: DNA
<213> ORGANISM: Mus musculus

<400> SEQUENCE: 269

```
ggtcctccat ttcccaggtg atccaaatgc cctttggcc cctgcgggta ccacatgtat     60
gtggt                                                                65
```

<210> SEQ ID NO 270
<211> LENGTH: 65
<212> TYPE: DNA
<213> ORGANISM: Mus musculus

<400> SEQUENCE: 270

```
ttctgcctga gaaaggaagt gagctgtaaa ggctgagctc tctctctgac gtatgtagcc    60
tctgg                                                                65
```

<210> SEQ ID NO 271
<211> LENGTH: 65
<212> TYPE: DNA
<213> ORGANISM: Mus musculus

<400> SEQUENCE: 271

```
atcagatgag gatatgggat tcggtctctt cgactaatcc cgccaaagca accaagtcag    60
cctgc                                                                65
```

<210> SEQ ID NO 272
<211> LENGTH: 65
<212> TYPE: DNA
<213> ORGANISM: Saccharomyces cerevisiae

<400> SEQUENCE: 272

```
gcatgttgac tcgtcctctg aaccaaagca cggacaggat taagagtgat ccaactttca    60
agtcg                                                                65
```

<210> SEQ ID NO 273
<211> LENGTH: 65
<212> TYPE: DNA

```
<213> ORGANISM: Escherichia coli

<400> SEQUENCE: 273
gtgtcggcat aagccgaaga tatcggtaga gttatattga gcagatcccc cggtgaagga    60
tttaa                                                                65
```

PROBE OR PROBE SET FOR EVALUATING INFLUENCE OF ULTRAVIOLET RAY ON SKIN AND NUCLEIC ACID MICROARRAY

TECHNICAL FIELD

The present invention relates to a probe or a probe set which can evaluate the skin condition such as wrinkle or elasticity, specifically the influence of ultraviolet ray on the skin, and a nucleic acid microarray, and a method of evaluating the influence of ultraviolet ray on the skin using the same, and the like.

BACKGROUND ART

The skin is the greatest and most visible organ of the body of animals including human, and mainly consists of the epithelium and the dermis, and has several accessory structures such as sweat glands, sebaceous glands and hair follicles.

In addition, the skin is an organ that is most frequently exposed to environmental stresses, hazards and pathogens among the tissues of the body. Therefore, the skin has many functions, for example, a protection-barrier functions to external invasions (for example, heat, chemical agents and bacteria), a heat-regulation function, a dehydration-prevention function, and further a sensory function. Accordingly, maintenance and establishment of the skin health is important for the health of the animal.

As one of the methods of evaluating the skin condition or evaluating ingredients improving the skin condition, a method is known so far in which the aging state or inflammation state of the skin is evaluated by measuring the gene expression level (Patent Documents 1 and 2). Particularly with respect to the wrinkle and the aging state, known is a method of evaluating certain proteins and expression of genes and the like on the skin irradiated with ultraviolet ray, and, (Patent Documents 3 and 4).

CITATION LIST

Patent Document

Patent Document 1: JP 2010-115131 A
Patent Document 2: JP 2010-172240 A
Patent Document 3: JP 2011-178747 A
Patent Document 4: JP 2005-520483 W

DISCLOSURE OF THE INVENTION

Problem to be Solved by the Invention

However, these evaluation methods can measure only single symptom or state, respectively, and particularly are not a method that can objectively evaluate the influence of ultraviolet ray on the skin at the gene expression level.

Accordingly, a main object of the invention is to provide a probe or a probe set and a nucleic acid microarray which is loaded with the probe or the probe set, which can evaluate what the skin condition or a skin cell condition is, and what kind of influence of an external stimulation (particularly ultraviolet ray) to the skin condition, such as elasticity and wrinkles,

Means for Solving Problem

The inventors conducted thorough investigations so as to solve such problems described above, and as a result, the inventors found that the object described above can be achieved by selecting certain genes focusing on genes related to the constitution of the skin and using nucleic acids constituting the gene (or a portion thereof) as a probe, thus completing the invention.

Specifically, the present invention is as described below.

(1) A probe or a probe set for evaluating the influence of ultraviolet ray on the skin, which comprises nucleic acids of (a), (b) or (c) described below or a portion thereof.

(a) Nucleic acids comprising a base sequence constituting at least one kind of gene selected from the group consisting of GBA, GLB1, CAT, OLFM1, ASAH1, MMP14, MMP17 and COL18A1

(b) Nucleic acids comprising a base sequence complementary to the nucleic acids of aforesaid (a)

(c) Nucleic acids which hybridize with nucleic acids comprising a base sequence complementary to the nucleic acids of aforesaid (a) or (b) under stringent conditions, and can detect a skin constitution-related gene Examples of the nucleic acids of (a) in the probe set of (1) described above include those composed of the nucleic acids of (i) and (ii) described below.

(i) Nucleic acids comprising a base sequence constituting at least one kind of gene selected from the group consisting of GBA, GLB1, CAT, OLFM1 and ASAH1

(ii) Nucleic acids comprising a base sequence constituting at least one kind of gene selected from the group consisting of MMP14, MMP17 and COL18A1

In addition, similarly, examples of the nucleic acids of (a) include nucleic acids comprising a base sequence constituting each gene of GBA, GLB1, CAT, OLFM1 and ASAH1; nucleic acids comprising a base sequence constituting each gene of MMP14, MMP17 and COL18A1; and nucleic acids comprising a base sequence constituting each gene of MMP14, MMP17, COL18A1, GBA, GLB1, CAT, OLFM1 and ASAH1.

(2) A probe or a probe set for evaluating the influence of ultraviolet ray on the skin, which comprises nucleic acids of (α), (β), (γ) or (δ) described below.

(α) Nucleic acids comprising at least one kind of base sequence among base sequences shown in SEQ ID NOS: 27, 30, 58, 63, 70, 84, 85 and 112

(β) Nucleic acids comprising a base sequence complementary to the nucleic acids of aforesaid (a)

(γ) Nucleic acids comprising a base sequence having a homology of 70% or higher with respect to the base sequence of the nucleic acids of aforesaid (α) or (β), and can detect a skin constitution-related gene (δ) Nucleic acids comprising a base sequence of which one to several bases are added, deleted or substituted in the base sequence of the nucleic acids of aforesaid (α), (β) or (γ), and can detect a skin constitution-related gene Examples of the nucleic acids of (α) in the probe set of (2) described above include nucleic acids comprising base sequences shown in SEQ ID NOS: 27, 30, 58, 63, 70, 84, 85 and 112.

(3) A probe set for evaluating the influence of ultraviolet ray on the skin, which comprises nucleic acids of (i) and/or (ii) described below.

(i) Nucleic acids comprising base sequences shown in SEQ ID NOS: 1 to 130

(ii) Nucleic acids comprising base sequences shown in SEQ ID NOS: 131 to 257

(4) A nucleic acid microarray for evaluating the influence of ultraviolet ray on the skin, which comprises the probe or the probe set of any one of (1) to (3) described above.

(5) A method of evaluating the influence of ultraviolet ray on the skin, which comprises a process of irradiating a target object with ultraviolet ray, and then measuring the gene-expression amount using the probe or the probe set of any one of (1) to (3) described above.

(6) A method of evaluating the influence of ultraviolet ray on the skin, which comprises a process of irradiating a target object with ultraviolet ray, and then measuring the gene-expression amount using the nucleic acid microarray of (4) described above.

(7) A method of screening a compound that is useful in a skin disease remedy or a cosmetic using the probe or the probe set of any one of (1) to (3) described above.

(8) A method of screening a compound that is useful in a skin disease remedy or a cosmetic using the nucleic acid microarray of (4) described above.

Effect of the Invention

According to the invention, it is possible to provide a probe or a probe set which can objectively evaluate the influence of external stimulation, particularly ultraviolet ray on the skin at the gene expression level, and a nucleic acid microarray which is loaded with the probe or the probe set.

In addition, according to the invention, it is possible to provide a method of evaluating the influence of ultraviolet ray on the skin of a test subject, and a method of effectively screening a substance (compound and the like) that is useful as an active ingredient of a skin disease remedy (percutaneous absorption-type formulation and the like) or a cosmetic using the probe or the probe set and the nucleic acid microarray.

MODE(S) FOR CARRYING OUT THE INVENTION

Figure 1:
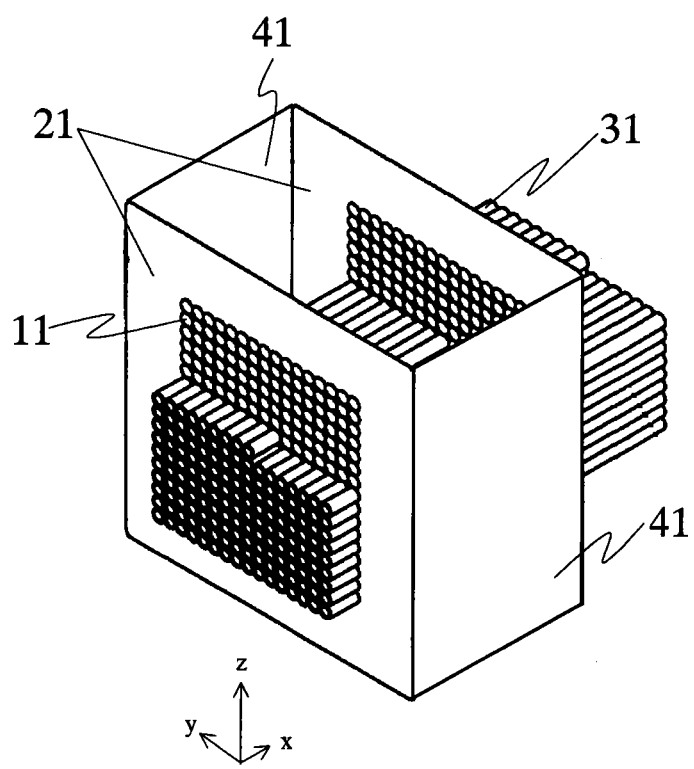
FIG. 1 is a schematic diagram illustrating a sequence fixing apparatus for manufacturing a hollow fiber bundle (hollow fiber array).
Figure 2A:
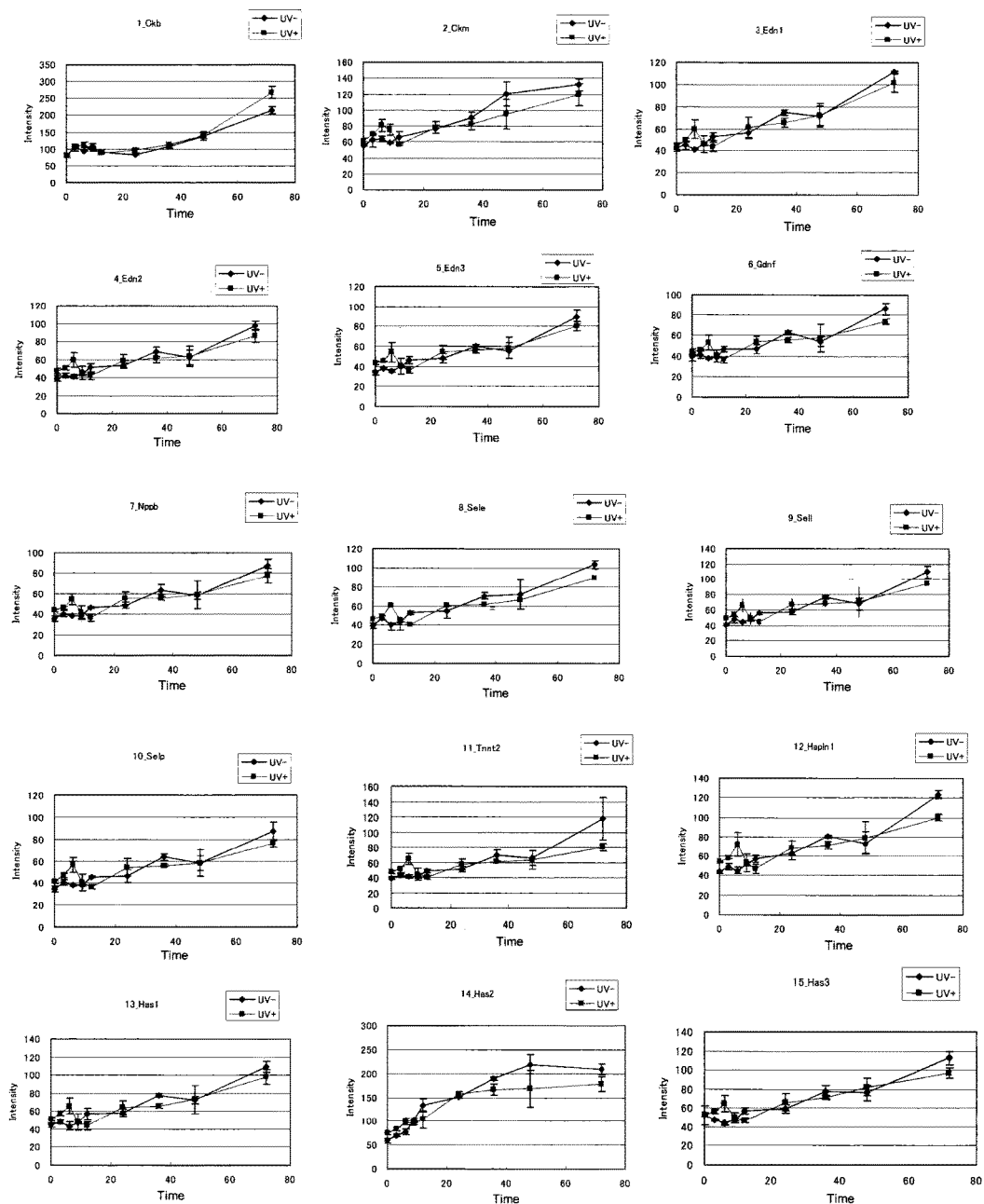
FIG. 2 (FIGS. 2A to 2H) is a diagram illustrating the change of the gene-expression amount associated with irradiation of UVB (ultraviolet ray B wave) on a keratinocyte. The vertical axis in all of the graphs in FIG. 2 represents the fluorescence intensity (Intensity), and the horizontal axis represents the time (h), and ♦ (UV−) represents the case of the absence of UVB irradiation, and ■ (UV+) represents the case of the presence of UVB irradiation.
Figure 2B:
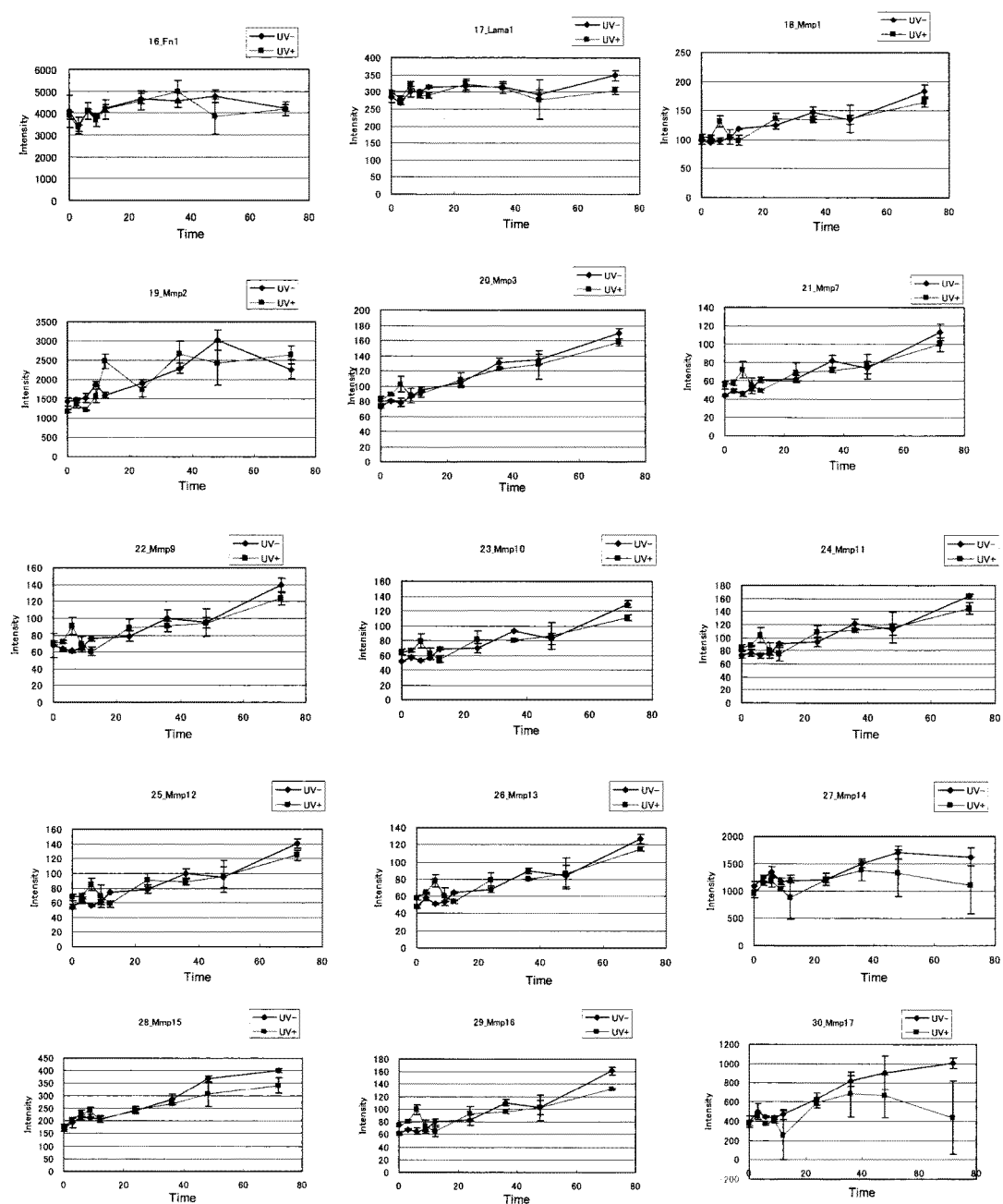
Figure 2C:
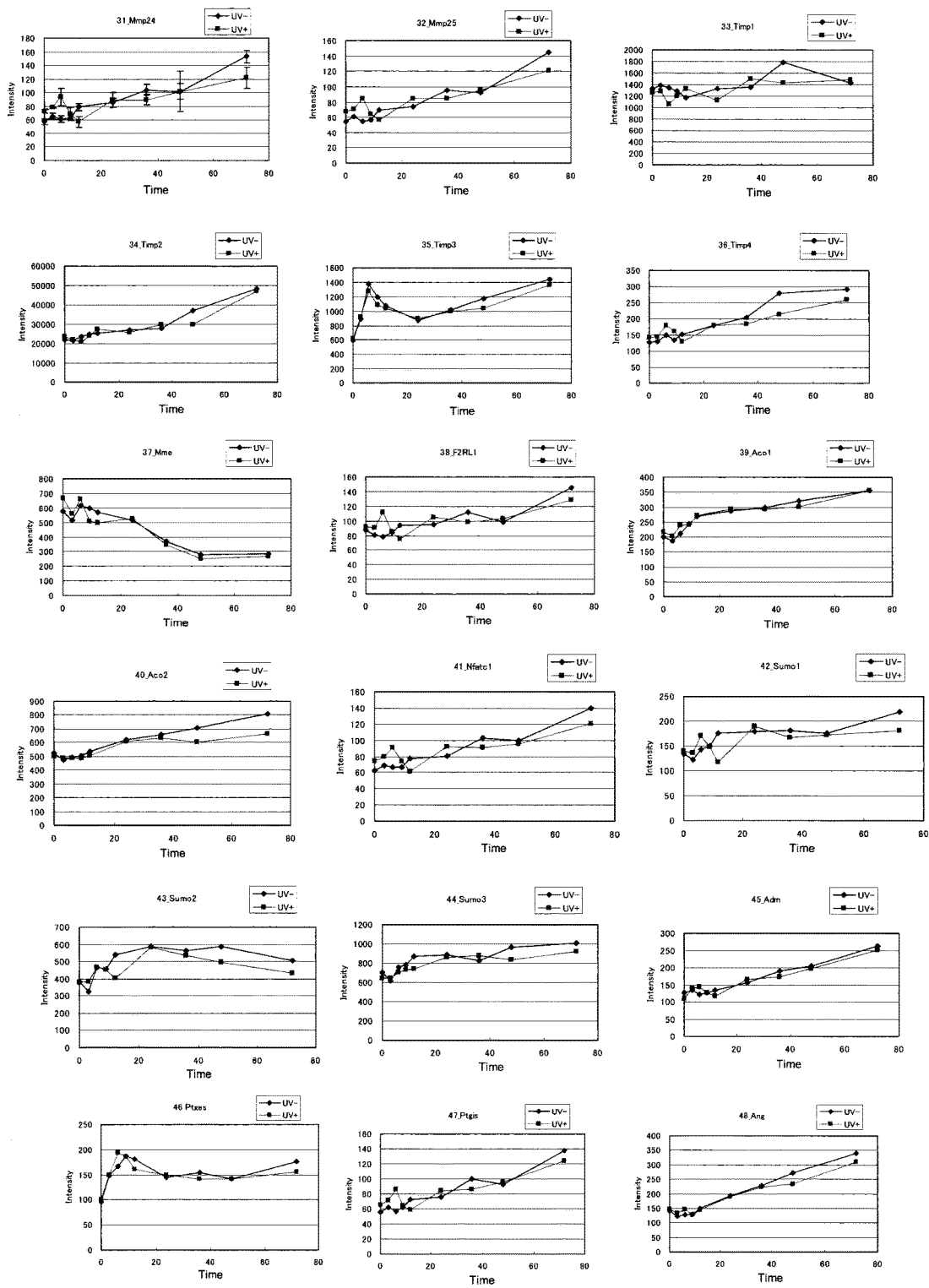
Figure 2D:
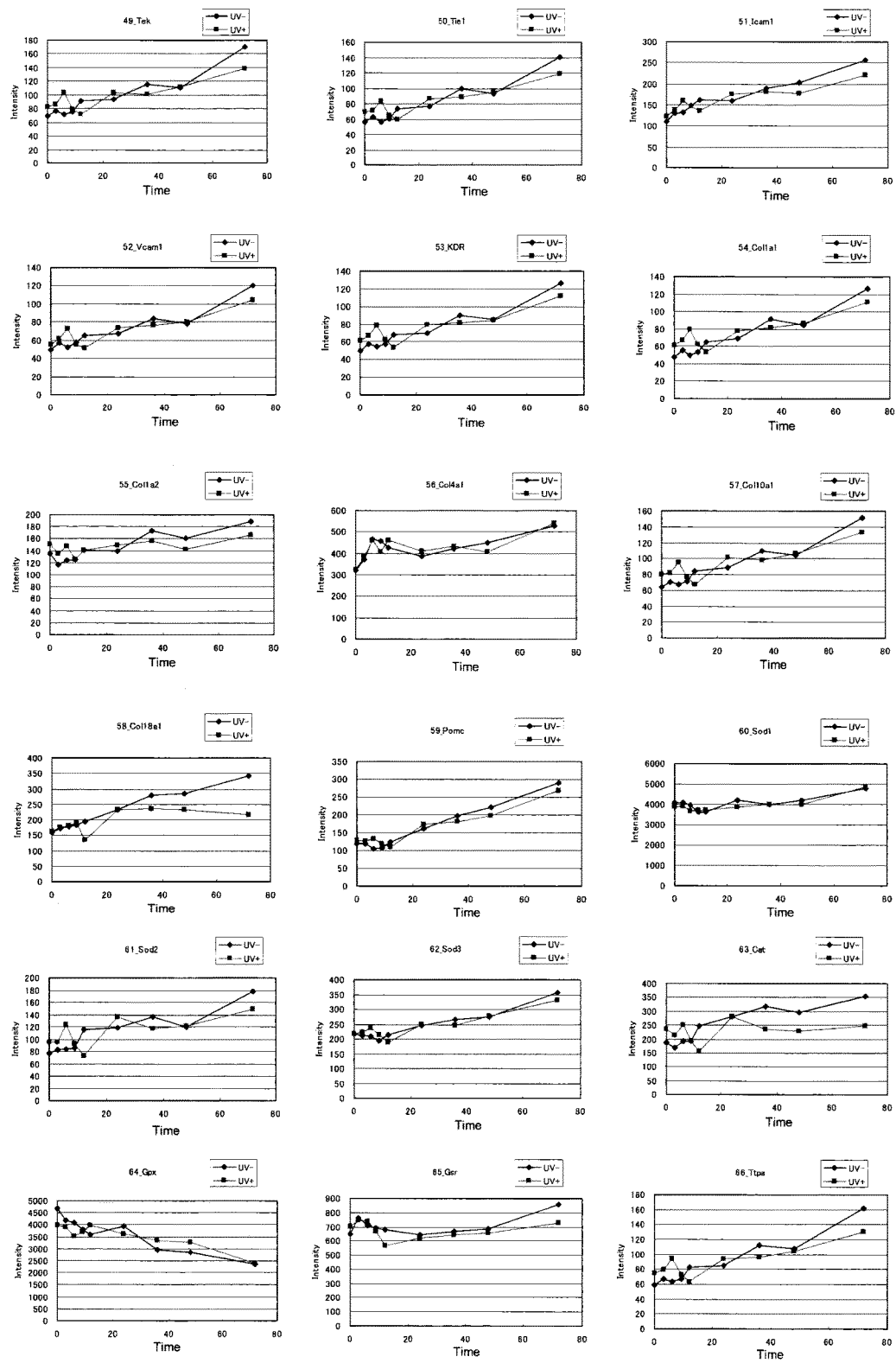
Figure 2E:
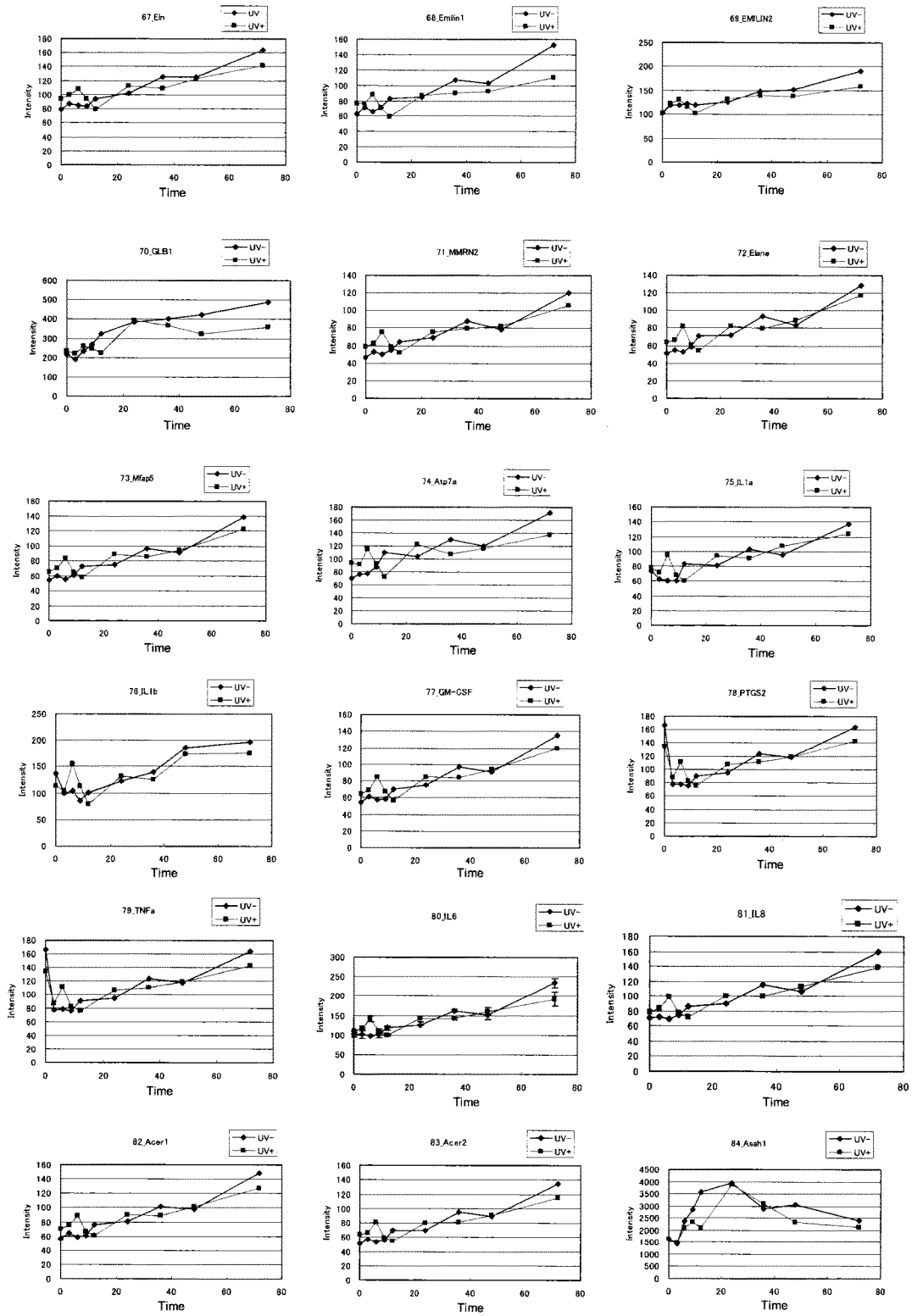
Figure 2F:
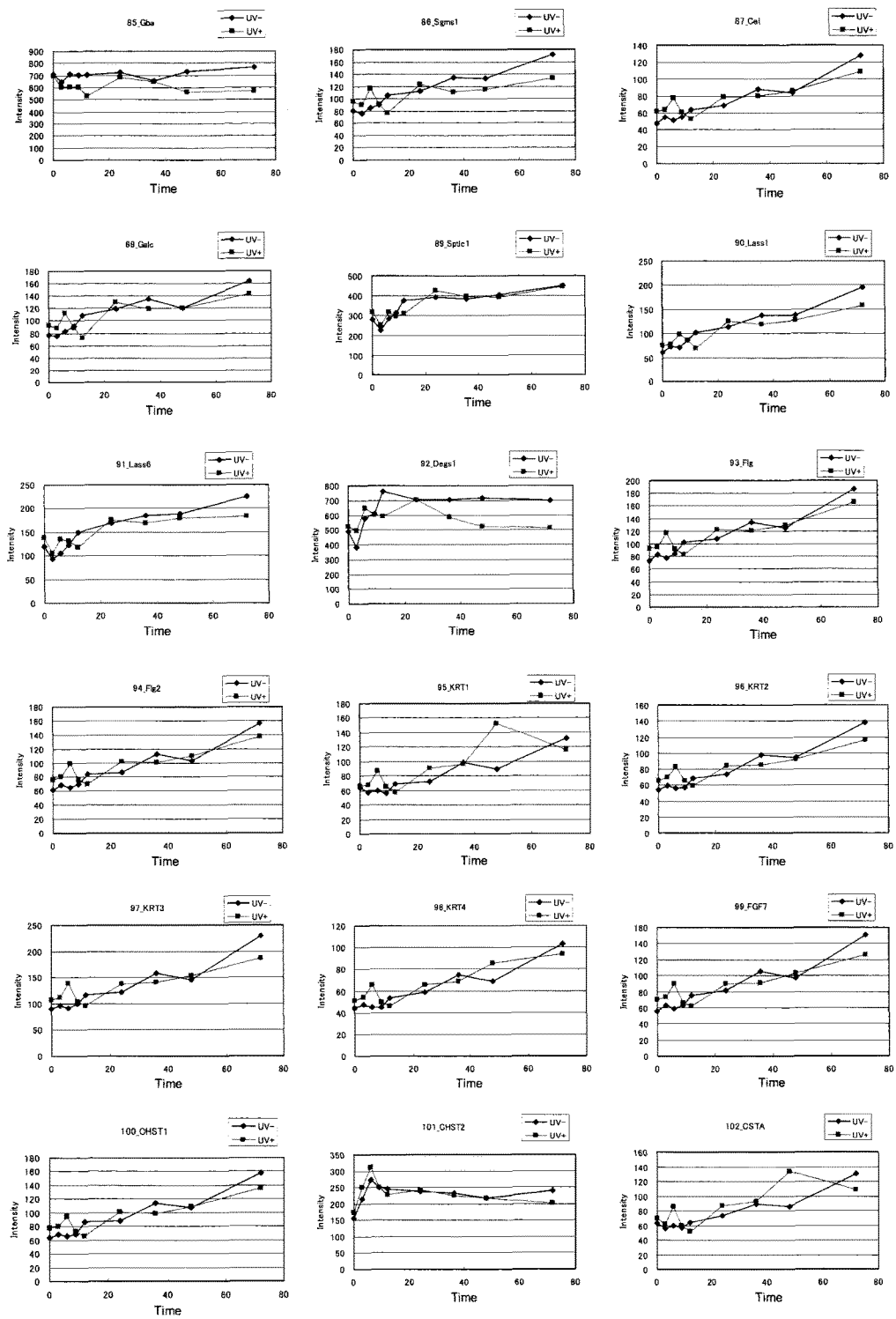
Figure 2G:
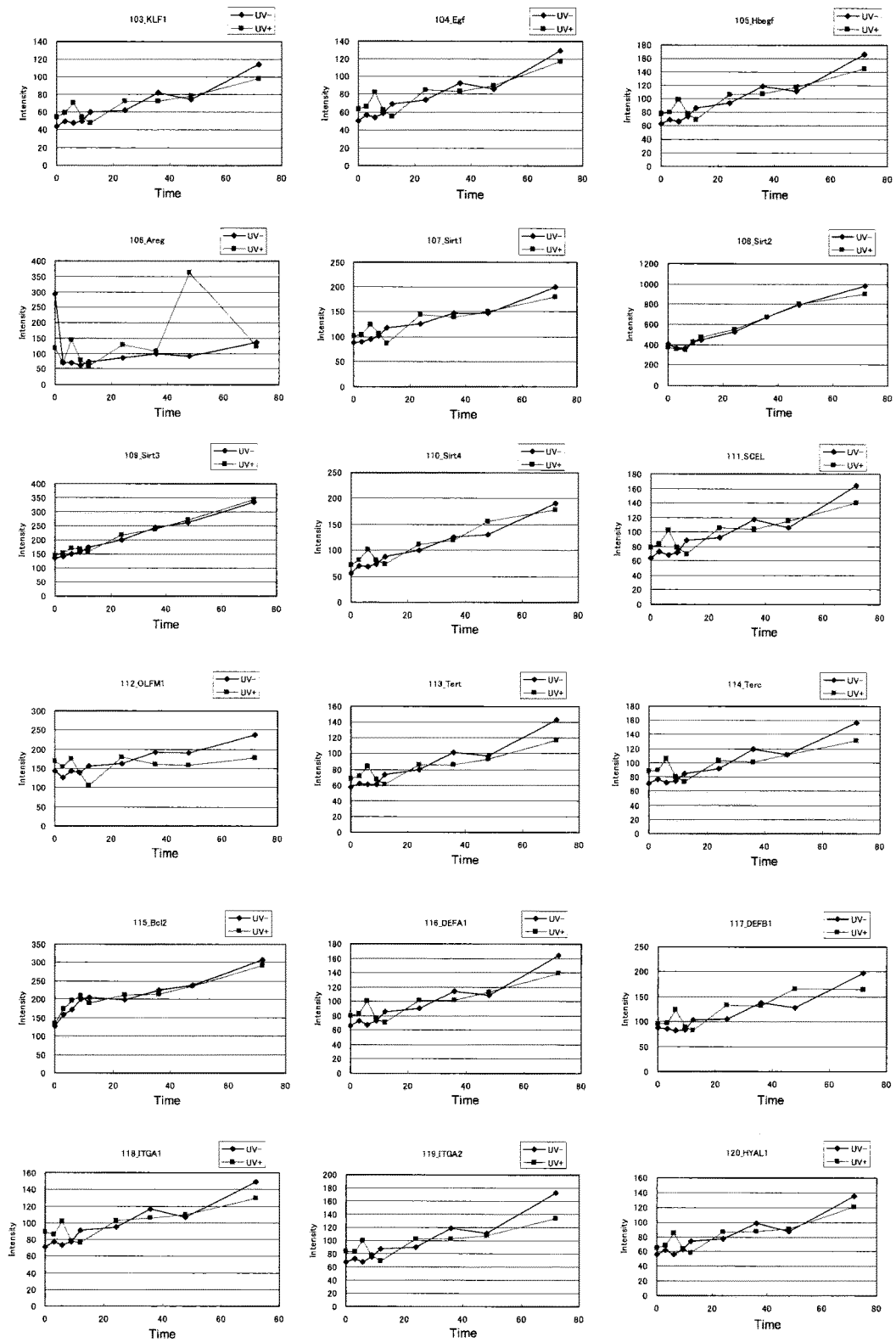
Figure 2H:
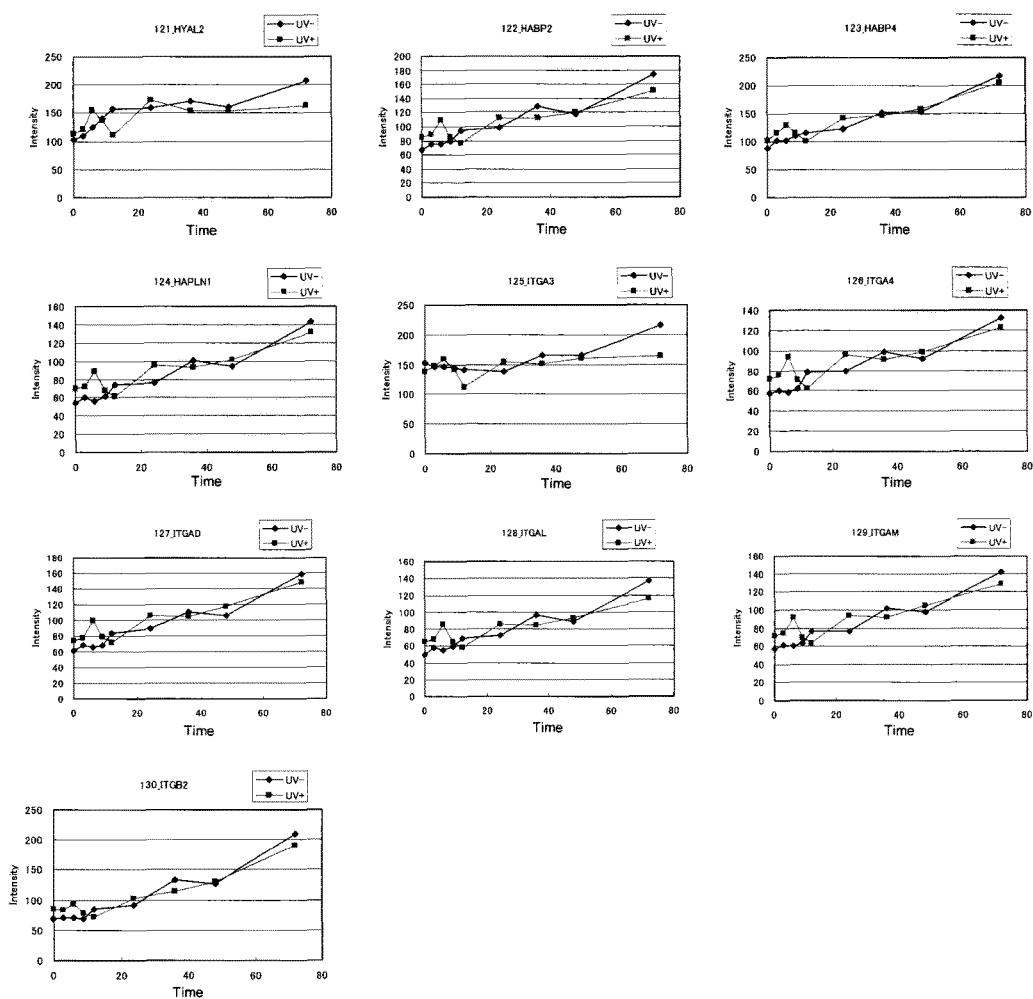

Hereinafter, the invention will be explained in detail. The scope of the invention is not limited to the explanation, and may be implemented with suitable change even beyond the examples described below within a scope where the intention of the invention is not impaired. Further, the specification of Japanese patent application No. 2012-105085 (filed on May 2, 2012), on which the claiming for the priority of the present application is based, are incorporated herein in its entirety. In addition, all of the publications, for example, the prior art documents, and the open publications, the patent publications and the other patent documents cited in the present specification are incorporated herein by reference.

1. Summary of the Invention

The evaluation of the influence of external stimulation, particularly ultraviolet ray on the skin in the invention refers to judgment and evaluation of the skin state such as skin elasticity and wrinkle with presence or absence of the gene expression or the change of the expression amount. Herein, the gene expression is expression of mRNA.

In order to evaluate the skin condition such as skin elasticity and wrinkle in the invention, a gene encoding ceramide, collagen, selectin, elastin or the like, a gene encoding a synthetic enzyme thereof, a gene encoding a catabolic enzyme thereof or a gene associated with inflammation is selected, and can be used as a probe. These genes are referred to as the skin constitution-related gene in the specification and the like. Particularly, in the case where the influence of ultraviolet ray (UV) on the skin state such as wrinkle, aging and skin elasticity is evaluated, at least one kind of gene selected from the group consisting of GBA, GLB1, CAT, OLFM1, ASAH1, MMP14, MMP17 and COL18A1 is selected among the skin constitution-related genes described in detail later, and nucleic acids comprising a base sequence constituting the gene, and the like can be used as a probe.

Herein, examples of the skin constitution-related gene include those described below.

<Skin Constitution-Related Gene>

CKB, CKM, EDN1, EDN2, EDN3, GDNF, NPPB, SELE, SELL, SELP, TNNT2, HAPLN1, HAS1, HAS2, HAS3, FN1, LAMA1, MMP1, MMP2, MMP3, MMP7, MMP9, MMP10, MMP11, MMP12, MMP13, MMP14, MMP15, MMP16, MMP17, MMP24, MMP25, TIMP1, TIMP2, TIMP3, TIMP4, MME, F2RL1, ACO1, ACO2, NFATC1, SUMO1, SUMO2, SUMO3, ADM, PTGES, PTGIS, ANG, TEK, TIE1, ICAM1, VCAM1, KDR, COL1A1, COL1A2, COL4A1, COL10A1, COL18A1, POMC, SOD1, SOD2, SOD3, CAT, GPX, GSR, TTPA, ELN, EMILIN1, EMILIN2, GLB1, MMRN2, ELANE, MFAP5, ATP7A, IL1A, IL1B, GM-CSF, PTGS2, TNFA, IL6, IL8, ACER1, ACER2, ASAH1, GBA, SGMS1, CEL, GALC, SPTLC1, LASS1, LASS6, DEGS1, FLG, FLG2, KRT1, KRT2, KRT3, KRT4, FGF7, CHST1, CHST2, CSTA, KLF1, EGF, HBEGF, AREG, SIRT1, SIRT2, SIRT3, SIRT4, SCEL, OLFM1, TERT, TERC, BCL2, DEFA1, DEFB1, ITGA1, ITGA2.

Information for the base sequence of each of these genes, and the like can be acquired from NCBI (National Center for Biotechnology Information Search term Search database). As the notation for each gene name, the official symbol of NCBI is notated with the capital letter. However, the biological species is not limited thereto. For example, a gene of mammals such as a mouse, a rat, a hamster, a pig, a guinea pig, a monkey, a dog and a cat can be used in addition to a human.

2. Probe for Evaluating the Influence of Ultraviolet Ray on the Skin

A probe generally refers to those used for capturing the nucleic acid (mRNA) of a target gene in a specimen (test sample) by hybridization, and detecting the target nucleic acid. The probe is usually a nucleic acid probe. As the "nucleic acid" constituting the probe in the invention, DNA, RNA, PNA and the like can be generally used, but DNA is preferable although the nucleic acid constituting the probe is not particularly limited.

Examples of the probe (or probe set) for evaluating the influence of ultraviolet ray on the skin in the invention include those comprising the nucleic acids of (a), (b) and (c) described below.

(a) Nucleic acids comprising a base sequence constituting at least one kind (preferably plural kinds) of gene selected from the group consisting of GBA, GLB1, CAT, OLFM1, ASAH1, MMP14, MMP17 and COL18A1

(b) Nucleic acids comprising a base sequence complementary to the nucleic acids of aforesaid (a)

(c) Nucleic acids which hybridize with nucleic acids comprising a base sequence complementary to the nucleic acids of aforesaid (a) or (b) under stringent conditions, and can detect the skin constitution-related gene The nucleic acids of (a) described above are nucleic acids comprising a base sequence at least one kind of gene selected from the genes useful for evaluating the influence of ultraviolet ray on the skin (GBA, GLB1, CAT, OLFM1, ASAH1, MMP14, MMP17 and COL18A1), which are selected from the various skin constitution-related genes described above, and is preferably used in, for example, the aspects described below.

For example, examples of the nucleic acids of (a) described above preferably include:

[1] Those comprising the nucleic acids of (i) and (ii) described below (including a combination of the nucleic acids of (i) and (ii) described below):

(i) nucleic acids comprising a base sequence constituting at least one kind of gene selected from the group consisting of GBA, GLB1, CAT, OLFM1 and ASAH1; and (ii) nucleic acids comprising a base sequence constituting at least one kind of gene selected from the group consisting of MMP14, MMP17 and COL18A1;

[2] Nucleic acids comprising a base sequence constituting each gene of GBA, GLB1, CAT, OLFM1 and ASAH1;

[3] Nucleic acids comprising a base sequence constituting each gene of MMP14, MMP17 and COL18A1;

[4] Nucleic acids comprising a base sequence constituting each gene of MMP14, MMP17, COL18A1, GBA, GLB1, CAT, OLFM1 and ASAH1 and the like.

Furthermore, in the invention, nucleic acids (or a portion thereof) comprising a base sequence of the gene that is the control can be also used together with the nucleic acids of (a) described above, and similarly, can be used together with the nucleic acids of (b) and (c) described below. Examples of the gene that is the positive control include genes such as ACTB, GAPDH and RPLP0.

In addition, the nucleic acids of (b) described above can be also used in evaluation of the influence of ultraviolet ray on the skin and the like in the invention similarly to the nucleic acids of (a) described above. With respect to the nucleic acids of (b) described above, the explanation for the nucleic acids of (a) described above can be similarly applied except that the nucleic acids of (b) comprises the base sequence of the complementary strand of the nucleic acids of (a) described above.

Further, the nucleic acids of (c) described above can be also used in evaluation of the influence of ultraviolet ray on the skin and the like in the invention, similarly to the nucleic acids of (a) and (b) described above.

Herein, the "nucleic acids which hybridize under stringent conditions" in the nucleic acids of (c) described above refers to, for example, nucleic acids obtained by using a colony hybridization method, a plaque hybridization method or Southern hybridization method and the like with the whole or a portion nucleic acids comprising a base sequence complementary to the base sequence of the nucleic acids of aforesaid (a) or (b) as a probe. As the hybridization method, for example, the method described in "Sambrook & Russell, Molecular Cloning: A Laboratory Manual Vol. 3, Cold Spring Harbor, Laboratory Press 2001", "Ausubel, Current Protocols in Molecular Biology, John Wiley & Sons 1987-1997" and the like can be utilized.

In addition, the "stringent conditions" may be any one of low stringent conditions, middle stringent conditions, and high stringent conditions. Examples of the "low stringent conditions" include conditions of 5×SSC, 5×Denhardt's solution, 0.5% SDS, 50% formamide and 32° C. In addition, examples of the "middle stringent conditions" include conditions of 5×SSC, 5×Denhardt's solution, 0.5% SDS, 50% formamide and 42° C. Examples of the "high stringent conditions" include conditions of 5×SSC, 5×Denhardt's solution, 0.5% SDS, 50% formamide and 50° C. Furthermore, specifically, the "stringent conditions" in the invention are preferably conditions of 97.5 to 3200 mM of the monovalent cation concentration of the buffer and 37 to 80° C. of the temperature, more preferably conditions of 97.5 to 800 mM of the monovalent cation concentration and 50 to 70° C. of the temperature, and further preferably conditions of 195 mM of the monovalent cation concentration of the buffer and 65° C. of the temperature, or the like in the case where the base chain length is 65 bases, but are not limited thereto.

In such "stringent conditions", nucleic acids having higher homology can be effectively obtained as the temperature is raised. However, multiple factors such as the temperature, the probe concentration, the probe length, the reaction time, the ionic strength and the salt concentration and the like are considered as factors affecting the stringency of the hybridization, and these factors can be suitably selected by a person skilled in the art to implement the similar stringency.

Furthermore, in the case where a commercially available kit is used in the hybridization, for example, Alkphos Direct Labelling Reagents (manufactured by Amersham Pharmacia Biotech Inc.) may be used. In this case, incubation with the labelled probe is performed overnight according to the protocol accompanied with the kit, and then the membrane is washed with a primary washing buffer comprising 0.1% (w/v) SDS under a condition of 55° C., and then the hybridized nucleic acids can be detected.

Examples of the nucleic acids which can hybridize in addition to those described above may include nucleic acids comprising a base sequence having a homology of 70% or higher, 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher to the base sequence of the nucleic acids of aforesaid (a) when the homology is calculated using default parameters with a homology search software such as FASTA and BLAST.

Furthermore, the homology of the base sequence can be determined using the algorithm BLAST by Karlin and Altschul (Proc. Natl. Acad. Sci. USA, vol. 87, p. 2264-2268, 1990; Proc. Natl. Acad. Sci. USA, vol. 90, p. 5873, 1993). A program called BLASTN or BLASTX was developed based on the algorithm of BLAST (Altschul S F, et al., J. Mol. Biol., vol. 215, p. 403, 1990). The parameters in the case where the base sequence is analyzed using BLASTN are, for example, score=100 and word length=12. In the case where BLAST and Gapped BLAST program are used, default parameters of each program are used. Further, the expression "can detect the skin constitution-related gene" in the nucleic acids of (c) described above means "can capture any one of the base sequences of the skin constitution-related genes (GBA, GLB1, CAT, OLFM1, ASAH1, MMP14, MMP17 and COL18A1) listed in aforesaid (a) and the base sequence of the complementary strand thereof by hybridization.

The nucleic acids of (a), (b) and (c) described above are not limited to the full length of the nucleic acids, but a portion thereof can be also used as a probe. Examples of the portion of the nucleic acids include nucleic acids comprising 30 to 5000 bases, nucleic acids comprising 40 to 1000 bases, nucleic acids comprising 50 to 500 bases, and further nucleic acids comprising 60 bases to 200 bases, and the like, but the base length is not particularly limited.

In addition, examples of the probe (or probe set) for evaluating the influence of ultraviolet ray on the skin in the invention include those comprising the nucleic acids of (α), (β), (γ) and (δ) described below.

(α) Nucleic acids comprising at least one kind of base sequence among the base sequences shown in SEQ ID NOS: 27, 30, 58, 63, 70, 84, 85 and 112

(β) Nucleic acids comprising a base sequence complementary to the nucleic acids of aforesaid (α)

(γ) Nucleic acids comprising a base sequence having a homology of 70% or higher with respect to the base sequence of the nucleic acids of aforesaid (α) or (β), and can detect the skin constitution-related gene (δ) Nucleic acids which comprises a base sequence of which one to several bases are added, deleted or substituted in the base sequence of the nucleic acids of aforesaid (α), (β) or (γ), and can detect the skin constitution-related gene The nucleic acids of (α) described above are a nucleic acid having the base sequences shown in SEQ ID NOS: 27, 30, 58, 63, 70, 84, 85 and 112, and the base sequences shown in the SEQ ID NOS are base sequences corresponding to a portion of the base sequences of the skin constitution-related genes in the nucleic acids of (a) described above (GBA, GLB1, CAT, OLFM1, ASAH1, MMP14, MMP17 and COL18A1). Accordingly, the nucleic acids of (α) described above can be also effectively used as a probe (or probe set) for evaluation of the influence of ultraviolet ray on the skin and the like in the invention.

In addition, examples of the nucleic acids of (α) described above preferably include aspects including all the nucleic acids comprising each of the base sequences shown in SEQ ID NOS: 27, 30, 58, 63, 70, 84, 85 and 112.

Furthermore, among the base sequences shown in SEQ ID NOS: 1 to 273 listed in the sequence listing and Tables 1 to 4 described below, the base sequences shown in SEQ ID NOS: 1 to 257 correspond to a portion of the base sequences of the skin constitution-related genes (derived from human or mouse), and the base sequences shown in SEQ ID NOS: 258 to 273 correspond to a portion of the base sequences of genes (derived from human or mouse) that can be used as a control in the evaluation and the like in the invention. Furthermore, the base sequences shown in SEQ ID NOS: 258 to 271 are positive controls, and the base sequences shown in SEQ ID NOS: 272 and 273 are negative controls. Herein, the base sequences shown in SEQ ID NOS: 27, 30, 58, 63, 70, 84, 85 and 112 in the nucleic acids of (α) described above correspond to a portion of the base sequences of the genes of MMP14, MMP17, COL18A1, CAT, GLB1, ASAH1, GBA and OLFM1, respectively in order.

TABLE 1

| SEQ ID NO | Accession No. | Gene symbol | Base sequence of nucleic acid probe |
|---|---|---|---|
| 1 | NM_001823 | CKB | CGCCGTCTGGCGAGCCCTTAGCCTTGCTGTAGAGACTTCCGTCACCCTTGGTAGAGTTTATTTTT |
| 2 | NM_001824 | CKM | TGGGGGCTCTCTCCACCCTTCTCAGAGTTCCAGTTTCAACCAGAGTTCCAACCAATGGGCTCCAT |
| 3 | NM_001955 | EDN1 | AGGAGATTCCACACAGGGGTGGAGTTTCTGACGAAGGTCCTAAGGGAGTGTTTGTGTCTGACTCA |
| 4 | NM_001956 | EDN2 | TTCTGCCACTTGGACATCATCTGGGTGAACACTCCTGAACAGACAGCTCCTTACGGCCTGGGAAA |
| 5 | NM_000114 | EDN3 | CCCGTGCAGCAGAAGCATGCGACTTTCATATCCTTGCCTAGAATAGGCTGCATGGTGTATGTCAG |
| 6 | NM_000514 | GDNF | CACCATCTGATACCGTAAGGAGTGCACTTGTTTGGAAGTTCTGACTTCTCTGATCTGTCTTGGTC |
| 7 | NM_002521 | NPPB | CTGCTTCTGATTCCACAAGGGGCTTTTTCCTCAACCCTGTGGCCGCCTTTGAAGTGACTCATTTT |
| 8 | NM_000450 | SELE | CTAGCCTTGAGGAGTGTGAGAATCAAAACTCTCCTACACTTCCATTAACTTAGCATGTGTTGAAA |
| 9 | NM_000655 | SELL | CACCTCTCTTTTTCAGTTGGCTGACTTCCACACCTAGCATCTCATGAGTGCCAAGCAAAAGGAGA |
| 10 | NM_003005 | SELP | TCTACGATAGGTCTGATAATGGGTGGGACGCTCCTGGCTTTGCTAAGAAAGCGTTTCAGACAAAA |
| 11 | NM_000364 | TNNT2 | ACTTTGAGAACAGGAAGAAAGAGGAGGAGGAGCTCGTTTCTCTCAAAGACAGGATCGAGAGACGT |
| 12 | NM_001884 | HAPLN1 | ACATCGTTTTGTTAAGAAGTTAACTGTATCGTAGCTCACTACTGCCAGAGCGGCAATGGATGTAC |
| 13 | NM_001523 | HAS1 | CGGGCTTGTCAGAGCTACTTCCACTGTGTATCCTGCATCAGCGGTCCTCTAGGCCTATATAGGAA |
| 14 | NM_005328 | HAS2 | GACGTTTGCAGTCACACACAACACCTTAGTTCCTCTAGGGGCTGTACAGTATTGTGGCATCAGAT |
| 15 | NM_005329 | HAS3 | GGGTCTTCAGCTTTATCCCCGTTTCTTGCAAGGGAAGAGCCTTTATACAATTGGACGCATTTTGG |
| 16 | NM_002026 | FN1 | CCCAAACACTTCTGCTTTCACTTAAGTGTCTGGCCCGCAATACTGTAGGAACAAGCATGATCTTG |
| 17 | NM_005559 | LAMA1 | AAGCTAACAAAAGCAAACACCGTATCACTCTGATTGTTGACGGGAACGCAGTTGGCGCTGAAAGT |
| 18 | NM_001145938 | MMP1 | ATGCAACTCTGACGTTGATCCCAGAGAGCAGCTTCAGTGACAAACATATCCTTTCAAGACAGAAA |

TABLE 1-continued

| SEQ ID NO | Accession No. | Gene symbol | Base sequence of nucleic acid probe |
|---|---|---|---|
| 19 | NM_001127891 | MMP2 | TCACTCTACTTAGCATGTCCCTACCGAGTCTCTTCTCCACTGGATGGAGGAAAACCAAGCCGTGG |
| 20 | NM_002422 | MMP3 | TTCCCAAGAGAAGGGGAAGCACTCGTGTGCAACAGACAAGTGACTGTATCTGTGTAGACTATTTG |
| 21 | NM_002423 | MMP7 | CTTGGCCATTCTTTGGGTATGGGACATTCCTCTGATCCTAATGCAGTGATGTATCCAACCTATGG |
| 22 | NM_004994 | MMP9 | ACGTCTTCCAGTACCGAGAGAAAGCCTATTTCTGCCAGGACCGCTTCTACTGGCGCGTGAGTTCC |
| 23 | NM_002425 | MMP10 | CACACATATTAAAGAGTAACAGCTGGTTACATTGCTAGGCGAGATAGGGGGAAGACAGATATGGG |
| 24 | NM_005940 | MMP11 | TGTCTCAGACTGGGCAGGGAGGCTTTGGCATGACTTAAGAGGAAGGGCAGTCTTGGGCCCGCTAT |
| 25 | NM_002426 | MMP12 | AGGAGGCACAAACTTGTTCCTCACTGCTGTTCACGAGATTGGCCATTCCTTAGGTCTTGGCCATT |
| 26 | NM_002427 | MMP13 | GGGGAGGGTGCTTGGCACTTATTGAATATATGATCGGCCATCAAGGGAAGAACTATTGTGCTCAG |
| 27 | NM_004995 | MMP14 | GCACGGGTAGGGGAAATGGGGTGAACGGTGCTGGCAGTTCGGCTAGATTTCTGTCTTGTTTGTT |
| 28 | NM_002428 | MMP15 | GGTGGGGCTGCGGGGGTTCCGTGTCCACCCCCATACATTTATTTCTGTAAATAATGTGCACTGAA |
| 29 | NM_005941 | MMP16 | GGGCCAAGAAAGCAAGAAATGAGAACCAGAGTCAGCCCTGTAGCTTTACTTCAGTGCTTCCATTC |
| 30 | NM_016155 | MMP17 | ATT1CTTTAAGGACCAGCTGTACTGGCGCTACGATGACCACACGAGGCACATGGACCCCGGCTAC |
| 31 | NM_006690 | MMP24 | TTATTAGCTCACACCTGTCCACTCACATGAAACTCGTGTTAGGCCCTGGGAGGCCGACGGTAACT |
| 32 | NM_022468 | MMP25 | ATGGCCTGAACCCCATGGGTAGAGTCACTTAGGGGCCACTTCCTAAGTTGCTGTCCAGCCTCAGT |
| 33 | NM_003254 | TIMP1 | TTCCCTGTTTATCCATCCCTGCAAACTGCAGAGTGGCACTCATTGCTTGTGGACGGACCAGCTC |
| 34 | NM_003255 | TIMP2 | TGACAAGCAGACTGCGCATGTCTCTGATGCTTTGTATCATTCTTGAGCAATCGCTCGGTCCGTGG |
| 35 | NM_000362 | TIMP3 | TTGGGGGTAGAGGCTTCTTAGATTCTCCCAGCATCCGCCTTTCCCTTTAGCCAGTCTGCTGTCCT |
| 36 | NM_003256 | TIMP4 | GCCCCTGCCTCCCAAACCCCATTAGTCTAGCCTTGTAGCTGTTACTGCAAGTGTTTCTTCTGGCT |
| 37 | NM_000902 | MME | CCCATGAATCTGTCTCCCAGTTATGAATCAGTGGGCAGGATAAACTGAAAACTCCCATTTACGTG |
| 38 | NM_005242 | F2RL1 | CCTGCATGGTGTTTATGCACACAGAGATTTGAGAACCATTGTTCTGAATGCTGCTTCCATTTGAC |
| 39 | NM_002197 | ACO1 | AACCTTCTCAGGAGGTGTCTCCTACCCTCTTATTGTTCCTCTTACGCTCTGCTCAATGAAACCTT |
| 40 | NM_001098 | ACO2 | ACCTTCAACGAGACGCAGATTGAGTGGTTCCGCGCTGGCAGTGCCCTCAACAGAATGAAGGAACT |
| 41 | NM_172390 | NFATC1 | AAAACTGACCGGGACCTGTGCAAGCCGAATTCTCTGGTGGTTGAGATCCCGCCATTTCGGAATCA |
| 42 | NM_003352 | SUMO1 | AGGCGTAGCGGAAGTTACTGCAGCCGCGGTGTTGTGCTGTGGGAAGGGAGAAGGATTTGTAAAC |
| 43 | NM_006937 | SUMO2 | TCTTCTGCCGCTCCTGGTGCTGCTTGTGTGCTCGTTTGGTGCGGACCTGGTACCTCTTTTGTGAA |
| 44 | NM_006936 | SUMO3 | CCCATGGAATGATGACTTCATGTTCTTCTCGTGGGTTTGTGCCGTGCTGCTTTCCAAATAGGTAT |
| 45 | NM_001124 | ADM | CCCACAAACTGATTTCTCACGGCGTGTCACCCCACCAGGGCGCAAGCCTCACTATTACTTGAACT |
| 46 | NM_004878 | PTGES | CCTAGACCCGTGACCTGAGATGTGTGATTTTTAGTCATTAAATGGAAGTGTCTGCCAGCTGGGCC |
| 47 | NM_000961 | PTGIS | GGGAGAGATGAGTGGGTTAGCTACCTGCTATGCGCTAGTTAGGAAGTTACCTGGATGCCATTGTA |
| 48 | NM_001145 | ANG | AACCTAAGAATAAGCAAGTCTTCTTTCCAGGTCACCACTTGCAAGCTACATGGAGGTTCCCCCTG |
| 49 | NM_000459 | TEK | CTCACCTGTAGCAGCCAGTCCCGTTTCATTTAGTCATGTGACCACTCTGTCTTGTGTTTCCACAG |
| 50 | NM_005424 | TIE1 | GCATGCTGGAAGCCAGGAAGGCCTATGTGAACATGTCGCTGTTTGAGAACTTCACTTACGCGGGC |
| 51 | NM_000201 | ICAM1 | GACGGATGCCAGCTTGGGCACTGCTGTCTACTGACCCCAACCCTTGATGATATGTATTTATTCAT |
| 52 | NM_001078 | VCAM1 | GGGAGCACTGGGTTGACTTTCAGGTACTAAATACCTCAACCTATGGTATAATGGTTGACTGGGTT |
| 53 | NM_002253 | KDR | GGCATGGGGTCTGTTCTGAAATGTAAAGGGTTCAGACGGGGTTTCTGGTTTTAGAAGGTTGCGTG |
| 54 | NM_000088 | COL1A1 | CTGTTCCTTGTGTAACTGTGTTGCTGAAAGACTACCTCGTTCTTGTCTTGATGTGTCACCGGGGC |
| 55 | NM_000089 | COL1A2 | AGGAGCTCCAAGGACAAGAAACACGTCTGGCTAGGAGAAACTATCAATGCTGGCAGCCAGTTTGA |
| 56 | NM_001845 | COL4A1 | TCAGCAGGGCATCGCATGGACCGCAGGAGGGCAGATTCGGACCACTAGGCCTGAAATGACATTTC |
| 57 | NM_000493 | COL10A1 | ATCAGACCAACAAACCTTCCCCCTGAAAAGTGAGCAGCAACGTAAAAACGTATGTGAAGCCTCTC |

TABLE 1-continued

| SEQ ID NO | Accession No. | Gene symbol | Base sequence of nucleic acid probe |
|---|---|---|---|
| 58 | NM_030582 | COL18A1 | TGTGCACAAAACCCAGACCTGTTAGCAGACAGGCCCCGTGAGGCAATGGGAGCTGAGGCCACACT |
| 59 | NM_001035256 | POMC | GGGGGTCGTGGCAGATAATCAGCCTCTTAAAGCTGCCTGTAGTTAGGAAATAAAACCTTTCAAAT |
| 60 | NM_000454 | SOD1 | GCCCAATAAACATTCCCTTGGATGTAGTCTGAGGCCCCTTAACTCATCTGTTATCCTGCTAGCTG |
| 61 | NM_000636 | SOD2 | GGCAGCTCATGCTTGAGACCCAATCTCCATGATGACCTACAAGCTAGAGTATTTAAAGGCAGTGG |
| 62 | NM_003102 | SOD3 | ACTCAGTAGGTCTGAAGGCCTCCATTTGTACCGAAACACCCCGCTCACGCTGACAGCCTCCTAGG |
| 63 | NM_001752 | CAT | GCCTTCTGCCCTGGAGCACAGCATCCAATATTCTGGAGAAGTGCGGAGATTCAACACTGCCAATG |
| 64 | NM_000581 | GPX | ACGAGGGAGGAACACCTGATCTTACAGAAAATACCACCTCGAGATGGGTGCTGGTCCTGTTGATC |
| 65 | NM_000637 | GSR | GTGAAGTGCATCAAACTTGGGAAAGATTTGAGGAGGCTGGGAACCTCCTGGAAAACCACTCCTTG |
| 66 | NM_000370 | TTPA | GCCTGGCCGTGATAGAAACTTTCAGCTGAGGAGTCTATATGCCATACTACTCTATGTGGCATCTT |
| 67 | NM_000501 | ELN | AATAGCCACCTTGCCCTTGTAGAATCCATCCGCCCATCCGTCCATTCATCCATCGGTCCGTCCAT |
| 68 | NM_007046 | EMILIN1 | TGATCTGGCTGACCTGGGGCAACCAAGGACCGTATCATTTCTGAGATTAACAGGCTGCAGCAGG |
| 69 | NM_032048 | EMILIN2 | CGGTTTGTATGTAATGGAAGCACGGGGCTAGAGTTTCCACATAGGCCCCAACATAAAGGCCTTCC |
| 70 | NM_000404 | GLB1 | ATGAAGCCTGGGCCCACAACTCATCCAACTACACGCTCCCGGCCTTTTATATGGGAACTTCTCC |

TABLE 2

| SEQ ID NO | Accession No. | Gene symbol | Base sequence of nucleic acid probe |
|---|---|---|---|
| 71 | NM_024756 | MMRN2 | CCTTGCCTTACATAGGGTAAAGACCAAGAAATGCCAAACGTGAACTAAAATATGTAGGGCCTTCA |
| 72 | NM_001972 | ELANE | TCGCCGTGCAGCGCATCTTCGAAAACGGCTACGACCCCGTAAACTTGCTCAACGACATCGTGATT |
| 73 | NM_003480 | MFAP5 | CAAGTGCACGGTCGAATTATTGTGCAAGTGGCTTTTGGATATCCTGATTGGGGCCTAAGAAGGGC |
| 74 | NM_000052 | ATP7A | GCCAAATGGATTTAGAAATTCCCTTGTGAGTGCCTGGTAGCTAATACACTGGTCAGAGATCTGGT |
| 75 | NM_000575 | IL1A | GGCGTAGGTCTGGAGTCTCACTTGTCTCACTTGTGCAGTGTTGACAGTTCATATGTACCATGTAC |
| 76 | NM_000576 | IL1B | AATCCCCAGCCCTTTTGTTGAGCCAGGCCTCTCTCACCTCTCCTACTCACTTAAAGCCCGCCTGA |
| 77 | NM_000758 | GM-CSF | GGCCCGGCGTCTCCTGAACCTGAGTAGAGACACTGCTGCTGAGATGAATGAAACAGTAGAAGTCA |
| 78 | NM_000963 | PTGS2 | GATCTGCTGACAAAACCTGGGAATTTGGGTTGTGTATGCGAATGTTTCAGTGCCTCAGACAAATG |
| 79 | NM_000594 | TNFA | CCTAGAAATTGACACAAGTGGACCTTAGGCCTTCCTCTCTCCAGATGTTTCCAGACTTCCTTGAG |
| 80 | NM_000600 | IL6 | ACAGCCACTCACCTCTTCAGAACGAATTGACAAACAAATTCGGTACATCCTCGACGGCATCTCAG |
| 81 | NM_000584 | IL8 | GTTTCTCCTTTATTTCTAAGTGGAAAAAGTATTAGCCACCATCTTACCTCACAGTGATGTTGTGA |
| 82 | NM_133492 | ACER1 | ACTATCCAACCACCCAACAACTTGCCTGTGTCTTGAGAAGATAGCCCCGGTCAGGACTTGCACCT |
| 83 | NM_001010887 | ACER2 | CCAGGAACTCTTACTCTAGTTAGAATTTGTACCAGATCCAAGGTGAAAACCCCAATAAGCAACTG |
| 84 | NM_177924 | ASAH1 | GCTGTCTGACCTTCCAAAGACTAAGACTCGCGGCAGGTTCTCTTTGAGTCAATAGCTTGTCTTCG |
| 85 | NM_000157 | GBA | GACATCACCAAGGACACGTTTTACAAACAGCCCATGTTCTACCACCTTGGCCACTTCAGCAAGTT |
| 86 | NM_147156 | SGMS1 | CCTCCCTAATCCTATTATCTTTCAATGGTTACCTTGACTTAACCTATTGAGTTACCTGGTCAGCA |
| 87 | NM_001807 | CEL | CAACATGGACGGCCACATCTTCGCCAGCATCGACATGCCTGCCATCAACAAGGGCAACAAGAAAG |
| 88 | NM_000153 | GALC | CCATACCCTTAGGAGTGGTTTGAGTAGTACAGACCTCGAAGCCTTGCTGCTAACACTGAGGTAGC |
| 89 | NM_006415 | SPTLC1 | GGTGGGTTTGCCTAGGGACGTGTAACTACAGGCTTTTACTAAGCCAAGGAAAAAGAGAATTTTTC |
| 90 | NM_021267 | LASS1 | CACCCTTATGAACCTCTACTGGTTCCTGTACATCGTGGCGTTTGCAGCCAAGGTGTTGACAGGCC |
| 91 | NM_203463 | LASS6 | CGGGACCTAAGAAAGTCTCTGCAGCCAGATAGTACATGGTGTCTCCACAAAACTAGGCATTCTGG |

TABLE 2-continued

| SEQ ID NO | Accession No. | Gene symbol | Base sequence of nucleic acid probe |
|---|---|---|---|
| 92 | NM_003676 | DEGS1 | CCAGTGATGCTCAGAAGCTCCCCTGGCACAATTTCAGAGTAAGAGCTCGGTGATACCAAGAAGTG |
| 93 | NM_002016 | FLG | GGCAGCTATGGTAGTGCAGATTATGATTATGGTGAATCCGGGTTTAGACACTCTCAGCACGGAAG |
| 94 | NM_001014342 | FLG2 | GTGGGGGAGACAAAGGCAAGAGTCAGAGTCAAGTCTGTCAGGAGGTATCAGAATATACGGTGAGG |
| 95 | NM_006121 | KRT1 | AGCTCTAGTTCTCCCCCAGCATCACTAACAAATATGCTTGGCAAGACCGAGGTCGATTTGTCCCA |
| 96 | NM_000423 | KRT2 | TTTCATCAAATGTGGCATCCAAGGCTGCCTTTGGAGGTTCTGGAGGTAGAGGGTCCAGTTCCGGA |
| 97 | NM_057088 | KRT3 | TCTTTTTGAGAATCACATCAACTACCTGCGGAGCTACCTGGACAACATCCTCGGGGAGAGAGGGC |
| 98 | NM_002272 | KRT4 | TCTCCCACTAGATCCTGTATTATCCATCTACATCAGAACCAAACTACTTCTCCAACACCCGGCAG |
| 99 | NM_002009 | FGF7 | CACGCAGCTGGGTAGATATACAGCTGTCACAAGAGTCTAGATCAGTTAGCACATGCTTTCTACTC |
| 100 | NM_003654 | CHST1 | GGCACTCGCGAGGCGACTTCTCAAGCTTTTGAATGGGTGAGTGGTCGGGTATCTAGTTTTTGCAC |
| 101 | NM_004267 | CHST2 | GCCCCATTGGGCATGATAAGCCGAGGAGGCATTCTTCTAAAGCAGACTTTTGTGTAAAAAGCAAA |
| 102 | NM_005213 | CSTA | GTTCCCTGTGGCTGCTGATAACCCAACATTCCATCTCTACCCTCATACTTCAAAATTAAATCAAG |
| 103 | NM_006563 | KLF1 | GCTTCCCAGAGACCCTGGGTCTAGAAAGCGGCTCCTGAAGGTCCCTTATTGTGGCTGATATTAAC |
| 104 | NM_001963 | EGF | CCTGCAGCCCCAGAAGAAATTAGGGGTTAAAGCAGACAGTCACACTGGTTTGGTCAGTTACAAAG |
| 105 | NM_001945 | HBEGF | GGATGTAGGGGTTAACTTGGTCAGAGCCACTCTATGAGTTGGACTTCAGTCTTGCCTAGGCGATT |
| 106 | NM_001657 | AREG | GCCAAGTCATAGCCATAAATGATGAGTCGGTCCTCTTTCCAGTGGATCATAAGACAATGGACCCT |
| 107 | NM_012238 | SIRT1 | GGCGGCTTGATGGTAATCAGTATCTGTTTTTGCCACCAAATCGTTACATTTTCCATGGCGCTGAG |
| 108 | NM_012237 | SIRT2 | GGCTAAGTAAACCATACCTAACCTACCCCAGTGTGGGTGTGGGCCTCTGAATATAACCCACACCC |
| 109 | NM_012239 | SIRT3 | CTTTCTGTGCCTAGTTGAACGGCAAGCTCGGCATCTGTTGGTTACAAGATCCAGACTTGGGCCGA |
| 110 | NM_012240 | SIRT4 | TACTGAACATTGGGCCCACACGGTCGGATGACTTGGCGTGTCTGAAACTGAATTCTCGTTGTGGA |
| 111 | NM_144777 | SCEL | AATTGAAGTAAATTCTCATGTGTCTGAAAACAAGAATGGAAGCTCTAACACTGGAGCCAAGCAGG |
| 112 | NM_014279 | OLFM1 | GGCCCACGTCCTCACCACAAAGGGACTCCTGTGAAACTGCTGCCAAAAAGATACCAATAACACTA |
| 113 | NM_198253 | TERT | AGACGGTGTGCACCAACATCTACAAGATCCTCCTGCTGCAGGCGTACAGGTTTCACGCATGTGTG |
| 114 | NR_001566 | TERC | TTTTTGTCTAACCCTAACTGAGAAGGGCGTAGGCGCCGTGCTTTTGCTCCCCGCGCGCTGTTTTT |
| 115 | NM_1000633 | BCL2 | CTCCAGTTGGCCACCATTAGCTATAATGGCACTTTGTTTGTGTTGTTGGAAAAAGTCACATTGCC |
| 116 | NM_004084 | DEFA1 | ATGGCCTGCTATTGCAGAATACCAGCGTGCATTGCAGGAGAACGTCGCTATGGAACCTGCATCTA |
| 117 | NM_005218 | DEFB1 | ACCTGTTACAGAGGGAAGGCCAAGTGCTGCAAGTGAGCTGGGAGTGACCAGAAGAAATGACGCAG |
| 118 | NM_181501 | ITGA1 | TGACCCAAAGAAAGAGTTGTCTCAACTCCTTGGTACAGGGTTCATTCAAACCCCCAAGCTGTGAG |
| 119 | NM_002203 | ITGA2 | GGAACTTGAAAGCTTTGGTTAGCCTTGCCTTAGGTAATCAGCCTAGTTTACACTGTTTCCAGGGA |
| 120 | NM_007312 | HYAL1 | ATCAAGGAGTATATGGACACTACACTGGGGCCCTTCATCCTGAACGTGACCAGTGGGCCCTTCT |
| 121 | NM_003773 | HYAL2 | CAACTTTGTGAGCTTCCGTGTTCAGGAGGCCCTTCGTGTGGCTCGCACCCACCATGCCAACCATG |
| 122 | NM_004132 | HABP2 | AAAATGCAGACTGTCATATCCAGCGAGTCCCTGACCCTTTCTGCGAATGTAACGAGCAAGCAGTC |
| 123 | NM_014282 | HABP4 | CTCACTTAGTCCTGGCTCCAGTTCTAGAGTTCCTCTTTATTGCTTTTGGTGAAAGTTTGGGGTTG |
| 124 | NM_001884 | HAPLN1 | ACATCGTTTTGTTAAGAAGTTAACTGTATCGTAGCTCACTACTGCCAGAGCGGCAATGGATGTAC |
| 125 | NM_002204 | ITGA3 | TCCATCTTGAGCCACAGTCACTGGATTGACTTTGCTGTCAAAACTACTGACAGGGAGCAGCCCCC |
| 126 | NM_000885 | ITGA4 | GCAAAAGAGTGCAATGCAGACCTTGAAAGGCATAGTCCGGTTCTTGTCCAAGACTGATAAGAGGC |
| 127 | NM_005353 | ITGAD | ACCCAGGGACCTGAGTGCCTCTCTGGGAATAGTCGGGGGAACCTATTTGTGGGCATTGAAAAAGT |
| 128 | NM_001114380 | ITGAL | CCCTGTTTAATGATTGACGTACTTAGCAGCTATCTCTCAGTGAACTGTGAGGGTAAAGGCTATAC |
| 129 | NM_000632 | ITGAM | CCTCTCGTTTGACTGGTACATCAAGACCTCGCATAACCACCTCCTGATCGTGAGCACAGCTGAGA |
| 130 | NM_000211 | ITGB2 | ATTAACCAGAAATCCAGTTATTTTCCGCCCTCAAAATGACAGCCATGGCCGGCCGGGTGCTTCTG |

TABLE 2-continued

| SEQ ID NO | Accession No. | Gene symbol | Base sequence of nucleic acid probe |
|---|---|---|---|
| 131 | NM_021273 | Ckb | AAGTCCAAGAACTATGAGTTCATGTGGAATCCTCACCTGGGCTACATCCTCACATGCCCATCCAA |
| 132 | NM_007710 | Ckm | ATGCCCGTGGCATCTGGCACAACGACAACAAAAGCTTCCTTGTGTGGGTGAACGAGGAGGACCAC |
| 133 | NM_010104 | Edn1 | CTTGACCTTGGGAAACACAATGGTTTAGAGTTGTTTGTGTACATGTTGAAAACCTGGTCTGTGCT |
| 134 | NM_007902 | Edn2 | TGGTTGCTAGCTACTGTACCTGCTTGGAGGAGCTATGTGAGGACAAATGAACATGCTGACTGTAT |
| 135 | NM_007903 | Edn3 | CAAAGCATCTGAGAATTATCTCCAGAAGTGATCACAGTAGCAAGGCCACACAGGACATAAAAGCA |
| 136 | NM_010275 | Gdnf | TTGTCTGGCAGCCAACAAACAGGTCATGCCTTGAGTCCTATGTTAGAGCCTTGAGTCCTATGTTA |
| 137 | NM_008726 | Nppb | TGGATCTCCTGAAGGTGCTGTCCCAGATGATTCTGTTTCTGCTTTTCCTTTATCTGTCACCGCTG |
| 138 | NM_011345 | Sele | GTCCTGGCACTGAAGCCAGCATGAGATCCATCATTCTTATGTCAGCTCAAGGGTCAAAAGGACTT |
| 139 | NM_011346 | Sell | ATTGGAAAATAACGTCAAGTCCTCCCGTGAAGATTTTACACGCAGGCATCTCCCACATTAGAGAT |
| 140 | NM_011347 | Selp | TATGACCCAACCCCTTAAGAAACCCGGTCTGCCAATGTCTCATTCGATTTCTCAGGATTCCACAT |

TABLE 3

| SEQ ID NO | Accession No. | Gene symbol | Base sequence of nucleic acid probe |
|---|---|---|---|
| 141 | NM_011619 | Tnnt2 | AAAACTCGTGGGAAGGCCAAAGTCACCGGGCGTTGGAAATAGATGAAACTGTTCTCGTCAAAGCT |
| 142 | NM_013500 | Hapln1 | CCTTTTTGAGAAGTATGTCATTGCTCAAGACTGCCAGCACAGTGTACAGCAAAAGCTATGAATAA |
| 143 | NM_008215 | Has1 | ATGCACCACTCTACATGTGCGGCCTCCTGCCTGCCAAATTCCTAGCGTTGGTTACCATGAATCAA |
| 144 | NM_008216 | Has2 | CCCTTACTGTGCATCTGCCTGACAGTGTTTGTTCTAAATACCTCACTTGCCATGCTTTGTGTGGG |
| 145 | NM_008217 | Has3 | TGAGTTTCTGTCACCCCGTAGCCCCACCTGTTGTCCACTGTAGGTGCCATTCCGGTGCTGTTTTT |
| 146 | NM_010233 | Fn1 | GAACAAACACTAACGTAAATTGCCCCATTGAGTGCTTCATGCCGCTAGATGTGCAAGCTGACAGA |
| 147 | NM_008480 | Lama1 | TTGTAGATGGCAAGGTCTTATTTCACGTCAACAACGGTGCCGGAAGGATAACAGCCACCTACCAG |
| 148 | NM_008610 | Mmp2 | CCTCCTCTGTAGTTAACCAGCCTTCTCCTTCACCTGGTGACTTCAGATTTAAGAGGGTGGCTTCT |
| 149 | NM_010809 | Mmp3 | GTGCTTTGTTCAGCATGTGCTATGGCAGAACCAAACAGGAGCTATGGATGACACCAGTCAACGTC |
| 150 | NM_010810 | Mmp7 | CACCTACAGAATTGTATCCTATACTTCAGACTTACCTCGGATCGTAGTGGATCAAATCGTGAAAA |
| 151 | NM_013599 | Mmp9 | GGGCGCGGCTCCAACCGCTGCATAAATATTAAGGTATTCAG1TGCCCCTACTGGAAGGTATTATG |
| 152 | NM_019471 | Mmp10 | CTCTCGGTTTTCCTCCCACCGTGAAGAAGATTGATGCAGCTGTTTTTGAAAAGGAGAAGAAGAAA |
| 153 | NM_008606 | Mmp11 | TTTCCTGGTAAGTCAGCTCTGGAGAGATAGTGAACTGATCATATTCTGGCAGGTGATTCAGACAA |
| 154 | NM_008605 | Mmp12 | ATCAACTTCATGAGATCCAGAGTCATGTAAGAGACATGTGAGCACTACTTCAAAGAAGGTAAATG |
| 155 | NM_008607 | Mmp13 | CCATGTTTGTTAATCCCTCTCTGCTTTCCTTAGCGAGTAACACTTGGTGCTTACTGATGTGTGAA |
| 156 | NM_008608 | Mmp14 | CCTAGTTGGCTGCCTCCCGCCACTCTGACTAAAAGGAATCTTAAGAGTGTACATTTGGAGGTGGA |
| 157 | NM_008609 | Mmp15 | ACTTAACATTTGGTAGTGATAAGAGGAGAGGACAGCCCAGCTTCCCAAATGACTCCACATCTGGC |
| 158 | NM_019724 | Mmp16 | GAAAGCCATAGCTATTGTCATTCCCTGCATCTTGGCCTTATGCCTCCTTGTATTGGTTTACACTG |
| 159 | NM_011846 | Mmp17 | TAAGTGTCAGGGTCCTCGGGGAGTCATGACAATGTTACCGCCTAACTTGGAGATGTAGGAGCTGT |
| 160 | NM_011985 | Mmp23 | GTGGACAGAAGATCCTACACAAGAAAGGGAAAGTATACTGGTACAAGGACCAGGAACCCCTGGAG |
| 161 | NM_010808 | Mmp24 | TCAACAGCTGCAGGAGCTGACCCTGGTTCTGGGGCGGATGCAAGTTTGTGACCATTCTCTACTC |
| 162 | NM_001033339 | Mmp25 | CTAGGGTCATCACCCTGAACTCAGGATTGCCCCATTCATTTGGAAGGGATCTTATGATTCCTGTC |
| 163 | NM_011593 | Timp1 | GTGAAGAGTTTCTCATCACGGGCCGCCTAAGGAACGGGAAATTTCACATCAATGCCTGCAGCTTC |
| 164 | NM_011594 | Timp2 | CCTCCCTCCCTTACTCCCGTCATGCCAGCAACTCGCAATATTTCAGATGACGTTTACATGGTAGC |

TABLE 3-continued

| SEQ ID NO | Accession No. | Gene symbol | Base sequence of nucleic acid probe |
|---|---|---|---|
| 165 | NM_011595 | Timp3 | TAGATCTAAGTCAGCTGTTTGGGTTGAGGAGGAGAGAACCCGAGGAAATGACCATGCTCTGGGA |
| 166 | NM_080639 | Timp4 | AACCACATCCTTGGAAGCATTCTGAAGACCAAGCCAGTTCTCTGTGGTCCTTTGACCATCACCAC |
| 167 | NM_008604 | Mme | CTACAGCTCATGGACTCTAATTGGATTTCCTGAGGCACTCATATGCCTTCCTTGTCCTTCTGCTT |
| 168 | NM_007974 | F2RL1/PAR2 | AACAAGGGGCCATTGCAGGAGTACATGGCTCCAGGCTTACTTTATATACTGCCTGTATTTGTGGC |
| 169 | NM_007386 | Aco1/IRP1 | CTTACCATTTTCAACGATTGTTGACAGGGGTCCTTTGTTTGAAAATAACTGGGGAGAGATACGGG |
| 170 | NM_080633 | Aco2/Irp2/Mtf1 | AGCCTCAGCCCAGTGAACCACCATTGAGGGCGTTTAAGATAATGTTCCAGCCCCGCCTTCCTGTT |
| 171 | NM_001164109 | Nfatc1 | CCACCACCATTGTGGTCTCGGGGACCAACCGTATTTCCACACCATTAGACTGTGAGCTCCTTCAG |
| 172 | NM_009460 | Sumo1 | CTGAACTGTGGAAAATGACCTTTCCTCAGCTTGAAGCTACTTTTAAAATCTGCGGGTCTGGACCA |
| 173 | NM_133354 | Sumo2 | CTGGGGAAAAATACTGGGTTTGTGAAAATACCCCCTTCTCCACTAGTGGCATGCTCATTCAGCTC |
| 174 | NM_019929 | Sumo3 | CTCCAGGCATTTAATTGACTTAAGTTTCTTATCGGCCTGACACCCAAGTACATCATTGTAGAACC |
| 175 | NM_009627 | Adm | ACATTTCAGAAATTGGCCCACCAGATCTACCAGCTAACAGACAAAGACAAGGACGGCATGGCTCC |
| 176 | NM_022415 | Ptges | GGGCAGGGAGGTGAGTTACGCTAATGCTGGCCAGGATGTATAAAGAAATTCAAGTGTGCACACCT |
| 177 | NM_008968 | Ptgis | AGGACACAGAGGTTCCTGAGTTTGACCTCAGCAGATATGGCTTCGGTCTGATGCAGCCAGAGGAA |
| 178 | NM_001161731 | Ang | CTTTTTATCTCCCCTCATAGCCCAGAACACTGGTTCCATCGTTCATTGTCAGGGGCCAGAAAAAC |
| 179 | NM_013690 | Tek | ATGTGGGTTACTACACAAGAGGCCGAACATTCCAAGTAGCAGAAGAGAGGGTCTCTCAACTCTGC |
| 180 | NM_011587 | Tie1 | CACCTAAAGCAGCATGCATGTTACTAACACCCTGTTTAGCCCCCGACTCTCTGCTTATACTCAGA |
| 181 | NM_010493 | Icam1 | CTACTTTTGTTCCCAATGTCAGCCACCATGCCTTAGCAGCTGAACAATCGAGCCTCATGCTCATG |
| 182 | NM_011693 | Vcam1 | TGATCCCTTGCTGAATGCAAGGAGCTAACCAGAAAAGTTCTGCTTGACAAGTCCCCATCGTTGAA |
| 183 | NM_010612 | Flk1 | TGGTCTCACTACCAGTTAAAGCAAAAGACTTTCAAACAGTGGCTCTGTCCTCCAAGAAGTGGCAA |
| 184 | NM_007742 | Col1a1 | AGGAATTCGGACTAGACATTGGCCCTGCCTGCTTCGTGTAAACTCCCTCCACCCCAATCTGGTTC |
| 185 | NM_007743 | Col1a2 | GGTGGCAGCCAGTTTGAATACAACGTAGAAGGGGTGTCCTCCAAGGAAATGGCAACTCAGCTCGC |
| 186 | NM_009931 | Col4a1 | TCAGGGTTTGCAACACTAACCACAGACTGAATGACTGACTTCCCGTACGACAGCCAAGGCCTTTG |
| 187 | NM_009925 | Col10a1 | ATCCTATTCTCCGCTTAGAAAGGCTTTCCACCCAATTCCATCGCGCCCTCCCTGGAGATGCATTT |
| 188 | NM_001109991 | Col18a1 | GACATCAGCTTGAAGTCCAGAAATCTCACAGCAGCCACATGAAGCACTTGTCCTATGAAGGGACT |
| 189 | NM_008895 | Pomc | TTCCTGGCAACGGAGATGAACAGCCCCTGACTGAAAACCCCCGGAAGTACGTCATGGGTCACTTC |
| 190 | NM_011434 | Sod1 | ACTCTAAGAAACATGGTGGCCCGGCGGATGAAGAGAGGCATGTTGGAGACCTGGGCAATGTGACT |
| 191 | NM_013671 | Sod2 | TAATAAGATCTCTTTAGATCAGCGAAGCCCCTGTTTATCTGAGAGGCGCCGCCTGCCATGAGTAC |
| 192 | NM_011435 | Sod3 | AAGTTCCATGTTCCCGATCACCTCCTGCGGAGGCCCCAGGTTCTG1TTTCATCTGTTTCCCATAT |
| 193 | NM_009804 | Cat | TCTTCTGGACAAGTACAACGCTGAGAAGCCTAAGAACGCAATTCACACCTACACGCAGGCCGGCT |
| 194 | NM_001083929 | Gpx | GCCCAAAGGAAACACAAGTTCTAGGTCCAATGGTTCTGCTCAAACCTGAACATCATTCTTGGGGC |
| 195 | NM_010344 | Gsr | TGAGGCTGGTTAGGTAAAGGAGAAATGACAGTACATGCAAGACGGAAGGCTGAGGCACTCGGGAG |
| 196 | NM_015767 | Ttpa | CCTTCAGTGTCTTTGCTAGATCAAGTGCAGACGCTGCACACAATCTCTAGTTCCTCTAGTTCTGG |
| 197 | NM_007925 | Eln | TTGGTACCCAAATACCGGAAGCCTTGACGATGGATTTGGTGACATGATCCCTCTCTCTTTGGTTC |
| 198 | NM_133918 | Emilin1 | AATCGGTCACTCCGTACGTTGTGACTGCGTGGTCTATGGGACCGAGGCATCTCCTCTTGACCTTT |
| 199 | NM_145158 | Emilin2 | GGCAGACTGGCTCACACAGACTTTGATGAAATGTACTCCACCTTCAGTGGTGTTTCTTGTACCC |
| 200 | NM_009752 | GLB1 | GACGGTCGACCTCCAATTCTTCGGACCTCATACTCCCCACCTTTTACGTGGGCAACTTCTCCATC |
| 201 | NM_153127 | MMRN2 | ACGCCCTGCTTCACTCTGTAAAGGCCAACATATCAAATAGGGACAATGTTGTGCATGGCCTTCAC |

TABLE 3-continued

| SEQ ID NO | Accession No. | Gene symbol | Base sequence of nucleic acid probe |
|---|---|---|---|
| 202 | NM015779 | Elane | ACTTCGTCATGTCAGCAGCCCACTGTGTGAACGGCCTAAATTTCCGGTCAGTGCAGGTAGTGCTG |
| 203 | NM_015776 | Mfap5 | CCGGCTTCCTACCCTACTCTAATTTTCACTGGTGCTGGTAACGTTTGTCTCATTTTGCGGTACTG |
| 204 | NM_001109757 | Atp7a | AATCTGTTGTCTCTCAGATCCCGCTGCCCTGCTGCTGTCACTTAGAACACGAAACAAAGGAATGT |
| 205 | NM_010554 | IL1a | GGAACATCCTTAAATCCTCTGAGCTTGACAGGCATCCTCACAGCAGGATTTTCTAGGTGGTCAGT |
| 206 | NM_008361 | IL1b | CATTAGGCAGCACTCTCTAGAACAGAACCTAGCTGTCAACGTGTGGGGATGAATTGGTCATAGC |
| 207 | NM_009969 | GM-CSF | CCCCAACTCCGGAAACGGACTGTGAAACACAAGTTACCACCTATGCGGATTTCATAGACAGCCTT |
| 208 | NM_011198 | Ptgs2 | GGCTGTTGGAATTTACGCATAAAGCAGACTGCATAGATCCAATATTGACTGACCCAAGCATGTTA |
| 209 | NM_013693 | Tnfa | CTGAACCTCTGCTCCCCACGGGAGCCGTGACTGTAATCGCCCTACGGGTCATTGAGAGAAATAAA |
| 210 | NM_031168 | IL6 | ATCTACTCGGCAAACCTAGTGCGTTATGCCTAAGCATATCAGTTTGTGGACATTCCTCACTGTGG |

TABLE 4

| SEQ ID NO | Accession No. | Gene symbol | Base sequence of nucleic acid probe |
|---|---|---|---|
| 211 | NM_175731 | Acer1 | TGAACAGATGGGTGTGTGGCTGATACAGCACCTGCCTGAAGCATAATGCTTGCTCTCTGTCAGCT |
| 212 | NM_139306 | Acer2 | ATGGTCTCTGGGGACACCCAGCTAGGGCCTTCCCCAACTCCTTATCCAGCTGAACTTGGATTCTT |
| 213 | NM_019734 | Asah1 | CTCCTTCCATAGGCTAAGGCTCAAGGCCTCTTGTCTTTAGTCAGGACTGTCCTCATCATGTTACA |
| 214 | NM_001077411 | Gba | TCTGCAGTTGTGGTCGTGTTAAACCGATCTTCGGAGGATGTCCCTCTTACCATCAGTGATCCTGA |
| 215 | NM_001168525 | Sgms1 | GTGCTTCTTGGGAGAGAAATTTGTCTATGTTTCTAGTGCCTTTCTTGTCTTGATTGTATGGTCGG |
| 216 | NM_009885 | Cel | AGCGCCAAGACCTATTCTTACCTGTTTTCCCACCCTTCACGGATGCCTATCTACCCCAAATGGAT |
| 217 | NM_008079 | Galc | CCCATATAAGCTGGTGCCGTAGGCGAATCTAACTGCTTCCTGTTCATTTCTTGTGCCTTTTGCA |
| 218 | NM_009269 | Sptlc1 | CTCTATAAATTCCAGATGCCTCCGAAAAATAGGGATGCTCTAAACGTGATTTCCGAGCTCTACAC |
| 219 | NM_138647 | Lass1 | TTCCTGTACATTGTGGCTTTCGCAGCCAAGGTGCTGACTGGTCAGATGCGTGAACTGGAAGACTT |
| 220 | NM_172856 | Lass6 | CTGTCCGCGGAATCGTATCCACATATGGCAGGCCATAGCTCTCAGAAAGTCTGACTTGTAAATCC |
| 221 | NM_007853 | Degs1 | CTCTCTGGTTTACTAAGCTAGCCTTAGTGGAATTTCTTTGGTCTGTCTCTGGTACCCCACGTGAT |
| 222 | XM_485270 | Flg | GTGGTCAGGGAGGATATGAGTCCATATTTACAGCAAAGCACCTTGATTTTAATCAATCTCACAGC |
| 223 | XM_485270 | Flg2 | GTGGTCAGGGAGGATATGAGTCCATATTTACAGCAAAGCACCTTGATTTTAATCAATCTCACAGC |
| 224 | NM_008473 | KRT1 | ATCCAGCTCAGGTGGCGGTGGCGTTAAGTCCTCTGGCAGTTCTACCGTGAAGTTTGTTTCCACCA |
| 225 | NM_010668 | KRT2 | TCATCTGTGGCATCTAAGACTGGCTTCGGCTCTGGGGGTCAAAGTTCTGGAGGAAGAGGGTCTTA |
| 226 | NM_008475 | KRT4 | TCTTCTGGGGGCTTCGGCAGCAGAAGTCTTTACAACCTCGGGGGTCACAAGAGTATCTCCATGAG |
| 227 | NM_008008 | FGF7 | ACCTATGCATCAGCTAAATGGACACACAGCGGAGGGAAATGTTCGTTGCCTTAAATCAAAAGGG |
| 228 | NM_023850 | Chst1 | ACAACTGGTAGTTTTGCAATTGTCTTCTCAAGGTAAGAGGATGGACACAAAGGGGCCGTACCTCC |
| 229 | NM_018763 | Chst2 | AGACTGAAGAATCGTGGTGTAGACTGTGGCCAAACAGAGCAATGGCCACTGTCAGAAAGTCCATC |
| 230 | NM_001033239 | Csta | CCCCC1TTTAGTCCAGGAGGGATTTGCACTAGTGAGTACCAGGATTCTAATAAAAGGCTCTTTTC |
| 231 | NM_010635 | Klf1 | GCACAAGGACTGGGGATGAAATAAGAGTGGATCCAAGGACCGTATCCCAAAAGATGGGCCATTAT |
| 232 | NM_010113 | Egf | AACCAGGCTGATGATGGTAGAGTGCTACAGACTTGGTACTCCAGTTTCCACGGCTAATCACTGCT |
| 233 | NM_010415 | Hbegf | TGAGTTGGACTGCAGTCTTGCCTAGGTGATTTTTGTCTACCGTTCGTGTTCCGAAAGCCCAAGGT |
| 234 | NM_009704 | Areg | CTTCAGGGAATATGAAGGAGAAACAGAAGAAAGGAGGCTTCGACAAGAAAACGGGACTGTGC |
| 235 | NM_019812 | Sirt1 | CCAGTTAGGACCATTACTGCCAGAGGAGAAAAGTATTAAGTAGCTCATTTCCCTACCTAAAGAT |

TABLE 4-continued

| SEQ ID NO | Accession No. | Gene symbol | Base sequence of nucleic acid probe |
|---|---|---|---|
| 236 | NM_022432 | Sirt2 | CATAGCCTCTAACCACCATAGCCTCTAACCACCCAGGCAAGAAGCAGCCTTCCCTAACTTCTAAT |
| 237 | NM_022433 | Sirt3 | CATATGGCTGACTTCGCTTTGGCAGATCTGCTACTCATTCTTGGGACCTCCCTGGAGGTGGAGCC |
| 238 | NM_001167691 | Sirt4 | TACTCTGGTTACAGGTTCATCCTCACCGCCCGCGAGCAAAAGCTCCCAATAGCCATTCTGAATAT |
| 239 | NM_022886 | Scel | ACGCCGACACGTGGAAATGAAGATGAGCACCTTCATCGAGGAATTTAAAGCTACATTTAAGAATA |
| 240 | NM_001038612 | Olfm1/Amy | GAAGAAGCAGTCCCCCATGTAACCATGAGAGAGCCAGAGAGCTTTTGCACCATGCATTTTTACG |
| 241 | NM_009354 | Tert | GTGATTCAGCTTCCCTTTGACCAGCGTGTTAGGAAGAACCTCACATTCTTTCTGGGCATCATCTC |
| 242 | NM_009741 | Bcl2 | ATTATTCAATCCGCTATAGACATCTGTGCACTGTGCATCTCTCCAGGCATGAAGAAAACCAGGTA |
| 243 | NM_010031 | Defa1 | GAACAAGACGAGCATGAGTACTGAGGCCACTGATGCTGGTGCCTGATGACCACTTCTCAATAAAT |
| 244 | NM_007843 | Defb1 | CTCTTCCACAGTCTTAGCAGTCAGTTCTATGACACCCCATCTGCAACCTTAGCAATAGAAACTCC |
| 245 | NM_001033228 | Itga1 | TGAATGTACGGTATCATCGTGTGTGAACTACTGCTGTAAAATGTGCTGATCCTCCTGCCCCAAAC |
| 246 | NM_008396 | Itga2 | CCCCTCATGATAATGAAACCCACGGAGAAAGCAGAAGTACCGACAGGGGTTATCATAGGCAGCAT |
| 247 | NM_008317 | Hyal1 | CAAGCACTAGAAGTGGGCTAACTCATTCAGTCTTTGCAATGGACATGCAGGGAAGCTGAGCCTTT |
| 248 | NM_010489 | Hyal2 | ACCTGCCAATACCTCAAGAATTACCTAACTCAGCTGCTGGTTCCCTACATAGTCAACGTGTCCTG |
| 249 | NM_146101 | Habp2 | TGAGGCCTTTTCTCTCTGGGAACCAACAAGAAATACATTATCTTTGCCCCCGTTCTGACAAGTGT |
| 250 | NM_019986 | Habp4 | ATTTCAGGACACGTGGAGAACCGCTCATGTAGAGCAGTCCCACCCCTAATTTTCATACCATTCAC |
| 251 | NM_013500 | Hapln1 | CCTTTTTGAGAAGTATGTCATTGCTCAAGACTGCCAGCACAGTGTACAGCAAAAGCTATGAATAA |
| 252 | NM_013565 | Itga3 | ATATATCATGGAGGGTGCCGTATCCAAGTCTCTGTCTGTGCCAAAACCAAGCCAAAGCGCCTCTA |
| 253 | NM_010576 | Itga4 | TTAAGGTGGAATCAAGTTTACAGACAATCACCTGAATGCTGACTCATTCCTTGTTCACAACCACT |
| 254 | NM_001029872 | Itgad | CTCCCCAGAGCTCACTGTGACAGTAACAGTTTGGAATGAGGGTGAGGACAGCTATGGAACCTTAA |
| 255 | NM_008400 | Itgal | TCTGCTAGCCTGCCTTGTCCCTCTGAGAGAATCTTTGAAATAAACTCGGAGAAACTGCCATCTCA |
| 256 | NM_001082960 | Itgam | CTTCCTAGCTGTTGGGGGTCTCTCCTTAGGGATATTAAAGGGTATATGTTTAGAATCTATTCCAC |
| 257 | NM_008404 | Itgb2 | CTGCCAAGGATCCAAAAGCCTGCTCGGTTTCTTTCCGCCATTATATCAAGTCTGCCAGGGTTTCC |
| 258 | NM_001101 | ACTB | AGTCCTCTCCCAAGTCCACACAGGGGAGGTGATAGCATTGCTTTCGTGTAAATTATGTAATGCAA |
| 259 | NM_001688 | ATP5F1 | GAGACAATTGCCAAGTGCATTGCGGACCTAAAGCTGCTGGCAAAGAAGGCTCAAGCACAGCCAGT |
| 260 | NM_002046 | GAPDH | AGTTGCCATGTAGACCCCTTGAAGAGGGGAGGGGCCTAGGGAGCCGCACCTTGTCATGTACCATC |
| 261 | NM_001514 | GTF2B | GAGCCTTTCATGAGGAAAAACAAAAGACATGGTACGCATTCCAGGGCTGAATACTATTGCTTGGC |
| 262 | NM_000929 | PLA2G5 | CAACACAGAGTACTGACTCTGCCTGGTTCCTGAGAGAGGCTCCTAAGTCACAGACCTCAGTCTTT |
| 263 | NM_001009 | RPS5 | AACAACGGCAAGAAGCTCATGACTGTGCGCATCGTCAAGCATGCCTTCGAGATCATACACCTGCT |
| 264 | NM_006082 | TUBA1B | TGCAGCATGTCATGCTCCCAGAATTTCAGCTTCAGCTTAACTGACAGACGTTAAAGCTTTCTGGT |
| 265 | NM_000181 | GUSB | TGGAAAACAGCCCGTTTACTTGAGCAAGACTGATACCACCTGCGTGTCCCTTCCTCCCCGAGTCA |
| 266 | NM_053275 | RPLP0 | GTCGGACGAGGATATGGGATTGGTCTCTTTGACTAATCACCAAAAAGCAACCAACTTAG |
| 267 | NM_007393 | Actb | CCATCGTGCACCGCAAGTGCTTCTAGGCGGACTGTTACTGAGCTGCGTTTTACACCCTTTCTTTG |
| 268 | NM_008084 | GAPDH | GGGCTGCCATTTGCAGTGGCAAAGTGGAGATTGTTGCCATCAACGACCCCTTCATTGACCTCAAC |
| 269 | NM_010368 | GUSB | GGTCCTCCATTTCCCAGGTGATCCAAATGCCCTTTTGGCCCCTGCGGGTACCACATGTATGGTT |
| 270 | NM_008828 | PGK1 | TTCTGCCTGAGAAAGGAAGTGAGCTGTAAAGGCTGAGCTCTCTCTCTGACGTATGTAGCCTCTGG |
| 271 | NM_007475 | Arbp | ATCAGATGAGGATATGGGATTCGGTCTCTTCGACTAATCCCGCCAAAGCAACCAAGTCAGCCTGC |

TABLE 4-continued

| SEQ ID NO | Accession No. | Gene symbol | Base sequence of nucleic acid probe |
|---|---|---|---|
| 272 | YPL088W-713 | YPL088W-713 | GCATGTTGACTCGTCCTCTGAACCAAAGCACGGACAGGATTAAGAGTGATCCAACTTTCAAGTCG |
| 273 | OmpA | OmpA | GTGTCGGCATAAGCCGAAGATATCGGTAGAGTTATATTGAGCAGATCCCCGGTGAAGGATTTAA |

In the invention, the nucleic acids comprising the base sequence as a control can be also used together with the nucleic acids of (α) described above, and similarly, can be also used together with the nucleic acids of (β), (γ) and (δ) described below.

In addition, the nucleic acids of (β) described above can be also used in evaluation of the influence of ultraviolet ray on the skin and the like in the invention similarly to the nucleic acids of (α) described above. With respect to the nucleic acids of (β) described above, the explanation for the nucleic acids of (α) described above can be similarly applied except that the nucleic acids of (β) comprises the base sequence of the complementary strand of the nucleic acids of (α) described above.

In addition, the nucleic acids of (γ) described above can be also used in evaluation of the influence of ultraviolet ray on the skin and the like in the invention, similarly to the nucleic acids of (α) and (β) described above.

The nucleic acids of (γ) described above are nucleic acids comprising a base sequence having a homology of 70% or higher with respect to the base sequence of the nucleic acids of aforesaid (α) or (β), and further are preferably nucleic acids comprising a base sequence having a homology of 71% or higher, 72% or higher, 73% or higher, 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher. Furthermore, with respect to the explanation for the homology of the base sequence, the explanation for the nucleic acids of (b) described above can be similarly applied.

Furthermore, the expression "can detect the skin constitution-related gene" in the nucleic acids of (γ) described above means "can capture any one of the base sequences of the skin constitution-related genes listed in (a) described above (GBA, GLB1, CAT, OLFM1, ASAH1, MMP14, MMP17 and COL18A1) and the base sequence of the complementary strand by hybridization.

Further, the nucleic acids of (δ) described above can be also used in the evaluation of the influence of ultraviolet ray on the skin and the like, similarly to the nucleic acids of (α), (β) and (γ) described above.

The nucleic acids of (δ) described above are base sequences of which one to several (for example, 1 to 15, 1 to 10, or 1 to 5, or 1 to 2) bases are added, deleted or substituted in the base sequence of the nucleic acids of (α), (β) and (γ) described above. Examples of the nucleic acids of (δ) include those in which the end of the base sequence of the nucleic acids of (α), (β) and (γ) described above is modified with linker bases (polyT and the like), those in which separate bases are inserted into a portion of the base sequence, those in which a portion of the bases of the base sequence are deleted, those in which a portion of the bases of the base sequence are substituted with separate bases, and the like.

As described above, the mutated sequences by addition, deletion or substitution of desired bases, particularly substitution-type mutated nucleic acids, can be manufactured in accordance with, for example, the site-directed mutation induction method described in "Molecular cloning, A Laboratory Manual 3rd ed.", "Current Protocols in Molecular Biology, John Wiley & Sons (1987-1997)" and the like described above. Specifically, the substitution-type mutated nucleic acids can be manufactured using a kit for introducing mutation utilizing the site-directed mutation induction method by a known method such as the Kunkel method or the Gapped duplex method. Examples of the kit preferably include QuickChange™ Site-Directed Mutagenesis Kit (manufactured by Stratagene Corporation), GeneTailor™ Site-Directed Mutagenesis System (manufactured by Invitrogen), TaKaRa Site-Directed Mutagenesis System (Prime STAR (registered trade-mark) Mutagenesis Basal kit, Mutan (registered trade-mark)-Super Express Km and the like: manufactured by TAKARA BID INC.) and the like.

Furthermore, with respect to the expression "can detect the skin constitution-related gene" in the nucleic acids of (δ) described above, the explanation for the nucleic acids of (γ) described above can be similarly applied.

The nucleic acids of (α), (β), (γ) and (δ) described above are not limited to the full lengths of the nucleic acids, and a portion thereof can be used as a probe, similarly to the nucleic acids of (a), (b) and (c) described above.

In addition, as the probe set for evaluating the influence of ultraviolet ray on the skin in the invention, for example, those composed of the nucleic acids of (i) and/or (ii) described below can be also used.

(i) Nucleic acids comprising the base sequences shown in SEQ ID NOS: 1 to 130

(ii) Nucleic acids comprising the base sequences shown in SEQ ID NOS: 131 to 257

Herein, the nucleic acids of (i) described above correspond to a portion of the nucleic acids comprising the base sequences of the human-derived skin constitution-related genes, and the nucleic acids of (ii) described above correspond to a portion of the nucleic acids comprising the base sequences of the mouse-derived skin constitution-related genes.

A method for obtaining the various nucleic acids described in the specification is not particularly limited, and the various nucleic acids can be acquired by a known genetic engineering method or a known synthesis method. For example, the various nucleic acids can be obtained by using a commercially available DNA synthesizer, and the like.

In addition, the various nucleic acids that can be used as a probe may be suitably modified, and examples thereof include those in which the end is vinylated (acryloylated, methacryloylated) or those in which the end is aminated, those modified with a linker bases (polyT and the like), and the like. In addition, as the various nucleic acids, used may be those obtained by inserting separate bases into a portion of the base sequence of the various nucleic acids, or those obtained by deleting a portion of the bases of the base sequence, or those obtained by substituting a portion of the bases of the base sequence with separate bases, or with substances other than the bases. Herein, examples of the substances other than the bases include dyes (fluorescent dyes, intercalators), quenching groups and base-crosslinking agents.

3. Nucleic Acid Microarray

A nucleic acid microarray is an array in which many nucleic acid probes are immobilized respectively, independently in a high density on support. A nucleic acid microarray is a system utilized for analyzing the expression amount associated with multiple nucleic acid base sequences or the sequence of a specific nucleic acid base sequence itself.

The nucleic acid microarray of the invention is loaded with the probes of the invention described above. The nucleic acid microarray of the invention is not limited if the probes of the invention are fixed on a support. For example, the probes that can hybridize with each mRNA derived from the skin constitution-related genes described above are fixed, respectively on a support, whereby to perform detection and quantification of the expressions of multiple skin constitution-related genes at the same time.

In the nucleic acid microarray, the form of the support is not particularly limited, and any form such as a plate, a rod and a bead may be used. In the case where a plate is used as the support, prescribed probes can be fixed every kind on the plate with a prescribed interval (see the spotting method and the like; Science 270, 467-470 (1995) and the like). In addition, prescribed probes can be sequentially synthesized every kind at certain positions on the plate (see the photolithography method and the like; Science 251, 767-773 (1991) and the like).

Examples of the other preferable forms of the support include those using hollow fibers. In the case where hollow fibers are used as the support, preferably exemplified may be a nucleic acid microarray obtained by fixing the probes every kind onto each hollow fiber, and bundling and fixing all of the hollow fibers, and then repeating cutting in the longitudinal direction of the fiber. This nucleic acid microarray can be explained as a type in which the probes are fixed on a through-hole substrate, which is also referred to as so-called "through-hole type microarray" (see Japanese Patent No. 3510882 and the like, or FIG. 1 of the present application).

A method for fixing the probes on the support is not particularly limited, and the probes may be fixed on the support in any binding mode. In addition, the method is not limited to direct fixing on the support, but, for example, the support may be previously coating-treated with a polymer such as polylysine, and the probe may be fixed on the support after the treatment. Further, in the case where a tubular body such as a hollow fiber is used as the support, a gelatinous substance may be kept on the tubular body, and the probes may be fixed on the gelatinous substance.

Hereinafter, the through-hole type nucleic acid microarray by the hollow fibers is explained in detail. This microarray can be manufactured, for example, through the processes (i) to (iv) described below.

(i) A process of disposing multiple hollow fibers three-dimensionally so that the longitudinal directions of the hollow fibers are in the same direction whereby to manufacture an array (ii) A process of embedding aforesaid array whereby to manufacture a block body (iii) A process of introducing a polymerizable solution of a gel precursor containing the probes into the hollow part in each hollow fiber of aforesaid block body whereby to perform the polymerization reaction and keep the gelatinous substance containing the probes in the hollow part (iv) A process of cutting the hollow fibers in the direction intersecting the longitudinal direction of the hollow fibers whereby to flake the block body The material used for the hollow fiber is not limited, but examples thereof preferably include the materials described in JP-A No. 2004-163211 and the like.

The hollow fibers are disposed three-dimensionally so that the lengths of the longitudinal direction are the same (the process (i)). Examples of the method for disposing the hollow fibers include a method in which multiple hollow fibers are arranged in parallel on a sheet-like material such as an adhesive sheet with a prescribed interval to give a sheet form, and then this sheet is helically rolled (see JP-A No. 11-108928), a method in which two perforated plates where multiple holes are installed at a prescribed interval, are superposed so that the hole parts coincide, and the hollow fibers are passed through the hole parts, and then the interval of the two perforated plates is opened to fix the hollow fibers temporarily, and a hardening resin material is charged around the hollow fibers between the two perforated plates and hardened (see JP-A No. 2001-133453) and the like.

The manufactured array is embedded such that the sequence is not disrupted (the process (ii)). Examples of the embedding method preferably include a method in which a polyurethane resin, an epoxy resin and the like is poured into the gap between the fibers, a method in which the fibers are bonded to each other by heat fusion, and the like.

The embedded array is filled with a polymerizable solution of a gel precursor (gel forming solution) comprising the probes in the hollow part in each hollow fiber, and the polymerization reaction is performed in the hollow part (the process (iii)). By this, it is possible to keep a gelatinous substance in which the probes are fixed in the hollow part in each hollow fiber.

The gel precursor-polymerizable solution refers to a solution containing a reactive substance such as a gel forming-polymerizable monomer, and being able to become a gelatinous substance by polymerizing and crosslinking the monomer and the like. Examples of such monomer include acrylic amide, dimethylacrylic amide, vinyl pyrrolidone, methylene bisacrylic amide and the like. In this case, the solution may contain a polymerization initiator and the like. The probes are fixed in the hollow fibers, and then the block body is cut and flaked in the direction intersecting the longitudinal direction of the hollow fiber (preferably orthogonal direction) (the process (iv)). Thus-obtained flake can be used as the nucleic acid microarray. The thickness of the array is preferably 0.01 mm to 1 mm or so. The cutting of the block body can be performed with, for example, a microtome, a laser or the like. Examples of the through-hole type microarray preferably include the nucleic acid microarray manufactured by Mitsubishi Rayon Co., Ltd. (Genopal™) and the like.

4. Evaluation of the Skin Condition

According to the invention, the expression amount of the skin constitution-related gene is measured using the probe or the probe set or the nucleic acid microarray of the invention described above, whereby to comprehensively evaluate the influence of external stimulation on the skin of a target object (a test subject), particularly the influence of ultraviolet ray on the skin condition such as skin elasticity and wrinkle.

The measurement of the expression amount of the skin constitution-related gene can be performed by, for example, applying external stimulation to the skin or skin culture cells of an animal as a target object (particularly, irradiating the skin or skin culture cells of an animal with ultraviolet ray), and then extracting mRNA from the skin or the culture cells. As the mRNA, the mRNA contained in the target object can be used as it is, or cDNA obtained by reverse transcription (or reverse transcription and amplification) from the mRNA, or aRNA (amplified RNA) obtained by transcriptional amplification of the cDNA can be used. Further, the amplification product is preferably labelled with a fluorescent labelling agent including biotin, an intercalator, metal particles, a luminous enzyme or the like.

The animal from which the skin or the culture cells are derived is not limited, and examples thereof include a human, a mouse, a rat, a hamster, a pig, a guinea pig, a monkey, a dog, a cat and the like. The kind of the culture cell is not particularly limited if it is a cell associated with the skin, and examples thereof may include a normal epithelium cell, a normal melanocyte, a normal keratinocyte cell, an epithelium fibroblast, a melanoma cell and the like.

The hybridization reaction can be performed by suitably setting up the reaction conditions (the kind of a buffer solution, the pH, the temperature and the like) where mRNA, cDNA or aRNA obtained as described above can hybridize with the probes loaded into the microarray under the stringent conditions. Furthermore, the "stringent conditions" herein is as described above.

After the washing, the detection intensity is measured for each probe by an apparatus that can detect the labelling of mRNA, cDNA or aRNA bound to the probes. Based on the detection results (signal intensity) obtained from the labelling agent and the like, it is possible to evaluate the significance of the expression amount of the various target genes by a known treatment method.

5. Screening Method

In the invention, it is possible to provide a method of screening a compound that is useful in a skin disease remedy or a cosmetic using the probe or the probe set or the nucleic acid microarray of the invention.

The screening can be specifically performed by, for example, applying external stimulation of UVB on the skin or the skin culture cells of an animal, and then bringing a candidate substance into contact with the animal or the culture cells, measuring the expression amount of the skin constitution-related gene, and comparing and analyzing the expression amount with that of the gene of a control group (the case of not being brought into contact with the candidate substance, and the like). In addition, in some cases, the skin or the skin culture cells may be brought into contact with the candidate substance before the external stimulation. The contact herein refers to administration of the candidate substance percutaneously (application or paste onto the skin, and the like), orally, intraperitoneally, subcutaneously, intravenously and the like in the case of an animal, or refers to addition of the candidate substance into the culture solution in the case of the culture cells.

Examples of the control group include the case where the external stimulation is applied without contact of the candidate substance, the case where the external stimulation is not applied with contact of the candidate substance, the case where the external stimulation is not applied without contact of the candidate substance, and the like.

Furthermore, examples of the candidate substance that can be used include arbitrary, various compounds, and may be those derived from the nature or those artificially manufactured, and is not limited.

The data for the expression amount of the control gene may be acquired from the same test subject, or may be acquired from multiple different test subjects of the same kind, or may be those previously accumulated in the database. In addition, the measured expression amount data derived from the test subject may be incorporated into the value of the population (the test subject) whereby to data-treat again the level of the expression amount (averaging and the like), and increase the number of the cases of the population. By increasing the number of the cases, it is possible to increase the accuracy of the critical value of the expression amount. In some cases, by suitably modifying the critical value, it is possible to increase the accuracy of the screening.

As the comparison and analysis of the gene-expression amount, the gene-expression amount in the case of contact with the candidate substance can be evaluated in the point whether or not the gene-expression amount is close to the gene-expression amount in the case where the external stimulation is not applied. As the evaluation method for the gene-expression amount, the gene-expression amount can be evaluated by patterning the temporal change of the gene-expression amount or the change depending on the conditions, and specifically the evaluation can be performed using multivariate analysis. Examples of the multivariate analysis include comparison of the pattern and prediction of the effects using main ingredient analysis, factor analysis, distinction analysis, quantification theory (Class I, Class II, Class III, and Class IV), cluster analysis, multidimensional scaling (MDS), multiple regression analysis, conjoint analysis, Mahalanobis and Taguchi system (MT method), and the like.

The concentration and the amount of the candidate substance that is brought into contact with the animal or the culture cells can be suitably set up and selected depending on the kind of the candidate substance or the test subject, and the like. The contact is preferably performed in the concentration and the amount at which no toxicity from the candidate substance is caused to the test subject so that there is no influence that is an obstacle in extracting the nucleic acid. The expression "no toxicity from the candidate substance is caused" refers to, for example, at least no death, or no partial necrosis observed in the case of the animal, or at least 90% or higher of the cell survival rate in the case of the culture cells.

A method for extracting the nucleic acids or a method for treating the extracted nucleic acids is not limited, and may be performed with a known method, and is preferably performed with a method suitable for the kind of the microarray to be used. For example, in the case where Total RNA is isolated, RNeasy mini kit (QIAGEN), which is a reagent kit of commercial products, or the like may be used, and the extraction may be performed in accordance with the accessory protocol. In addition, in the case where RNA is amplified depending on the circumstances, Message AmpII-Biotin Enhanced kit (manufactured by Applied Biosystems), which is a kit of commercial products, may be used, and aRNA amplified in accordance with the accessory protocol may be manufactured and measured.

Among the data as the measurement results, only those having a value equal to or higher than the determination value are used in the evaluation. The determination value used may be the average value X of the negative control genes, and further is a value obtained by adding the standard deviation σ to X, further desirably X+2σ, and further desirably X+3σ. Furthermore, the negative control is a gene not detected from a test subject, and is, for example, a gene of a different kind of organism from that of the test subject, and the like.

The error between respective samples of the obtained data is corrected with the value of the housekeeping gene (gapdh, actin, arbp and the like), and using the corrected data, the change of the mRNA amount is determined (the change of the mRNA amount is statistically determined by the test. 3 or higher sample number (n) is acquired from each of the test subjects, and the t-test is performed. In the case where P value is 0.05 or less, and further is 0.01 or less, it is determined that the mRNA amount has significantly changed.). The candidate substance that is used in the case where the mRNA amount has not been determined to have been significantly changed as a result of the determination, can be judged as a candidate substance of which the gene-expression amount can be close to the gene-expression amount in the case where the external stimulation is not given as described above, and can be judged to be screened as a compound that is useful in a skin disease remedy or a cosmetic.

EXAMPLES

Hereinafter, the invention is further specifically explained by Examples. However, the invention is not limited to these Examples.

Example 1

(1) Manufacture of Hollow Fiber Bundle

A hollow fiber bundle was manufactured utilizing the sequence fixing apparatus shown in FIG. 1. Furthermore, x, y and z in the figure are orthogonal, 3-dimensional axes, and the x axis coincides with the longitudinal direction of the fiber.

First, two pieces of perforated plates having a 0.1 mm thickness on which holes having a 0.32 mm diameter are installed in total 256 in 16 rows of the horizontal and vertical lines, respectively at 0.12 mm of the distance between the holes, were prepared. These perforated plates were superposed, and through all of the holes, polycarbonate hollow fibers having 280 μm of the outer diameter, 180 μm of the internal diameter and 150 mm of the length were passed one by one.

The positions of the two pieces of the perforated plates were moved such that the perforated plates were fixed at two positions of 20 mm and 100 mm from one end of the hollow fiber in a state that each fiber was applied with 0.1 N of the tension in the direction of the axis X. In other words, the interval between the two pieces of the perforated plate was 80 mm. Then, the three sides around the space between the perforated plates were surrounded with a plate-like material. In this way, a container of which the top only was in the open state, was obtained.

Next, a resin material was poured into the container from the top of this container. As the resin, a resin obtained by adding 2.5 mass % of carbon black to the total mass of a polyurethane resin adhesive (NIPPOLAN 4276 and CORONATE 4403 manufactured by NIPPON POLYURETHANE INDUSTRY Co., Ltd.) was used. The resin was left at 25° C. for 1 week to harden the resin. Then, the perforated plates and the plate-like material were removed, and a hollow fiber bundle was obtained. The obtained hollow fiber bundle was put into a desiccator and the inside was purged with nitrogen, and then left for 16 hours.

(2) Immobilization of Probe into Hollow Thread and Slice

A gel polymerization precursor solution (Table 5: the unit is mL) of the composition comprising the probes of the genes selected from the sequence listing (vinylated nucleic acid was purchased from BEX CO., LTD.) was dispensed to each well of a microwell plate by 36 μL. The well plate was established in a desiccator, and the gel precursor solution dispensed to each well was sucked from the end, and introduced into the hollow part of the hollow fiber.

TABLE 5

| Composition | Mass ratio (Probe: Concentration) |
|---|---|
| N,N'-dimethylacrylic amide | 3.42 |
| N,N'-methylenebisacrylic amide | 0.38 |
| 2,2'-azobis(2-methylpropionamidine) dihydrochloride | 0.01 |
| Aqueous solution of Probe (pmol/μL) | 5 |
| Pure water | 98.19 |

Then, the hollow fiber bundle was established in the desiccator, and the inside of the desiccator was heated to 55° C. under a nitrogen atmosphere, and the polymerization reaction was performed at 55° C. for 3 hours.

After completion of the polymerization reaction, the hollow fiber bundle was flaked in 250 μm of the thickness in the direction perpendicular to the longitudinal direction of the hollow fiber using a microtome. In this way, 300 pieces of the nucleic acid microarrays having 250 μm of the thickness loaded with gel spots comprising 228 capture probes were manufactured.

(3) Measurement of Sample Using Manufactured Nucleic Acid Microarray

Fibrocytes (RIKEN BRC CELL BANK) were inoculated on a 96 well plate in $2.0 \times 10^4$ cells/well, and cultured for 24 hours on a DMEM medium containing 10% FBS (Sigma-Aldrich Co. LLC.). The time before UVB (ultraviolet ray B wave) irradiation was taken as time zero, and the medium was removed from some of the wells and the wells were added with PBS and irradiated with UVB (30 mJ/cm2). After UVB irradiation, PBS was removed, and the medium was added and cultured again for 3, 6, 9, 12, 24, 36, 48 and 72 hours.

The cell at each culture time was washed with PBS(−), and gene expression analysis by the nucleic acid microarray was performed. Manufacture of a sample for the gene expression analysis by the nucleic acid microarray was performed according to the protocol of Rneasy Mini Kit (manufactured by Qiagen).

The cells were washed with PBS(−), and then collected with trypsin treatment, and precipitated at 1000 rpm, and the supernatant was removed, and then 175 μL of PBS(−) was added. To 175 μL of the cell sample solution, 175 μL of RLT solution accompanied in the kit was added, and 1 mL syringe was inserted 5 times, to crush the cells. To the crushed solution, 70% ethanol was added, and pipetting was performed 5 times. Then, the solution was added to the accompanied column, and centrifuged (1 minute at 13000 rpm), and then washed with the accompanied 1700 μL RW and 500 μL RPE (1 minute at 13000 rpm, respectively), and eluted with 30 μL RNase free Water whereby to perform the RNA purification.

Next, manufacture of aRNA was performed from 1 mg Total RNA in accordance to the accompanied protocol using Message Amp II-Biotin Enhanced kit (manufactured by Applied Biosystems). 5 μg aRNA was put into a plastic tube, and 4 μL of 5× Array Fragmentation Buffer accompanied in Message AmpII-Biotin Enhanced kit (manufactured by Applied Biosystems) was added to the plastic tube. The plastic tube was diluted to 20 μL and well mixed, and then heated at 94° C. for 7.5 minutes whereby to perform fragmentation of aRNA. To 20 μL of the solution after the fragmentation, 18 μL of 1 M Tris-HCl solution (manufactured by Invitrogen), 18 μL of 1 M NaCl solution (manufactured by nacalai tesque) and 15 μL of 0.5% Tween 20 solution were mixed, respectively, and the mixture was diluted to 150 μL with Nuclease-free water, whereby to manufacture a specimen solution.

Into the manufactured specimen solution, a nucleic acid microarray (nucleic acid microarray manufactured by Mitsubishi Rayon Co., Ltd. (Genopal™)) was dipped, and the hybridization reaction was performed for 16 hours at 65° C. The specimen solution used in the hybridization was removed from the array, and then the array was dipped into 0.12 M TNT solution (solution of 0.12 M Tris-HCl, 0.12M NaCl, 0.5% and Tween 20) at 65° C. (for 20 minutes×twice), and then dipped into 0.12 M TN solution (0.12 M Tris-HCl, 0.12 M NaCl) warmed to 65° C. for 10 minutes to be washed. Then, the signals of the nucleic acid microarray were detected.

Detection of the signal in the nucleic acid microarray was performed by measuring the Cy5 fluorescent intensity using an apparatus for detection of a nucleic acid microarray (MB-M3A manufactured by Yokogawa Electric Corporation, laser wavelength: 633 nm) (exposure time: 0.1 sec, 1 sec, 4 sec, 40 sec). Furthermore, the results were subtracted with the background, and then corrected using the values of Actin, Arbp and Gapdh, and the results showed temporal changes of the signal values.

The results are shown in FIG. 2 (FIG. 2A to 2H). From the results of FIG. 2, examples of the genes that have significantly changed in the expression difference due to the difference of the UVB irradiation conditions since 38th hour in comparison to the negative control include GBA, GLB1, CAT, OLFM1, ASAH1, MMP14, MMP17 and COL18A1 (see each of the graphs of FIG. 2F: No. 85, FIG. 2E: No. 70, FIG. 2D: No. 63, FIG. 2G: No. 112, FIG. 2E: No. 84, FIG. 2B: No. 27, FIG. 2B: No. 30, and FIG. 2D: No. 58, respectively in order). These genes are suggested to reflect the influence of UVB irradiation, and using these genes, the influence on the skin can be evaluated.

From these results, conditions having the influence on the skin constitution such as skin elasticity, wrinkle and texture can be evaluated quantitatively.

INDUSTRIAL APPLICABILITY

According to the invention, it is possible to provide a probe or a probe set which can objectively evaluate the influence of external stimulation, particularly ultraviolet ray on the skin at the gene expression level, and a nucleic acid microarray which is loaded with the probe or the probe set. The probe or a probe set, and the nucleic acid microarray are highly useful in the point that they can be used in a method of evaluating the influence of ultraviolet ray on the skin of a test subject, and a method of effectively screening a substance (compound and the like) that is useful as an active ingredient of a skin disease remedy (percutaneous absorption-type formulation and the like) or a cosmetic.

EXPLANATIONS OF LETTERS OR NUMERALS

1 Sequence fixing apparatus
11 Hole part
21 Perforated plate
31 Hollow fiber
41 Plate-like material

The invention claimed is:

1. A method of detecting a change of an expression amount of a skin constitution-related gene due to ultraviolet ray irradiation, comprising:
   irradiating the skin or a skin culture cell with an ultraviolet ray;
   measuring an expression amount of a skin constitution-related gene in the skin or the skin culture cell irradiated by the ultraviolet ray using a probe or a probe set comprising at least one of a nucleic acid of (iii) and (iv):
   (iii) a nucleic acid comprising all base sequences of SEQ ID NOS: 1 to 130;
   (iv) a nucleic acid comprising all base sequences of SEQ ID NOS: 131 to 257; and
   detecting a difference between the measured expression amount of the skin constitution-related gene and an expression amount of the skin constitution-related gene in the skin or a skin culture cell not irradiated by the ultraviolet ray.

2. The method of claim 1, wherein, in the measuring, the expression amount of at least one gene selected from the group consisting of GBA, GLB1, CAT, OLFM1, ASAHL MMP14, MMP17 and COL18A1, is measured.

3. The method of claim 1, wherein, in the measuring, the expression amount of at least one gene selected from the group consisting of GBA, GLB1, CAT, OLFM1 and ASAHL and at least one gene selected from the group consisting of MMP14, MMP17 and COL18A1, is measured.

4. The method of claim 1, wherein the probe or the probe set is immobilized on a support to form a nucleic acid microarray comprising the probe or the probe set.

5. The method of claim 1, wherein the ultraviolet ray is UVB.

6. The method of claim 1, wherein the skin or the skin culture cell is irradiated with the ultraviolet ray for at least 38 hours.

7. The method of claim 5, wherein the skin or the skin culture cell is irradiated with the ultraviolet ray for at least 38 hours.

8. The method of claim 1, wherein, in the irradiating, the skin is irradiated with the ultraviolet ray.

9. The method of claim 1, wherein, in the irradiating, a skin culture cell is irradiated with the ultraviolet ray.

* * * * *